US007361496B1

(12) United States Patent
Clarke et al.

(10) Patent No.: US 7,361,496 B1
(45) Date of Patent: Apr. 22, 2008

(54) RESCUE OF MUMPS VIRUS FROM CDNA

(75) Inventors: David K. Clarke, Chester, NY (US); J. Erik Johnson, Verona, NJ (US); Mohinderjit S. Sidhu, Scotch Plains, NJ (US); Stephen A. Udem, New York, NY (US)

(73) Assignee: Wyeth, Madison, NJ (US)

( * ) Notice: Subject to any disclaimer, the term of this patent is extended or adjusted under 35 U.S.C. 154(b) by 592 days.

(21) Appl. No.: 10/048,384

(22) PCT Filed: Aug. 2, 2000

(86) PCT No.: PCT/US00/21192

§ 371 (c)(1),
(2), (4) Date: Jan. 6, 2003

(87) PCT Pub. No.: WO01/09309

PCT Pub. Date: Feb. 8, 2001

(51) Int. Cl.
*C12N 7/00* (2006.01)

(52) U.S. Cl. ............... 435/235.1; 435/69.1; 435/320.1; 435/239; 435/455; 435/456; 435/471; 435/476

(58) Field of Classification Search ............... 435/69.1, 435/455, 471, 476, 235.1, 239, 320.1, 456
See application file for complete search history.

(56) References Cited

FOREIGN PATENT DOCUMENTS

| | | | |
|---|---|---|---|
| WO | WO97/06270 | * | 2/1997 |
| WO | WO97/12032 | | 4/1997 |
| WO | WO98/13501 | | 4/1998 |
| WO | WO99/63064 | | 12/1999 |

OTHER PUBLICATIONS

Afzal et al., J Gen Virol. vol. 74, pp. 917-920.*
Schnell et al., The EMBO Journal 1994 vol. 13, No. 18, pp. 415-426.*
Azfal et al., J Gen Jirology 1993 vol. 74, pp. 4195-4203*
Durbin et al., Virology vol. 235, pp. 323-332. 1997.*
Afzal et al., J Gen Virol. vol. 74, pp. 917-920, 1995.*
Thomas R. Fuerst, et al., Proc. Natl. Acad. Sci., vol. 83, pp. 8122-8126, 1986.
Narayanasamy Elango, et al., J. Gen. Virol., vol. 69, pp. 2893-2900, 1988.
Reay G. Paterson and Robert A. Lamb, Journal of Virology, vol. 64, No. 9, pp. 4137-4145, 1990.
B. Moss, et al., Nature, vol. 348, pp. 91-92, 1990.
Philippe Calain and Laurent Roux, Journal of Virology, vol. 67, No. 8, pp. 4822-4830, 1993.
M.A. Afzal, et al., Journal of General Virology, vol. 74, pp. 917-920, 1993.
Matthias J. Schnell, et al., The EMBO Journal, vol. 13, No. 18, pp. 4195-4203, 1994.
Jean-Christophe Boyer and Anne-Lise Haenni, Virology, vol. 198, pp. 415-426, 1994.
Dominique Garcin, et al., EMBO Journal, vol. 14, No. 24, pp. 6087-6094, 1995.
Mohinderjit S. Sidhu, et al., Virology, vol. 208, pp. 800-807, 1995.
Sean P.J. Whelan, et al., Proc. Natl. Acad. Sci. USA, vol. 92, pp. 8388-8392, 1995.
Linda S. Wyatt, et al., Virology, vol. 210, pp. 202-205, 1995.
Gerd Sutter, et al., FEBS Letters, vol. 371, pp. 9-12, 1995.
Peter L. Collins, et al., Proc. Natl. Acad. Sci. USA, vol. 92, pp. 11563-11567, 1995.
Frank Radecke, et al., The EMBO Journal, vol. 14, No. 23, pp. 5773-5784, 1995.
Nathan D. Lawson, et al., Proc. Natl. Acad. Sci. USA, vol. 92, pp. 4477-4481, 1995.
Kaoru Takeuchi, et al., Virology, vol. 225, pp. 156-162, 1996.
Robert A. Lamb and Daniel Kolakofsky, Fields Virology, Third Edition, Chapter 40, pp. 1177-1204, 1996.
Michael A. Hoffman and Amiya K. Banerjee, Journal of Virology, vol. 71, No. 6, pp. 4272-4277, 1997.
Biao He, et al., Virology, vol. 237, pp. 249-260, 1997.
Susan K. Murphy and Griffith D. Parks, Virology, vol. 232, pp. 145-157, 1997.
Henriette Schneider, et al., Journal of Virological Methods, vol. 64, pp. 57-64, 1997.
Michael D. Baron and Thomas Barrett, Journal of Virology, vol. 71, No. 2, pp. 1265-1271, 1997.
Anna P. Durbin, et al., Virology, vol. 235, pp. 323-332, 1997.
Hong Jin, et al., Virology, vol. 251, pp. 206-214, 1998.
Ursula J. Buchholz, et al., Journal of Virology, vol. 73, No. 1, pp. 251-259, 1999.
Ben P.H. Peeters, et al., Journal of Virology, vol. 73, No. 6, pp. 5001-5009, 1999.

* cited by examiner

*Primary Examiner*—Bruce R. Campell
*Assistant Examiner*—Myron G. Hill
(74) *Attorney, Agent, or Firm*—Darrell Fontenot

(57) ABSTRACT

This invention relates to a method for recombinantly producing, via rescue of mumps virus, a nonsegmented, negative-sense, single-stranded RNA virus, and immunogenic compositions formed therefrom. Additional embodiments relate to methods of producing the mumps virus as an attenuated and/or infectious virus. The recombinant viruses are prepared from cDNA clones, and, accordingly, viruses having defined changes, including nucleotide/polynucleotide deletions, insertions, substitutions and re-arrangements, in the place of the genome are obtained.

1 Claim, 16 Drawing Sheets

Confirmation of RMUV by Consensus Sequencing
Censensus of parent plaque isolate
RMUV cons Seq.
nt ACATTGCGACCAAAGAAATCA nt
nt ACATTGCGACTAAAGAAATCA nt
nt6081
nt GTTAGATATAGGCTTTTCTAC nt
nt GTTAGATATAAGCTTTTCTAC nt
nt8502
nt TTCACTGGAGGTGAGGCCACTGT nt
nt TTCACTGGAGGTAAGGCCACTGT nt
nt 11731
A
B
C

Fig. 8

Table 1

Mumps Virus Sequence Comparisons

| Position[1] | MuV consensus[2] | PI 4[3] | MuV FL-clone DC1[4] | AA change[5] | gene (AA position)[6] |
|---|---|---|---|---|---|
| 214 | G | T | T | glu to asp | N (23) |
| 6081 | T | T | C | silent | F (512) |
| 8459 | C | T | T | leu to phe | L (8) |
| 8502 | A | A | G | lys to arg | L (22) |
| 11632 | T | G | G | silent | L (1065) |
| 11731 | A | A | G | silent | L (1098) |

[1]nucleotide position within the mumps virus genome.

[2]nucleotide at indicated position in mumps virus consensus sequence.

[3]nucleotide at indicated position in Plaque Isolate 4 (PI 4) sequence, which was used to make the full length cDNA clone.

[4]nucleotide at indicated position in the mumps virus (MuV) full length (FL) cDNA clone (DC1) derived from PI 4 sequence and used in rescue experiments.

[5]indicates whether the nucleotides at the indicated positions cause a coding change or are silent. Note that all positions indicated in the table fall within coding regions.

[6]indicates the mumps virus gene followed by the amino acid number (in parentheses) that corresponds to the indicated nucleotide position.

Fig. 9

Table 2

Mumps Virus Jeryl Lynn Gene Start and End Signals

| Intergenic | Gene start | Gene (gene length) | Gene end |
|---|---|---|---|
| 1 | | 3' Leader | |
| 55 UGGUUCCCCUCUUACUUAUACCCUAUAACCAUCUUGUUUAUCACAUUCUUUGUC | | | |
| | 56 UUCGGGCCU | ----NP(1851)--- | 1,906 AAUUCUUUUUU |
| AA | 1,909 UCCGGGCCU | ----P(1318)---- | 3,226 AUUUAUUUUUU |
| A | 3,228 UUCGUGCUU | ----M(1254)---- | 4,481 AUAUCUUUUUU |
| A | 4,483 UUCGGAUCU | ----F(1728)---- | 6,210 AAAUCUUUUUUU |
| GAUUUUA | 6,218 UUCUUACUU | ----SH(316)---- | 6,533 AUUUCUUUUUU |
| CG | 6,536 UUCGGUCUU | ----HN(1893)--- | 8,428 AAUUCUUUUUU |
| G | 8,430 UCCGGUCUU | ----L(6931)---- | 15,360 AAUUCUUUUUU |
| | 15,361 | 5' Trailer      15,384 AACUAAAAUGAAAGAGGGGAACCA | |
| Consensus sequence*: | UuCgggcuU | | AauUcU$_{6-7}$ |

*Lower case represents the base that is the majority in the consensus.

Note: All sequences are presented in the genome (-) sense.

Fig. 10

Table 3
Mumps Virus Jeryl Lynn Genes

| Gene | Gene start[1] | Translation start[2] | Translation end[3] | Gene end[4] | Length (nt)[5] | Length (AA)[6] |
|---|---|---|---|---|---|---|
| NP | 56 | 146 | 1795 | 1906 | 1851 | 549 |
| P[7,8] | 1909 | 1979 | 3152 | 3226 | 1318 | 391 |
| M | 3228 | 3264 | 4391 | 4481 | 1254 | 375 |
| F | 4483 | 4546 | 6162 | 6210 | 1728 | 538 |
| SH | 6218 | 6268 | 6441 | 6533 | 316 | 57 |
| HN | 6536 | 6614 | 8362 | 8428 | 1893 | 582 |
| L | 8430 | 8438 | 15223 | 15360 | 6931 | 2261 |

[1] Refers to the gene transcription start nucleotide position.
[2] Refers to the gene translation start nucleotide position.
[3] Refers to the gene translation stop nucleotide position.
[4] Refers to the gene transcription stop nucleotide position.
[5] Represents gene length in nucleotides (nt).
[6] Represents encoded protein length in amino acids (AA).
[7] The P gene is subjected to mRNA editing, whereby 2 extra G nucleotides are co-transcriptionally added between nucleotides 2439 and 2444.
[8] The V protein is encoded by the unedited P mRNA. The V open reading frame (ORF) starts at nt 1979 and ends at nt 2653; the encoded protein is 224 AA in length. The I protein is encoded by a modified P mRNA in which 4 G nucleotides are inserted between nucleotide positions 2439 and 2444. The I ORF starts at nt 1979 and ends at nt 2490; the encoded protein is 171 AA in length.

Insertion of a Single Gene into the Mumps Virus Genome

RESCUE OF MUMPS VIRUS FROM CDNA

This application is a National Stage entry of PCT/US00/21192 filed Aug. 2, 2000.

FIELD OF THE INVENTION

This invention relates to a method for recombinantly producing mumps virus, a nonsegmented, negative-sense, single-stranded RNA virus, and immunogenic compositions formed therefrom. Additional embodiments relate to methods of producing the mumps virus as an attenuated and/or infectious virus. The recombinant viruses are prepared from cDNA clones, and, accordingly, viruses having defined changes in the genome are obtained. This invention also relates to use of the recombinant virus formed therefrom as vectors for expressing foreign genetic information, e.g. foreign genes, for many applications, including immunogenic or pharmaceutical compositions for pathogens other than mumps, gene therapy, and cell targeting.

BACKGROUND OF THE INVENTION

Enveloped, negative-sense, single stranded RNA viruses are uniquely organized and expressed. The genomic RNA of negative-sense, single stranded viruses serves two template functions in the context of a nucleocapsid: as a template for the synthesis of messenger RNAs (mRNAs) and as a template for the synthesis of the antigenome (+) strand. Negative-sense, single stranded RNA viruses encode and package their own RNA-dependent RNA Polymerase. Messenger RNAs are only synthesized once the virus has entered the cytoplasm of the infected cell. Viral replication occurs after synthesis of the mRNAs and requires the continuous synthesis of viral proteins. The newly synthesized antigenome (+) strand serves as the template for generating further copies of the (−) strand genomic RNA.

The etiological agent of mumps was first shown reproducibly to be a virus by Johnson and Goodpasture in 1935 (Johnson and Goodpasture, 1935). Since then, propagation in tissue culture has facilitated virus classification and studies on the biological properties of mumps virus (MUV). Originally classified with influenza viruses in the Myxovirus family, mumps virus has since been re-assigned to the Paramyxoviridae family, subfamily Paramyxovirinae, genus Rubulavirus, based on nucleocapsid morphology, genome organization and biological properties of the proteins. Other examples of the Rubulavirus genus include simian virus 5 (SV5), human parainfluenza virus type 2 and type 4 and Newcastle disease virus (Lamb and Kolakofsky, 1996). Like all viruses of the Paramyxoviridae, mumps virus is pleomorphic in shape, comprising a host cell derived lipid membrane surrounding a ribonucleoprotein core; this nucleocapsid core forms a helical structure composed of a 15,384 nucleotide nonsegmented negative sense RNA genome closely associated with virus nucleocapsid protein (NP). The genetic organization of the MUV genome has been determined to be 3'-NP-P-M-F-SH-HN-L-5' (Elango et al., 1998). Each gene encodes a single protein except for the P cistron, from which three unique mRNAs are transcribed; one is a faithful copy of the P gene, encoding the V protein, the two other mRNAs contain two and four non-templated G residues inserted during transcription by a RNA editing mechanism, and encode the P and I proteins respectively (Paterson and Lamb, 1990). The P and L proteins in association with nucleocapsid form the functional RNA polymerase complex of mumps virus. The F and HN proteins are integral membrane proteins which project from the surface of the virion, and are involved in virus attachment and entry of cells. The small hydrophobic protein (SH) and matrix (M) protein are also membrane associated (Takeuchi et al, 1996 and Lamb and Kolakofsky, 1996); the role of the V and I proteins in virus growth is not yet clear.

The replicative cycle of mumps virus initiates upon fusion of virus envelope with host cell plasma membrane and subsequent release of virus nucleocapsid into the cell cytoplasm. Primary transcription then ensues, resulting in the production of all virus proteins; a switch to replication of the virus genome occurs later, followed by assembly of virus components to form new virus particles which bud from the host cell plasma membrane. Only the intact nucleocapsid structure can act as the template for RNA transcription, replication and subsequent virus amplification; therein lies the difficulty in genetic manipulation of MUV and other negative strand RNA viruses. Unlike the positive strand RNA viruses where naked genomic RNA is infectious and infectious virus can be recovered from a cDNA copy of the genome in the absence of additional viral factors (Taniguchi et al., 1978; Racaniello and Baltimore, 1981), the naked genome of negative strand RNA viruses is not infectious and rescue of virus from cDNA requires intracellular co-expression of viral NP, P and L proteins, along with a full length positive sense, or negative sense, genome RNA transcript, all under control of the bacteriophage T7 RNA polymerase promoter (Schnell et al., 1994; Lawson et al. 1995; Whelan et al., 1995; Radecke et al., 1995; Collins et al., 1995; Hoffman and Banerjee, 1997; Durbin et al., 1997; He et al., 1997; Baron and Barrett, 1997; Jin et al., 1998; Buchholz et al., 1999; Peeters et al., 1999). In all of the reported systems T7 RNA polymerase has been supplied either by a co-infecting recombinant vaccinia virus (Fuerst et al., 1986; Wyatt et al., 1995), or by endogenous expression of T7 RNA polymerase in a transformed cell line (Radecke et al., 1995).

The polymerase complex actuates and achieves transcription and replication by engaging the cis-acting signals at the 3' end of the genome, in particular, the promoter region. Viral genes are then transcribed from the genome template unidirectionally from its 3' to its 5' end. There is generally less mRNA made from the downstream genes (e.g., the polymerase gene (L)) relative to their upstream neighbors (i.e., the nucleoprotein gene (NP)). Therefore, there is always a gradient of mRNA abundance according to the position of the genes relative to the 3'-end of the genome.

Molecular genetic analysis of such nonsegmented RNA viruses has proved difficult until recently because naked genomic RNA or RNA produced intracellularly from a transfected plasmid is not infectious (Boyer and Haenni, 1994). These methods are referred to herein as "rescue". There are publications on methods of manipulating cDNA rescue methods that permit isolation of some recombinant nonsegmented, negative-strand RNA viruses (Schnell et al., 1994). The techniques for rescue of these different negative-strand viruses follows a common theme; however, each virus has distinguishing requisite components for successful rescue (Baron and Barrett, 1997; Collins et al., 1995; Garcin et al., 1995; Hoffman and Banerjee, 1997; Lawson et al., 1995; Radecke et al., 1995; Schneider et al., 1997; He et al, 1997; Schnell et al., 1994; Whelan et al., 1995). After transfection of a genomic cDNA plasmid, an exact copy of genome RNA is produced by the combined action of phage T7 RNA polymerase and a vector-encoded ribozyme sequence that cleaves the RNA to form the 3' termini. This RNA is packaged and replicated by viral proteins initially supplied by co-transfected expression plasmids. In the case of the mumps virus, a method of rescue has yet to be established and accordingly, there is a need to devise a method of mumps rescue. Devising a method of rescue for mumps virus is complicated by the absence of extensive studies on the biology of mumps virus, as compared with studies on other RNA viruses. Also, mumps virus does not grow efficiently in tissue culture systems. Furthermore, the sequence for the termini of the mumps virus genome has not previously been characterized in sufficient detail for conducting rescue.

For successful rescue of mumps virus from cDNA to be achieved, numerous molecular events must occur after transfection, including: 1) accurate, full-length synthesis of genome or antigenome RNA by T7 RNA polymerase and 3' end processing by the ribozyme sequence; 2) synthesis of viral NP, P, and L proteins at levels appropriate to initiate replication; 3) the de novo packaging of genomic RNA into transcriptionally-active and replication-competent nucleocapsid structures; and 4) expression of viral genes from newly-formed nucleocapsids at levels sufficient for replication to progress.

The present invention provides for a rescue method of recombinantly producing mumps virus. The rescued mumps virus possesses numerous uses, such as antibody generation, diagnostic, prophylactic and therapeutic applications, cell targeting, mutant virus preparation and immunogenic composition preparation. Furthermore, there are a number of advantages to using a recombinantly produced Jeryl Lynn strain of mumps for these applications. Some of these advantages include (1) an attenuated phenotype, (2) a substantial safety record based on the over 100 million dosages administered, (3) the ability to induce long-lasting immunity with a single dose and (4) a relatively low level of genome recombination.

SUMMARY OF THE INVENTION

The present invention provides for a method for producing a recombinant mumps virus comprising, in at least one host cell, conducting transfection of a rescue composition which comprises (i) a transcription vector comprising an isolated nucleic acid molecule which comprises a polynucleotide sequence encoding a genome or antigenome of a mumps virus and (ii) at least one expression vector which comprises at least one isolated nucleic acid molecule encoding the trans-acting proteins necessary for encapsidation, transcription and replication. The transfection is conducted under conditions sufficient to permit the co-expression of these vectors and the production of the recombinant virus. The recombinant virus is then harvested.

Additional embodiments relate to the nucleotide sequences, which upon mRNA transcription express one or more, or any combination of, the following proteins of the mumps virus: NP, M, F, SH, HN L and the V, P, and I proteins which are generated from the P "cistron" of mumps virus as noted above. Related embodiments relate to nucleic acid molecules which comprise such nucleotide sequences. A preferred embodiment of this invention are the nucleotide sequences of SEQ ID NOS. 1, 11 and 12. Further embodiments relate to these nucleotides, the amino acids sequences of the above mumps virus proteins and variants thereof.

The protein and nucleotide sequences of this invention possess diagnostic, prophylactic and therapeutic utility for mumps virus. These sequences can be used to design screening systems for compounds that interfere or disrupt normal virus development, via encapsidation, replication, or amplification. The nucleotide sequence can also be used in the preparation of immunogenic compositions for mumps virus and/or for other pathogens when used to express foreign genes. In addition, the foreign genes expressed may have therapeutic application.

In preferred embodiments, infectious recombinant virus is produced for use in immunogenic compositions and methods of treating or preventing infection by mumps virus and/or infection by other pathogens, wherein the method employs such compositions.

In alternative embodiments, this invention provides a method for generating recombinant mumps virus which is attenuated, infectious or both. The recombinant viruses are prepared from cDNA clones, and, accordingly, viruses having defined changes in the genome can be obtained. Further embodiments employ the consensus genome sequence and/or any of the genome sequences within the population of the Jeryl Lynn strain of mumps to express foreign genes since this licensed vaccine strain includes an established attenuated phenotype for safety. Since the consensus sequence is derived from a proposed average of the genomes of mumps virus, the polynucleotide sequences for the genomes within the population of the Jeryl Lynn strain are embodiments of this invention.

This invention also relates to use of the recombinant virus formed therefrom as vectors for expressing foreign genetic information, e.g. foreign genes, for many applications, including immunogenic compositions for pathogens other than mumps, gene therapy, and cell targeting.

The above-identified embodiments and additional embodiments, which are discussed in detail herein, represent the objects of this invention.

BRIEF DESCRIPTION OF THE FIGURES

FIG. 8 is a table (Table 1) that lists the nucleotide and amino acid differences between the full length cDNA clone and the plaque isolate 4 (PI4) and the consensus sequence for the Jeryl Lynn strain (SEQ ID NO. 1).

FIG. 9 is a table (Table 2) which describes a complete gene map for mumps virus, including the gene start and gene end for mumps virus proteins. The sequence of the 55 nucleotide long 3' leader and 24 nucleotide long 5' trailer are also shown.

FIG. 10 is a table (Table 3) that lists the mumps virus gene transcription start and stop nucleotide positions, along with the translation start and stop positions for the individual genes of the mumps genome as provided in SEQ ID NO 1. The nucleotides from each transcription (gene) start and to each stop nucleotide position in Table 3 correspond to nucleotide sequences for proteins NP, P, M, F, SH, HN and L (SEQ ID NOS 93-99, respectively).

BRIEF SUMMARY OF PRIMARY SEQUENCES

Figure 1:
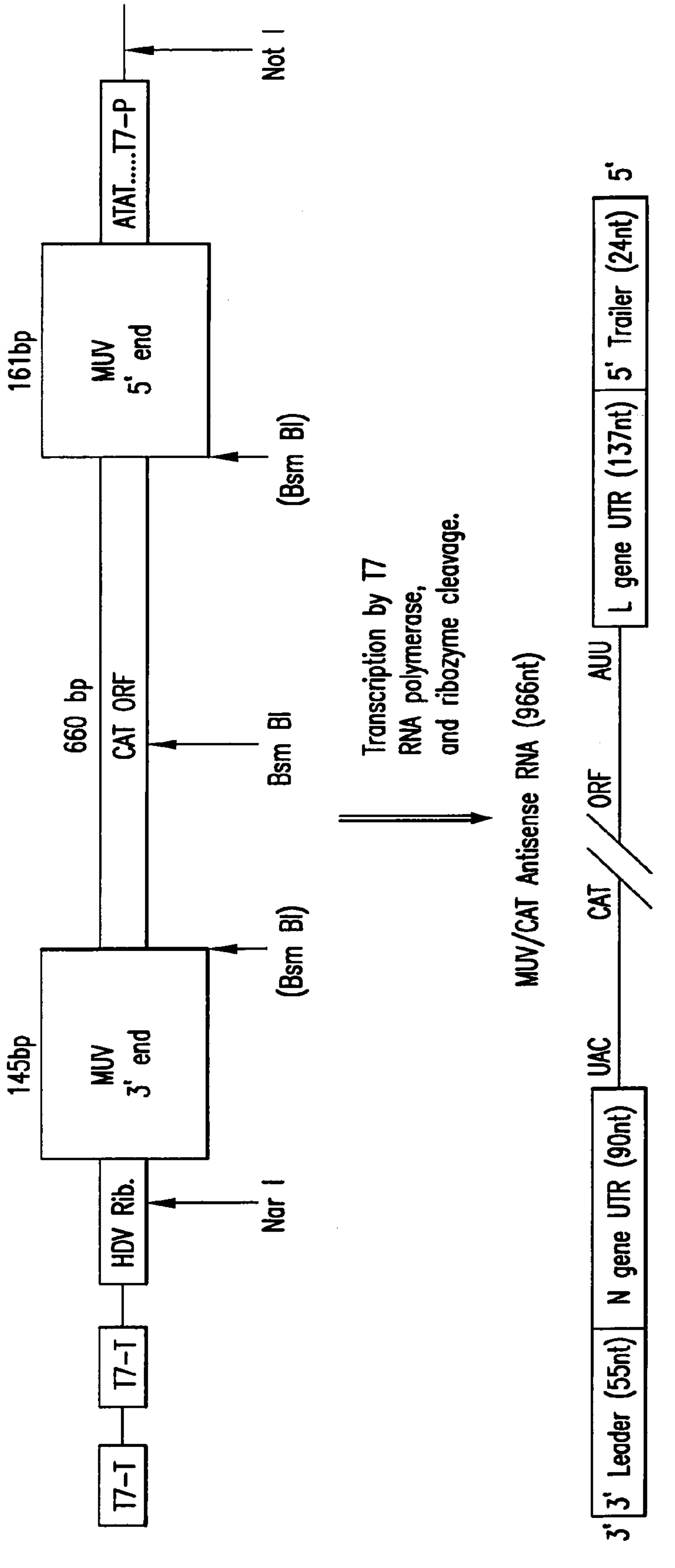
FIG. 1 depicts a diagram showing the organization of the MUVCAT minireplicon DNA construct and T7 RNA polymerase-transcribed minireplicon antisense RNA genome. Key restriction endonuclease sites utilized in the assembly of the DNA construct are shown. The T7 RNA polymerase promoter sequence was designed to start transcription with the exact MUV 5' terminal nucleotide, and a HDV ribozyme sequence was positioned to generate the precise MUV 3' terminal nucleotide in minireplicon RNA transcripts. Duplicate T7 RNA polymerase termination signals were included in tandem after the HDV ribozyme sequence. The CAT ORF replaces all of the coding and intercistronic sequence of the MUV genome; the remaining essential MUV specific sequence comprises the 3' MUV Leader (55 nt) with adjacent 90 nt NP gene untranslated region (UTR), and the 5' MUV Trailer (24 nt) adjacent to the 137 nt L gene UTR.

Sequence 1 is the consensus nucleotide sequence for the full-length genome for Jeryl Lynn strain of mumps virus. (SEQ ID NO. 1), which is written in the antigenomic (+, 5' to 3'), message sense.

Sequence 2 is the amino acid sequence of the mumps virus Jeryl Lynn strain NP protein. (SEQ ID NO. 2)

Sequence 3 is the amino acid sequence of the mumps virus Jeryl Lynn strain P protein. (SEQ ID NO 3)

Sequence 4 is the amino acid sequence of the mumps virus Jeryl Lynn strain I protein. (SEQ ID NO 4)

Sequence 5 is the amino acid sequence of the mumps virus Jeryl Lynn strain V protein. (SEQ ID NO 5)

Sequence 6 is the amino acid sequence of the mumps virus Jeryl Lynn strain M protein. (SEQ ID NO 6)

Sequence 7 is the amino acid sequence of the mumps virus Jeryl Lynn strain F protein. (SEQ ID NO 7)

Sequence 8 is the amino acid sequence of the mumps virus Jeryl Lynn strain SH protein. (SEQ ID NO 8)

Sequence 9 is the amino acid sequence of the mumps virus Jeryl Lynn strain HN protein. (SEQ ID NO 9)

Sequence 10 is the amino acid sequence of the mumps virus Jeryl Lynn strain L protein. (SEQ ID NO 10)

Sequence 11 is the complete nucleotide sequence of mumps Jeryl Lynn JL5 variant for plaque 2 (SEQ ID NO 11). Plaque 1 differed from plaque 2 at position 1703 (See Table 6). Sequence is written as DNA in antigenomic (+, 5' to 3') sense.

Sequence 12 is the complete nucleotide sequence of mumps Jeryl Lynn JL2 variant for plaque 2 (SEQ ID NO 12). Plaque 1 differs from plaque 2 at 5 nucleotide positions (See Table 7). Sequence is written as DNA in antigenomic (+, 5' to 3') sense.

DETAILED DESCRIPTION OF THE INVENTION

As noted above, the present invention relates to a method of producing recombinant mumps virus (MUV). Such methods in the art are referred to as "rescue" or reverse genetics methods. Several rescue methods for different nonsegmented, negative-strand viruses are disclosed in the following referenced publications: Baron and Barrett, 1997; Collins et al., 1995; Garcin et al., 1995; He et al., 1997; Hoffman and Banerjee, 1997; Lawson et al., 1995; Radecke and Billeter, 1997; Radecke et al., 1995; Schneider et al., 1997; Schnell, 1994; Whelan et al., 1995. Additional publications on rescue include published International patent application WO 97/06270 for MV and other viruses of the subfamily Paramyxovirinae, and for RSV rescue, published International patent application WO 97/12032.

Before conducting rescue of recombinant mumps virus, it was necessary to develop a consensus sequence for the entire mumps virus (Jeryl Lynn strain) and also develop a minireplicon rescue system for mumps virus (MUV). The consensus sequence is obtained by sampling the population of RNA genomes present during a mumps virus infection of a cell. Correspondingly, further embodiments of this invention relate to an isolated polynucleotide sequence encoding the genome or antigenome of mumps virus or proteins thereof, as well as variants of such sequences. Preferably, under high stringency conditions, these variant sequences hybridize to polynucleotides encoding one or more mumps proteins (See Table 2 of FIG. 9 for a complete map of the mumps virus, including the gene start and gene stop end for mumps virus proteins). More preferably, under high stringency conditions, these variant sequences hybridize to polynucleotides encoding one or more mumps virus strains, such as the polynucleotide sequences of SEQ ID NOS. 1, 11 and 12. For the purposes of defining high stringency southern hybridization conditions, reference can conveniently be made to Sambrook et al. (1989) at pp. 387-389 which is herein incorporated by reference, where the washing step at paragraph 11 is considered high stringency. This invention also relates to conservative variants wherein the polynucleotide sequence differs from a reference sequence through a change to the third nucleotide of a nucleotide triplet. Preferably these conservative variants function as biological equivalents to the mumps virus reference polynucleotide reference sequence. The "isolated" sequences of the present invention are non-naturally occurring sequences. For example, these sequences can be isolated from their normal state within the genome of the virus; or the sequences may be synthetic, i.e. generated via recombinant techniques, such as well-known recombinant expression systems, or generated by a machine.

This invention also relates to nucleic acid molecules comprising one or more of such polynucleotides. As noted above, a given nucleotide consensus sequence may contain one or more of the genomes within the population of a mumps virus, such as the Jeryl Lynn strain. Specific embodiments employ the consensus nucleotide sequence of SEQ ID. NOS 1, 11 or 12, or nucleotide sequences, which when transcribed, express one or more of the mumps virus proteins (NP, P/I/V, M, F, SH, HN and L). See Table 3 of FIG. 10 for the gene start, translation start, translation end, and gene end for these mumps virus proteins.

Further embodiments relate to the amino acid sequences for the mumps virus proteins NP, P/I/V, M, F, SH, HN and L as set forth in SEQ ID NOS. 2-10, respectively and also to fragments or variants thereof. Preferably, the fragments and variant amino acid sequences and variant nucleotide sequences expressing mumps virus proteins are biological equivalents, i.e. they retain substantially the same function of the proteins in order to obtain the desired recombinant mumps virus, whether attenuated, infectious or both. Such variant amino acid sequences are encoded by polynucleotides sequences of this invention. Such variant amino acid sequences may have about 70% to about 80%, and preferably about 90%, overall similarity to the amino acid sequences of the mumps virus protein. The variant nucleotide sequences may have either about 70% to about 80%, and preferably about 90%, overall similarity to the nucleotide sequences which, when transcribed, encode the amino acid sequences of the mumps virus proteins or a variant amino acid sequence of the mumps virus proteins. Exemplary nucleotide sequences for mumps virus proteins NP, P/I/V, M F, SH, HN and L are described in Tables 1 and 2 (of FIGS. 8 and 9, respectively).

The biological equivalents can be obtained by generating variants of the nucleotide sequence or the protein sequence. The variants can be an insertion, substitution, deletion or rearrangement of the template sequence. Variants of a mumps polynucleotide sequence can be generated by conventional methods, such as PCR mutagenesis, amino acid (alanine) screening, and site specific mutagenesis. The phenotype of the variant can be assessed by conducting a rescue with the variant to assess whether the desired recombinant mumps virus is obtained or the desired biological effect is obtained. The variants can also be assessed for antigenicity if the desired use is in an immunogenic composition.

Amino acid changes may be obtained by changing the codons of the nucleotide sequences. It is known that such changes can be obtained based on substituting certain amino acids for other amino acids in the amino acid sequence. For example, through substitution of alternative amino acids, small conformational changes may be conferred upon protein that may result in a reduced ability to bind or interact with other proteins of the mumps virus. Additional changes may alter the level of attenuation of the recombinant mumps virus.

One can use the hydropathic index of amino acids in conferring interactive biological function on a polypeptide, as discussed by Kyte and Doolittle (1982), wherein it was found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated is intended for use in immunological embodiments. See, for example, U.S. Pat. No. 4,554,101 (which is hereby incorporated herein by reference), which states that the greatest local average hydrophilicity of a "protein," as governed by the hydrophilicity of its adjacent amino acids, correlates with its immunogenicity. Accordingly, it is noted that substitutions can be made based on the hydrophilicity assigned to each amino acid.

In using either the hydrophilicity index or hydropathic index, which assigns values to each amino acid, it is preferred to introduce substitutions of amino acids where these values are ±2, with ±1 being particularly preferred, and those within ±0.5 being the most preferred substitutions.

Preferable characteristics of the mumps virus proteins, encoded by the nucleotide sequences of this invention, include one or more of the following: (a) being a membrane protein or being a protein directly associated with a membrane; (b) capable of being separated as a protein using an SDS acrylamide (10%) gel; and (c) retaining its biological function in contributing to the rescue and production of the desired recombinant mumps virus in the presence of other appropriate mumps virus proteins.

With the above nucleotide and amino acid sequences in hand, one can then proceed in rescuing mumps virus. Mumps rescue is achieved by conducting transfection, or transformation, of at least one host cell, in media, using a rescue composition. The rescue composition comprises (i) a transcription vector comprising an isolated nucleic acid molecule which comprises at least one polynucleotide sequence encoding a genome or antigenome of mumps virus and (ii) at least one expression vector which comprises one or more isolated nucleic acid molecule(s) encoding the trans-acting proteins necessary for encapsidation, transcription and replication; under conditions sufficient to permit the co-expression of said vectors and the production of the recombinant virus. By antigenome is meant an isolated positive message sense polynucleotide sequence which serves as the template for synthesis of progeny genome. Preferably, a polynucleotide sequence is a cDNA which is constructed to provide upon transcription a positive sense version of the mumps genome corresponding to the replicative intermediate RNA, or antigenome, in order to minimize the possibility of hybridizing with positive sense transcripts of complementing sequences encoding proteins necessary to generate a transcribing, replicating nucleocapsid. The transcription vector comprises an operably linked transcriptional unit comprising an assembly of a genetic element or elements having a regulatory role in the mumps expression, for example, a promoter, a structural gene or coding sequence which is transcribed into mumps RNA, and appropriate transcription initiation and termination sequences.

The transcription vector is co-expressed with mumps virus proteins, NP, P and L, which are necessary to produce nucleocapsid capable of RNA replication, and also render progeny nucleocapsids competent for both RNA replication and transcription. The NP, P and L proteins are generated from one or more expression vectors (e.g. plasmids) encoding the required proteins, although one, or one or more, of these required proteins may be produced within the selected host cell engineered to contain and express these virus-specific genes and gene products as stable transformants. In a preferred embodiment, NP, P and L proteins are expressed from an expression vector. More preferably, NP, P and L proteins are each expressed from separate expression vectors, such as plasmids. In the latter instance, one can more easily control the relative amount of each protein that is provided during transfection, or transformation. Additional mumps virus proteins may be expressed from the plasmids that express for NP, P or L, or the additional proteins can be expressed by using additional plasmids.

Although the amount of NP, P and L will vary depending on the tolerance of the host cell for their expression, the plasmids expressing NP, P and L are adjusted to achieve an effective molar ratio of NP, P and L, within the cell. The effective molar ratio is a ratio of NP, P and L that is sufficient to provide for successful rescue of the desired recombinant mumps virus. These ratios can be obtained based on the ratios of the expression plasmids as observed in minireplicon (CAT/reporter) assays. In one embodiment, the molecular ratio of transfecting plasmids pMUVNP: pMUVP is at least about 16:1 and pMUVP:pMUVL is at least about about 1:6. Preferably, the molecular ratio of pMUVNP: pMUVP is about 16:1 to about 4:1 and pMUVP:pMUVL is about 1:6 to about 1:1. More preferably, the ratio of pMUVNP: pMUVP is about 6:1 to about 5:1 and pMUVP:pMUVL is about 1:3 to about 1:2.

After transfection, or transformation, of a genomic cDNA plasmid along with mumps virus expression plasmids pMUVNP, pMUVP and pMUVL, an exact copy of genome RNA is produced by the combined action of phage T7 RNA polymerase and a vector-encoded ribozyme sequence that cleaves the RNA to form the 3' termini. This RNA is packaged and replicated by viral proteins initially supplied by co-transfected expression plasmids. In the case of the mumps virus rescue, a source that expresses T7 RNA polymerase is added to the host cell (or cell line), along with the source(s) for NP, P and L. Mumps rescue is achieved by co-transfecting this cell line with a mumps virus genomic cDNA clone containing an appropriately positioned T7 RNA polymerase promoter and expression plasmid(s) that encodes the mumps virus proteins NP, P and L.

For rescue of mumps, a cloned DNA equivalent of the desired viral genome is placed between a suitable DNA-dependent RNA polymerase promoter (e.g., the T7 RNA polymerase promoter) and a self-cleaving ribozyme sequence (e.g., the hepatitis delta ribozyme) which is inserted into a suitable transcription vector (e.g a bacterial plasmid). This transcription vector provides the readily manipulable DNA template from which the RNA polymerase (e.g., T7 RNA polymerase) transcribes a single-stranded RNA copy of the viral antigenome (or genome) with the precise, or nearly precise, 5' and 3' termini. The orientation of the viral genomic DNA copy and the flanking promoter and ribozyme sequences determines whether antigenome or genome RNA equivalents are transcribed.

Accordingly, in the rescue method a rescue composition is employed. The rescue composition can be varied as desired for a particular need or application. An example of a rescue composition is a composition which comprises (i) a transcription vector comprising an isolated nucleic acid molecule which comprises a polynucleotide sequence encoding a genome or antigenome of mumps virus and (ii) at least one expression vector which comprises at least one isolated nucleic acid molecule encoding the trans-acting proteins necessary for encapsidation, transcription and replication. The transcription and expression vectors are selected such that transfection of the rescue composition in a host cell results in the co-expression of these vectors and the production of the recombinant mumps virus.

As noted above, the isolated nucleic acid molecule comprises a sequence which encodes at least one genome or antigenome of a mumps virus. The isolated nucleic acid molecule may comprise a polynucleotide sequence which encodes a genome, antigenome or a modified version thereof. In one embodiment, the polynucleotide encodes an operably linked promoter, the desired genome or antigenome, a self-cleaving ribozyme sequence and a transcriptional terminator.

In a preferred embodiment of this invention, the polynucleotide encodes a genome or anti-genome that has been modified from a wild-type mumps virus by a nucleotide insertion, rearrangement, deletion or substitution. In preferred embodiments, the polynucleotide sequence encodes a cDNA clone for a recombinant mumps virus. It is submitted that the ability to obtain replicating virus from rescue may diminish as the polynucleotide encoding the native genome and antigenome is increasingly modified. The genome or antigenome sequence can be derived from that of any strain of mumps virus. The polynucleotide sequence may also encode a chimeric genome formed from recombinantly joining a genome or antigenome or genes from one or more heterologous sources.

Since the recombinant viruses formed by the methods of this invention can be employed as tools in diagnostic research studies or as therapeutic or prophylactic immunogenic compositions, the polynucleotide may also encode a wild type or an attenuated form of the mumps virus selected. In many embodiments, the polynucleotide encodes an attenuated, infectious form of the mumps virus. In particularly preferred embodiments, the polynucleotide encodes a genome or antigenome of a mumps virus having at least one attenuating mutation in the 3' genomic promoter region and having at least one attenuating mutation in the RNA polymerase gene, as described by published International patent application WO 98/13501, which is hereby incorporated by reference.

In addition to polynucleotide sequences encoding the modified forms of the desired mumps genome and antigenome as described above, the polynucleotide sequence may also encode the desired genome or antigenome along with one or more heterologous genes or a desired heterologous nucleotide sequence. These variants are prepared by introducing selected nucleotide sequences into a polynucleotide sequence encoding a genome or antigenome of mumps. Preferably, a desired heterologous sequence is inserted within an intergenic region of the mumps genome. However, the desired heterologous sequence can be inserted within a non-coding region of the mumps polynucleotide sequence, or inserted between a non-coding region and a coding region, or inserted at either end of the polynucleotide sequence. In alternative embodiments a desired heterologous sequence may be inserted within the coding region of a non-essential gene, or in place of the coding region for a non-essential gene. The insertion site choice can make use of the 3' to 5' gradient of expression of mumps virus. The heterologous nucleotide sequence (e.g. gene) can vary as desired. Depending on the application of the desired recombinant virus, the heterologous nucleotide sequence may encode a co-factor, cytokine (such as an interleukin), a T-helper epitope, a restriction marker, adjuvant, or a protein of a different microbial pathogen (e.g. virus, bacterium, fungus or parasite), especially proteins capable of eliciting a protective immune response. It may be desirable to select a heterologous sequence that encodes an immunogenic portion of a co-factor, cytokine (such as an interleukin), a T-helper epitope, a restriction marker, adjuvant, or a protein of a different microbial pathogen (e.g. virus, bacterium or fungus) in order to maximize the likelihood of rescuing the desired mumps virus, or minireplicon virus vector. Other types of non-mumps moieties include, but are not limited to, those from cancer cells or tumor cells, allergens amyloid peptide, protein or other macromolecular components. For example, in certain embodiments, the heterologous genes encode cytokines, such as interleukin-12, which are selected to improve the prophylatic or therapeutic characteristics of the recombinant virus.

Examples of such cancer cells or tumor cells include, but are not limited to, prostate specific antigen, carcino-embryonic antigen, MUC-1, Her2, CA-125 and MAGE-3.

Examples of such allergens include, but are not limited to, those described in U.S. Pat. No. 5,830,877 and published International Patent Application Number WO 99/51259, which are hereby incorporated by reference, and include pollen, insect venoms, animal dander, fungal spores and drugs (such as penicillin). Such components interfere with the production of IgE antibodies, a known cause of allergic reactions.

Amyloid peptide protein (APP) has been implicated in diseases referred to variously as Alzheimer's disease, amyloidosis or amyloidogenic disease. The β-amyloid peptide (also referred to as Aβ peptide) is a 42 amino acid fragment of APP, which is generated by processing of APP by the β and γ secretase enzymes, and has the following sequence:

Asp Ala Glu Phe Arg His Asp Ser Gly Tyr Glu Val His His Gln Lys Leu Val Phe Phe Ala Glu Asp Val Gly Ser Asn Lys Gly Ala Ile Ile Gly Leu Met Val Gly Gly Val Val Ile Ala (SEQ ID NO 97).

In some patients, the amyloid deposit takes the form of an aggregated Aβ peptide. Surprisingly, it has now been found that administration of isolated Aβ peptide induces an immune response against the Aβ peptide component of an amyloid deposit in a vertebrate host (See Published International Patent Application WO 99/27944). Such Aβ peptides have also been linked to unrelated moieties. Thus, the heterologous nucleotides sequences of this invention include the expression of this Aβ peptide, as well as fragments of Aβ peptide and antibodies to Aβ peptide or fragments thereof. One such fragment of Aβ peptide is the 28 amino acid peptide having the following sequence (As disclosed in U.S. Pat. No. 4,666,829)

Asp Ala Glu Phe Arg His Asp Ser Gly Tyr Glu Val His His Gln Lys Leu Val Phe Phe Ala Glu Asp Val Gly Ser Asn Lys (SEQ ID NO 98).

These heterologous sequences may be used in embodiments of this invention that relate to mumps virus vectors, which can be used to deliver varied RNAs, amino acid sequences, polypeptides and proteins to an animal or human. The examples set forth herein demonstrate the ability of mumps virus to express one or more heterologous genes (and even 3, 4, or 5 genes) under control of the mumps virus transcriptional promoter. In alternative embodiments, the additional heterologous nucleic acid sequence may be a single sequence of up to 7 to 10 kb, which is expressed as a single extra transcriptional unit. Preferably, the Rule of Six (Calain and Roux, 1993) is followed. In certain preferred embodiments this sequence may be up to 4 to 6 kb. One may also insert heterologous genetic information in the form of additional monocistronic transcriptional units, and polycistronic transcriptional units. Use of the additional monocistronic transcriptional units, and polycistronic transcriptional units should permit the insertion of more genetic information. In preferred embodiments, the heterologous nucleotide sequence is inserted within the mumps genome sequence as at least one polycistronic transcriptional unit, which may contain one or more ribosomal entry sites. In alternatively preferred embodiments, the heterologous nucleotide sequence encodes a polyprotein and a sufficient number of proteases that cleaves said polyprotein to generate the individual polypeptides of the polyprotein.

The heterologous nucleotide sequence can be selected to make use of the normal route of infection of mumps virus, which enters the body through the respiratory tract and can infect a variety of tissues and cells, for example, salivary glands, lymphoid tissue, mammary glands, the testes and even brain cells. The heterologous gene may also be used to provide agents which are used for gene therapy or for the targeting of specific cells. As an alternative to merely taking advantage of the normal cells exposed during the normal route of mumps infection, the heterologous gene, or fragment, may encode another protein or amino acid sequence from a different pathogen which, when employed as part of the recombinant mumps virus, directs the recombinant mumps virus to cells or tissue which are not in the normal route of mumps virus. In this manner, the recombinant mumps virus becomes a vector for the delivery of a wider variety of foreign genes.

For embodiments employing attenuated mumps viruses, conventional means are used to introduce attenuating mutations to generate a modified virus, such as chemical mutagenesis during virus growth in cell cultures to which a chemical mutagen has been added, followed by selection of virus that has been subjected to passage at suboptimal temperature in order to select temperature sensitive and/or cold adapted mutations, identification of mutant viruses that produce small plaques in cell culture, and passage through heterologous hosts to select for host range mutations. An alternative means of introducing attenuating mutations comprises making predetermined mutations using site-directed mutagenesis. One or more mutations may be introduced. These viruses are then screened for attenuation of their biological activity in cell culture and/or in an animal model. Attenuated mumps viruses are subjected to nucleotide sequencing to locate the sites of attenuating mutations.

A rescued recombinant mumps virus is tested for its desired phenotype (temperature sensitivity, cold adaptation, plaque morphology, and transcription and replication attenuation), first by in vitro means, such as sequence identification, confirmation of sequence tags, and antibody-based assays.

If the attenuated phenotype of the rescued virus is present, challenge experiments can be conducted with an appropriate animal model. Non-human primates provide the preferred animal model for the pathogenesis of human disease. These primates are first immunized with the attenuated, recombinantly-produced virus, then challenged with the wild-type form of the virus.

The choice of expression vector as well as the isolated nucleic acid molecule which encodes the trans-acting proteins necessary for encapsidation, transcription and replication can vary depending on the selection of the desired virus. The expression vectors are prepared in order to permit their co-expression with the transcription vector(s) in the host cell and the production of the recombinant virus under selected conditions.

A mumps rescue includes an appropriate cell milieu, preferably mammalian, in which T7 RNA polymerase is present to drive transcription of the antigenomic (or genomic) single-stranded RNA from the viral genomic cDNA-containing transcription vector. Either co-transcriptionally or shortly thereafter, this viral antigenome (or genome) RNA transcript is encapsidated into functional templates by the nucleocapsid protein and engaged by the required polymerase components produced concurrently from co-transfected expression plasmids encoding the required virus-specific trans-acting proteins. These events and processes lead to the prerequisite transcription of viral mRNAs, the replication and amplification of new genomes and, thereby, the production of novel viral progeny, i.e., rescue.

In the rescue method of this invention, a T7 RNA polymerase can be provided by recombinant vaccinia virus. This system, however, requires that the rescued virus be separated from the vaccinia virus by physical or biochemical means or by repeated passaging in cells or tissues that are not a good host for vaccinia virus. This requirement is avoided by using as a host cell restricted strain of vaccinia virus (e.g. MVA-T7) which does not proliferate in mammalian cells. Two recombinant MVAs expressing the bacteriophage T7 RNA polymerase have been reported. The MVA/T7 recombinant viruses contain one integrated copy of the T7 RNA polymerase under the regulation of either the 7.5K weak early/late promoter (Sutter et al., 1995) or the 11K strong late promoter (Wyatt et al., 1995).

The host cell, or cell line, that is employed in the transfection of the rescue composition can vary widely based on the conditions selected for rescue. The host cells are cultured under conditions that permit the co-expression of the vectors of the rescue composition so as to produce the desired recombinant mumps virus. Such host cells can be selected from a wide variety of cells, including eukaryotic cells, and preferably vertebrate cells. Avian cells may be used, but preferred host cells are derived from a human cell, such as a human embryonic kidney cell. Exemplary host cells are human 293 cells, A549 cells and Hep2 cells. Vero cells as well as many other types of cells can also be used as host cells. Other examples of suitable host cells are: (1) Human Diploid Primary Cell Lines: e.g. WI-38 and MRC5 cells; (2) Monkey Diploid Cell Line: e.g. FRhL—Fetal Rhesus Lung cells; (3) Quasi-Primary Continuous Cell Line: e.g. AGMK—African green monkey kidney cells.; (4) other potential cell lines, such as, CHO, MDCK (Madin-Darby Canine Kidney), and primary chick embryo fibroblasts (CEF). Some eukaryotic cell lines are more suitable than others for propagating viruses and some cell lines do not work at all for some viruses. A cell line is employed that yields detectable cytopathic effect in order that rescue of viable virus may be easily detected. In the case of mumps, the transfected cells can be co-cultured on Vero cells because the virus spreads rapidly on Vero cells and makes easily detectable plaques. In general, a host cell which is permissive for growth of the selected virus is employed.

In alternatively preferred embodiments, a transfection-facilitating reagent may be added to increase DNA uptake by cells. Many of these reagents are known in the art. LIPOFECTACE (Life Technologies, Gaithersburg, Md.) and EFFECTENE (Qiagen, Valencia, Calif.) are common examples. Lipofectace and Effectene are both cationic lipids. They both coat DNA and enhance DNA uptake by cells. Lipofectace forms a liposome that surrounds the DNA while Effectene coats the DNA but does not form a liposome.

The transcription vector and expression vector can be plasmid vectors designed for expression in the host cell. The expression vector which comprises at least one isolated nucleic acid molecule encoding the trans-acting proteins necessary for encapsidation, transcription and replication may express these proteins from the same expression vector or at least two different vectors. These vectors are generally known from the basic rescue methods, and they need not be altered for use in the improved methods of this invention.

In the method of the present invention, a standard temperature range (about 32° C. to about 37° C.) for rescue can be employed; however, the rescue at an elevated temperature has been shown to improve recovery of the recombinant RNA virus. The elevated temperature is referred to as a heat shock temperature (See Published International Patent Application Number WO 99/63064, which is hereby incorporated herein by reference). An effective heat shock temperature is a temperature above the standard temperature suggested for performing rescue of a recombinant virus at which the level of recovery of recombinant virus is improved. An exemplary list of temperature ranges is as follows: from 38° C. to about 47° C., with from about 42°

C. to about 46° C. being the more preferred. Alternatively, it is noted that heat shock temperatures of 43° C., 44° C., and 45° C. are particularly preferred.

Numerous means are employed to determine the level of recovery of the desired recombinant mumps virus. As noted in the examples herein, a chloramphenicol acetyl transferase (CAT) reporter gene is used to monitor and optimize conditions for rescue of the recombinant virus. The corresponding activity of the reporter gene establishes the baseline and test level of expression of the recombinant virus. Other methods include detecting the number of plaques of recombinant virus obtained and verifying production of the rescued virus by sequencing.

In preferred embodiments, the transfected rescue composition, as present in the host cell(s), is subjected to a plaque expansion step (i.e. amplification step). The transfected rescue composition is transferred onto at least one layer of plaque expansion cells (PE cells). The recovery of recombinant virus from the transfected cells is improved by selecting a plaque expansion cell in which the mumps virus or the recombinant mumps virus exhibits enhanced growth. Preferably, the transfected cells containing the rescue composition are transferred onto a monolayer of substantially confluent PE cells. The various modifications for rescue techniques, including plaque expansion, are also set forth in Published International Patent Application Number WO 99/63064.

The recombinant mumps viruses prepared from the methods of the present invention are employed for diagnostic, prophylactic and therapeutic applications. Preferably, the recombinant viruses prepared from the methods of the present invention are attenuated. The attenuated recombinant virus should exhibit a substantial reduction of virulence compared to the wild-type virus which infects human and animal hosts. The extent of attenuation is such that symptoms of infection will not arise in most individuals, but the virus will retain sufficient replication competence to be infectious and elicit the desired immune response profile for vaccines. The attenuated recombinant virus can be used alone or in conjunction with pharmaceuticals, antigens, immunizing agents or adjuvants, as vaccines in the prevention or amelioration of disease. These active agents can be formulated and delivered by conventional means, i.e. by using a diluent or pharmaceutically acceptable carrier.

Accordingly, in further embodiments of this invention attenuated recombinantly produced mumps virus is employed in immunogenic compositions comprising (i) at least one recombinantly produced attenuated mumps virus and (ii) at least one of a pharmaceutically acceptable buffer or diluent, adjuvant or carrier. Preferably, these compositions have therapeutic and prophylactic applications as immunogenic compositions in preventing and/or ameliorating mumps infection. In such applications, an immunologically effective amount of at least one attenuated recombinant mumps virus of this invention is employed in such amount to cause a substantial reduction in the course of the normal mumps infection.

The formulation of such immunogenic compositions is well known to persons skilled in this field. Immunogenic compositions of the invention may comprise additional antigenic components (e.g., polypeptide or fragment thereof or nucleic acid encoding an antigen or fragment thereof) and, preferably, include a pharmaceutically acceptable carrier. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The term "pharmaceutically acceptable carrier" refers to a carrier that does not cause an allergic reaction or other untoward effect in patients to whom it is administered. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antigen. The use of such media and agents for pharmaceutically active substances is well known in the art. Except insofar as any conventional media or agent is incompatible with the active ingredient, use thereof in immunogenic compositions of the present invention is contemplated.

Administration of such immunogenic compositions may be by any conventional effective form, such as intranasally, parenterally, orally, or topically applied to mucosal surface such as intranasal, oral, eye, lung, vaginal, or rectal surface, such as by aerosol spray. The preferred means of administration is parenteral or intranasal.

Oral formulations include such normally employed excipients as, for example, pharmaceutical grades of mannitol, lactose, starch, magnesium stearate, sodium saccharine, cellulose, magnesium carbonate, and the like.

The vaccine compositions of the invention can include an adjuvant, including, but not limited to aluminum hydroxide; aluminum phosphate; Stimulon™ QS-21 (Aquila Biopharmaceuticals, Inc., Framingham, Mass.); MPL™ (3-O-deacylated monophosphoryl lipid A; RIBI ImmunoChem Research, Hamilton, Mont.), IL-12 (Genetics Institute, Cambridge, Mass.); N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphos-phoryloxy)-ethylamine (CGP 19835A, referred to a MTP-PE); and cholera toxin. Others which may be used are non-toxic derivatives of cholera toxin, including its B subunit (for example, wherein glutamic acid at amino acid position 29 is replaced by another amino acid, preferably, a histidine in accordance with Published International Patent Application WO 00/18434, which is hereby incorporated herein), and/or conjugates or genetically engineered fusions of non-mumps polypeptides with cholera toxin or its B subunit, procholeragenoid, fungal polysaccharides.

The recombinantly produced attenuated mumps virus of the present invention may be administered as the sole active immunogen in an immunogenic composition. Alternatively, however, the immunogenic composition may include other active immunogens, including other immunologically active antigens against other pathogenic species. The other immunologically active antigens may be replicating agents or non-replicating agents. Replicating agents include, for example, attenuated forms of measles virus, rubella virus, variscella zoster virus (VZV), Parainfluenza virus (PIV), and Respiratory Syncytial virus (RSV).

One of the important aspects of this invention relates to a method of inducing immune responses in a mammal comprising the step of providing to said mammal an immunogenic composition of this invention. The immunogenic composition is a composition which is immunogenic in the treated animal or human such that the immunologically effective amount of the polypeptide(s) contained in such composition brings about the desired response against mumps infection. Preferred embodiments relate to a method for the treatment, including amelioration, or prevention of mumps infection in a human comprising administering to a human an immunologically effective amount of the immunogenic composition. The dosage amount can vary depending upon specific conditions of the individual. This amount can be determined in routine trials by means known to those skilled in the art.

Certainly, the isolated amino acid sequences for the proteins of the mumps virus may be used in forming subunit vaccines. They may also be used as antigens for raising polyclonal or monoclonal antibodies and in immunoassays for the detection of anti-mumps virus protein-reactive antibodies. Immunoassays encompassed by the present invention include, but are not limited to those described in U.S. Pat. No. 4,367,110 (double monoclonal antibody sandwich assay) and U.S. Pat. No. 4,452,901 (western blot), which U.S. patents are incorporated herein by reference. Other assays include immunoprecipitation of labeled ligands and immunocytochemistry, both in vitro and in vivo.

This invention also provides for a method of diagnosing a mumps infection, or identifying a mumps vaccine strain that has been administered, comprising the step of determining the presence, in a sample, of an amino acid sequence of SEQ ID NOS 2-10. Any conventional diagnostic method may be used. These diagnostic methods can easily be based on the presence of an amino acid sequence or polypeptide. Preferably, such a diagnostic method matches for a polypeptide having at least 10, and preferably at least 20, amino acids which are common to the amino acid sequences of this invention.

The nucleic acid sequences disclosed herein can also be used for a variety of diagnostic applications. These nucleic acids sequences can be used to prepare relatively short DNA and RNA sequences that have the ability to specifically hybridize to the nucleic acid sequences encoding the mumps virus proteins. Nucleic acid probes are selected for the desired length in view of the selected parameters of specificity of the diagnostic assay. The probes can be used in diagnostic assays for detecting the presence of pathogenic organisms, or in identifying a mumps vaccine that has been administered, in a given sample. With current advanced technologies for recombinant expression, nucleic acid sequences can be inserted into an expression construct for the purpose of screening the corresponding oligopeptides and polypeptides for reactivity with existing antibodies or for the ability to generate diagnostic or therapeutic reagents. Suitable expression control sequences and host cell/cloning vehicle combinations are well known in the art, and are described by way of example, in Sambrook et al. (1989).

In preferred embodiments, the nucleic acid sequences employed for hybridization studies or assays include sequences that are complementary to a nucleotide stretch of at least about 10 to about 20 nucleotides, although at least about 10 to 30, or about 30 to 60 nucleotides can be used. A variety of known hybridization techniques and systems can be employed for practice of the hybridization aspects of this invention, including diagnostic assays such as those described in Falkow et al., U.S. Pat. No. 4,358,535.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., amniotic fluid, middle ear effusion, bronchoalveolar lavage fluid) or even tissues, is absorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, et.). Following washing of the hybridized surface so as to remove nonspecifically bound probe molecules, specific hybridization is detected, or even quantified, by means of the label.

The nucleic acid sequences which encode the mumps virus proteins of the invention, or their variants, may be useful in conjunction with PCR™ technology, as set out, e.g., in U.S. Pat. No. 4,603,102. One may utilize various portions of any of mumps virus sequences of this invention as oligonucleotide probes for the PCR™ amplification of a defined portion of a mumps virus gene, or mumps virus nucleotide, which sequence may then be detected by hybridization with a hybridization probe containing a complementary sequence. In this manner, extremely small concentrations of mumps nucleic acid may be detected in a sample utilizing the nucleotide sequences of this invention.

The following examples are included to illustrate certain embodiments of the invention. However, those of skill in the art should, in the light of the present disclosure, appreciate that many changes can be made in the specific embodiments which are disclosed and still obtain a like or similar result without departing from the spirit and scope of the invention.

The following examples are provided by way of illustration, and should not be construed as limitative of the invention as described hereinabove.

EXAMPLES

Example 1

Materials and Methods

Cells and viruses. Primary chick embryo fibroblast (CEF) cells were obtained from SPAFAS Inc., Preston, Conn.), and cultured in Eagle's Basal Medium (BME) supplemented with 5% fetal calf serum. Hep 2 cells, 293 cells, A549, and Vero cells were obtained from the American Type Culture Collection (ATCC) and grown in Dulbecco's Modified Eagle Medium (DMEM) supplemented with 10% fetal calf serum. The Jeryl Lynn strain of mumps virus was cultured directly on CEF cells from a vial of Mumpsvax®, Lot Numbers 0089E, 0656J, and 1159H (Merck and Co., Inc., West Point, Pa.). Recombinant vaccinia virus Ankara (MVA-T7), expressing bacteriophage T7 RNA polymerase was obtained from Dr. B. Moss [(National Institutes of Health, Bethesda, Md.), see Wyatt et al., 1995].

1.A. Generation of Mumps Virus Jeryl Lynn Consensus Sequence.

Growth of mumps virus Jeryl Lynn strain stock. Mumps virus Jeryl Lynn strain was cultured directly from vials of Mumpsvax (lot # 1159H, Merck and Co., Inc.) on primary chick embryo fibroblasts (CEFs, Spafas, Inc.) in Dulbecco's Modified Eagle Medium (DMEM) supplemented with 5% fetal calf serum or in Eagle's Basal Medium (BME) supplemented with 5% fetal calf serum. CEFs plated on T-75 flasks were infected with resuspended Mumpsvax at an approximate multiplicity of infection (moi) of 0.002 for 2 hours at room temperature. The inoculum was removed from the cells and replaced with fresh media. Cells were incubated at 37° C. for 4 days, at which time extensive syncytia and cytopathology was observed. Virus was collected by scraping the cells into the culture media, followed by freeze-thawing twice in a dry ice/ethanol bath followed by incubation at 37° C. Cell debris was removed by centrifugation at 2,500 rpm in a Beckman GS-6KR centrifuge (Beckman Instruments, Inc., Palo Alto, Calif.). Virus was stored at −80° C.

Isolation of Viral RNA, Amplification, and Sequencing.

Mumps viral RNA was isolated from frozen aliquots of virus using Trizol LS Reagent according to the manufacturer (GibcoBRL, Grand Island, N.Y.). Reverse transcription followed by polymerase chain reaction (RT-PCR) was performed using the isolated viral RNA as a template and using the Titan One-Tube RT-PCR System (Boehringer Mannheim, Indiananpolis, Ind.). The mumps genome was amplified in four separate fragments, using the following primer pairs:

5'-$_{1}$ACCAAGGGGAGAATGAATATGGG$_{23}$ (SEQ ID NO. 95) and

5'-$_{3875}$CTGAACTGCTCTTACTAATCTGGAC$_{3851}$ (SEQ ID NO. 82) (3.9 kb product);

5'-$_{3773}$CTGTGTTACATTCTTATCTGTGACAG$_{3798}$ (SEQ ID NO. 21) and

5'-$_{7783}$TGTAACTAGGATCTGATTCCAAGC$_{7760}$ (SEQ ID NO. 72) (4 kb product);

5'-$_{7678}$AGAGTTAGATCAGCGTGCTTTGAG$_{7701}$ (SEQ ID NO. 32) and

5'-$_{11685}$CCTTGGATCTGTTTTCTTCTACCG$_{11662}$ (SEQ ID NO. 62) (4 kb product);

5'-$_{11529}$GTGTTAATCCCATGCTCCGTGGAG$_{11552}$ (SEQ ID NO. 42) and

5'-$_{15384}$ACCAAGGGGAGAAAGTAAAATC$_{15363}$ (SEQ ID NO. 53) (3.9 kb product). The suggested protocol from the manufacturer (Boehringer Mannheim, Indiananpolis, Ind., catalog # 1855476) was followed for the RT and PCR conditions. The PCR products were purified on a 1% agarose gel.

The PCR products were sequenced using an Applied Biosystems (ABI) 377 Sequencer (Applied Biosystems, Inc., Foster City, Calif.). For sequencing purposes, a series of primers was designed which spanned the entire mumps genome as shown in Table 4 below. These primer sequences were based on nucleotide sequence information obtained from Genbank for a varying combination of incompletely sequenced mumps virus strains. Using the published sequences, a hypothetical mumps genome sequence was devised encoding its proteins and then the primers were generated therefrom.

In order to determine properly the sequences at the 5' and 3' ends of the mumps virus Jeryl Lynn genome, viral genome RNA was ligated at its ends and cDNA was then amplified by PCR across the ligated region. For each reaction, 3-5 μg viral RNA was incubated in 10% DMSO, 5× ligation buffer and deionized water at 83° C. for 3 minutes to denature any secondary structures, and then placed immediately on ice. T4 RNA ligase (20 Units, New England Biolabs, Inc., Beverly, Mass.) and 40 Units of RNasin (Promega) were added to give a final ligation mixture of 20 μl which was incubated overnight at 16° C. The ligation products were phenol/chloroform-extracted and subjected to RT-PCR using the following primer pair which spanned the ligated region of the genome:

5'-$_{15166}$GCGCATTGATATTGACAATGI$_{15185}$ (SEQ ID NO. 52) and

5'-$_{216}$CCCTCCTCACCCCTGTCTTG$_{197}$ (SEQ ID NO. 92) The PCR products were subjected to a second round of PCR using the following nested primers:

5'-$_{15227}$GAATAAAGACTCTTCTGGC$_{15245}$ (SEQ ID NO. 93) and 5'-$_{138}$GGTAGTGTCAAAATGCCCCC$_{119}$ (SEQ ID NO. 94). The final PCR products were gel-purified and sequenced.

Table 4

Primers for sequencing MUV genome $_{1}$ACCAAGGGGAGAATGAATATGGG$_{23}$ (SEQ ID NO: 95)

$_{385}$CTCAGCAGGCATGCAAAATC$_{404}$ (SEQ ID NO: 96)

$_{765}$CAAGATACATGCTGCAGCCG$_{784}$ (SEQ ID NO: 13)

$_{1169}$GTCCTAGATGTCCAAATGCG$_{1188}$ (SEQ ID NO: 14)

$_{1544}$GACTTTAGAGCACAGCCTTT$_{1563}$ (SEQ ID NO: 15)

$_{1841}$CAATCTAGCCACAGCTAACT$_{1861}$ (SEQ ID NO: 16)

$_{2107}$CGTTGCACCAGTACTCATTG$_{2126}$ (SEQ ID NO: 17)

$_{2484}$GGCATAGACGGGAATGGAGC$_{2503}$ (SEQ ID NO: 18)

$_{3072}$TTCGAGCAACGATTGGCAAAGGC$_{3094}$ (SEQ ID NO: 19)

$_{3712}$CCAGCTCCGATAAATATGTC$_{3731}$ (SEQ ID NO: 20)

$_{3773}$CTGTGTTACATTCTTATCTGTGACAG$_{3798}$ (SEQ ID NO: 21)

$_{4062}$CTGACAGTCAGCATAGGAGA$_{4081}$ (SEQ ID NO: 22)

$_{4364}$GAAGTCTGCCTCAATGAGAA$_{4383}$ (SEQ ID NO: 23)

$_{4716}$CCAACCCACTGATAACAGCT$_{4735}$ (SEQ ID NO: 24)

$_{5185}$CCAGCATTGTCACCGATTAG$_{5204}$ (SEQ ID NO: 25)

$_{5545}$CAATACAATGAGGCAGAGAG$_{5564}$ (SEQ ID NO: 26)

$_{6223}$TGAATCTCCTAGGGTCGTAACGTC$_{6246}$ (SEQ ID NO: 27)

$_{5952}$GAGCAACCATCAGCTCCAAT$_{5971}$ (SEQ ID NO: 28)

$_{6330}$CATAACCCTGTATGTCTGGAC$_{6350}$ (SEQ ID NO: 29)

$_{6783}$GGATGATCAATGATCAAGGC$_{6802}$ (SEQ ID NO: 30)

$_{7172}$GGTAAGACACACTGGTGCTA$_{7191}$ (SEQ ID NO: 31)

$_{7678}$AGAGTTAGATCAGCGTGCTTTGAG$_{7701}$ (SEQ ID NO: 32)

$_{7887}$GCTGGTGGCCGTATGAACTCC$_{7907}$ (SEQ ID NO: 33)

$_{8344}$CAGATTGACCATCACTTGAG$_{8363}$ (SEQ ID NO: 34)

$_{8660}$CCTAGTCTCCGGTGGACCCG $_{8679}$ (SEQ ID NO: 35)

$_{9166}$CACTGATATGTTAGAGGGAC$_{9185}$ (SEQ ID NO: 36)

$_{9583}$CCGAGAGTCCATGTGTGCTC$_{9602}$ (SEQ ID NO: 37)

$_{10000}$AGAGGATGACAGATTCGATC$_{10019}$ (SEQ ID NO: 38)

$_{10415}$GAGATAGCAGCCTGCTTTCT$_{10434}$ (SEQ ID NO: 39)

$_{10813}$GCTCAGTCATTCCGAGAAGA$_{10832}$ (SEQ ID NO: 40)

$_{11193}$GTCAGGACATCACTAATGCT$_{11212}$ (SEQ ID NO: 41)

$_{11529}$GTGTTAATCCCATGCTCCGTGGAG$_{11552}$ (SEQ ID NO: 42)

$_{12006}$GCAGTAGTGGTGATGACAAG$_{12025}$ (SEQ ID NO: 43)

$_{12375}$CTCCTATGCATTCTCTAGCT$_{12395}$ (SEQ ID NO: 44)

$_{12793}$GCAGATGGTAAATAGCATCA$_{12812}$ (SEQ ID NO: 45)

$_{13219}$CGATTATGAGATAGTTGTTC$_{13238}$ (SEQ ID NO: 46)

$_{13623}$GTTCATCCGAATCAGCATCC$_{13642}$ (SEQ ID NO: 47)

$_{14036}$CAAGCAGGTATAGCAGCAGG$_{14055}$ (SEQ ID NO: 48)

$_{4388}$CCGACCCGAATAATCACGAG$_{14407}$ (SEQ ID NO: 49)

$_{4775}$CATCAGATCATGACACCCTA$_{14794}$ (SEQ ID NO: 50)

$_{14963}$GTGATAACACCCATGGAGATTC$_{14984}$ (SEQ ID NO: 51)

$_{15166}$GCGCATTGATATTGACAATG$_{15185}$ (SEQ ID NO: 52)

$_{15384}$ACCAAGGGGAGAAAGTAAAATC$_{15363}$ (SEQ ID NO: 53)

$_{14977}$CATGGGTGTTATCACGTCTC$_{14958}$ (SEQ ID NO: 54)

$_{14549}$CAACACGCCTCCTCCAGTAC$_{14530}$ (SEQ ID NO: 55)

$_{14201}$GTACACCCTCCAGATCCACA$_{14182}$ (SEQ ID NO: 56)

$_{13807}$CCATGATGTGGATGATAAAC$_{13788}$ (SEQ ID NO: 57)

$_{13412}$CATATTCGACAGTTTGGAGT$_{13393}$ (SEQ ID NO: 58)

$_{13021}$CAAGGTCATATACACATAGT$_{13002}$ (SEQ ID NO: 59)

$_{12602}$CTACACAAGACTCGACAGGT$_{12583}$ (SEQ ID NO: 60)

$_{12197}$CTCCCGCTAATCTGAGTGCT$_{12178}$ (SEQ ID NO: 61)

$_{11685}$CCTTGGATCTGTTTTCTTCTACCG$_{11662}$ (SEQ ID NO: 62)

$_{11382}$CAGATATCTAGACAGCCAGC$_{11363}$ (SEQ ID NO: 63)

$_{11017}$GCACATCTTGCTCACGTTCT$_{10998}$ (SEQ ID NO: 64)

$_{10610}$GGGTAGGATCTGATGGAGGA$_{10591}$ (SEQ ID NO: 65)

$_{10122}$CGACCTGTAGCCTTTATCTC$_{10103}$ (SEQ ID NO: 66)

$_{9753}$TCATGCCGCATCTCAATGAG$_{9734}$ (SEQ ID NO: 67)

$_{9356}$CACCATACTGTAATTGGGCG$_{9337}$ (SEQ ID NO: 68)

$_{8969}$ACCCACTCCACTCATTGTTGAACC$_{8946}$ (SEQ ID NO: 69)

$_{8602}$TTCAGCTCGAATTGCCTTCC$_{8583}$ (SEQ ID NO: 70)

$_{8461}$GAGTATCTCATTTAGGCCCG$_{8442}$ (SEQ ID NO: 71)

$_{7783}$TGTAACTAGGATCTGATTCCAAGC$_{7760}$ (SEQ ID NO: 72)

$_{7756}$GACAAGAAATGCACTCTGTA$_{7737}$ (SEQ ID NO: 73)

$_{7325}$CATCACTGAGATATTGGATC$_{7306}$ (SEQ ID NO: 74)

$_{6909}$GATACCGTTACTCCGTGAAT$_{6980}$ (SEQ ID NO: 75)

$_{6347}$CAGACATACAGGGTTATGATGAG$_{6325}$ (SEQ ID NO: 76)

$_{5753}$GTGACTGCATGATGGTCAGG$_{5734}$ (SEQ ID NO: 77)

$_{5352}$CATCTGCATCTCATCTAGCA$_{5333}$ (SEQ ID NO: 78)

$_{4951}$CACGTGCATTCGTCTGTGCT$_{4932}$ (SEQ ID NO: 79)

$_{4589}$GAAAAGATTGCATAGCCCAAGC$_{4568}$ (SEQ ID NO: 80)

$_{4256}$CTGGAGAATAGCACTGGCAG$_{4237}$ (SEQ ID NO: 81)

$_{3875}$CTGAACTGCTCTTACTAATCTGGAC$_{3851}$ (SEQ ID NO: 82)

$_{3530}$GCACGCTGTCACTACAGGAG$_{3511}$ (SEQ ID NO: 83)

$_{3158}$GTGAGTTCATATGGCGCTTC$_{3139}$ (SEQ ID NO: 84)

$_{2767}$GCTAGTGTTGTCTTTACTGT$_{2748}$ (SEQ ID NO: 85)

$_{2507}$TGAGGCTCCATTCCCGTCTATG$_{2486}$ (SEQ ID NO: 86)

$_{2334}$GTTGGTTGGATAGTTGGATC$_{2315}$ (SEQ ID NO: 87)

$_{1780}$GCCCACTTGCGACTGTGCGT$_{1761}$ (SEQ ID NO: 88)

$_{1438}$CTCATATGCGGCAGCAGGTT$_{1419}$ (SEQ ID NO: 89)

$_{1039}$GGATCGGAGCTTAGTGAGTT$_{1020}$ (SEQ ID NO: 90)

$_{656}$GTACACTGTAACACCGATCC$_{637}$ (SEQ ID NO: 91)

$_{216}$CCCTCCTCACCCCTGTCTTG$_{97}$ (SEQ ID NO:92)

Prior work had shown that the Jeryl Lynn vaccine strain contained a mixture of two distinct virus populations (Afzal et al., 1993). Therefore in order to minimize the potential for sub-optimal protein-protein interactions (by splicing together cDNA fragments derived from the different virus populations into the genome cDNA) during the rescue process, a well isolated plaque from the Jeryl Lynn vaccine preparation (designated as plaque isolate 4, PI 4) was selected and amplified for the derivation of the full length genome cDNA, and the NP, P and L expression plasmids.

1.B Construction of expression plasmids for MUV NP, P and L proteins. Expression plasmids for the MUV NP, P and L proteins (pMUVNP, pMUVP, pMUVL) were constructed by splicing cDNA for each ORF between the T7 RNA polymerase promoter and the T7 RNA polymerase transcription termination sequence of a modified plasmid vector pEMC (Moss et al., 1990) which contained the cap independent translation enhancer (CITE) of encephalo-myocarditis virus (EMC). The primers used for RT-PCR amplification of the MUV NP protein ORF, from total MUV infected-cell (CEF) RNA, were 5' CGTCTC CCATGT-TGTCTGTGCTCAAAGC (SEQ ID NO 99) and 5' ATCAT-TCTCGAG TTGCGATTGGGGTTAGTTTG (SEQ ID NO 100); the resulting cDNA fragment was gel purified, trimmed with BsmBI and XhoI, and then ligated into NcoI/XhoI cut pEMC, such that the AUG of the NP protein ORF was adjacent to the CITE. Primers for the amplification of the MUV P ORF were 5' TTCCGGGCAAGCCATGGATC (SEQ ID NO 101) and 5' ATCATTCTC GAGAGGGAAT-CATTGTGGCTCTC (SEQ ID NO 102). The P ORF cDNA (modified by site-directed mutagenesis to include the two G nucleotides which are co-transcriptionally inserted by viral polymerase to generate P mRNA) was also cloned into the NcoI/XhoI sites of pEMC. Because of it's large size the L protein ORF was assembled in two steps; primers 5' ATCAT-TCGTCTCCCATGGCGGGCCTAAATGAGATACTC (SEQ ID NO 103) and 5'CTTCGTTCA TCTGTTTTG-GATCCG (SEQ ID NO 104) were used in the first step to produce a cDNA fragment which was trimmed with BsmBI and BamHI, then cloned into the NcoI/BamHI sites of pEMC. In the second step primers 5' CAGAGT ACCTTATATCGGATCC (SEQ ID NO 105) and 5' ATCATTCTGCAGGAATTTGGAT GTTAGTTCGGCAC (SEQ ID NO 106) were used to amplify a cDNA fragment which was cloned into the BamHI/PstI sites of the plasmid from step one above, to complete the L protein ORF. Four cDNA clones for each of the three ORFs were sequenced and the ORF with the highest level of homology to the Jeryl Lynn consensus nucleotide/amino acid sequence was chosen in each case for use in rescue experiments.

1.C. Construction of a synthetic MUV minireplicon. Referring to FIG. 1, The T7 RNA polymerase promoter sequence was designed to start transcription with the exact MUV 5' terminal nucleotide, and a HDV ribozyme sequence (Been et al.) was positioned to generate the precise MUV 3' terminal nucleotide in minireplicon RNA transcripts. Duplicate T7 RNA polymerase termination signals were included after the HDV ribozyme sequence. The bacterial chloramphenicol acetyl transferase (CAT) ORF replaces all of the coding and intercistronic sequence of the MUV genome; the remaining essential MUV specific sequence comprises the 3' MUV Leader (55 nt) with adjacent 90 nt NP gene untranslated region (UTR), and the 5' MUV Trailer (24 nt) adjacent to the 137 nt L gene UTR.

The synthetic MUV minireplicon (MUVCAT) was assembled from cDNA representing a modified MUV genome, where all the coding and intercistronic regions were replaced by the CAT ORF. The cDNA for the MUV 3' and 5' ends was amplified by RT/PCR from total infected-cell (CEF) RNA, using primer pairs 5' ACCAAGGGGAGAATGAATATGGG (SEQ ID NO 107)/5'ATCATTCGTCTCTTTTCCAGGTAGTGTCAAAATGCC (SEQ ID NO 108), and 5'ACCAAGGGGAGAA AGTAAAATC (SEQ ID NO 109)/5' ATCATTCGTCTCTATCGAATAAAGACTCTTCTGGC (SEQ ID NO 110) respectively. In a second round of PCR amplification nested primers were used for addition of the T7 RNA polymerase promoter and the 5' to NarI portion of the hepatitis delta virus (HDV) ribozyme sequence to the MUV 5' and 3' ends respectively; these primer pairs were: 5'AAGCTCGGCGGCCGCTTGTAA TACGACTCACTATAACCAAGGGGAGAAAGTAAAATC (SEQ ID NO 111)/5' ATCATT CGTCTCTATCGAATAAAGACTCTTCTGGC (SEQ ID NO 112); for addition of the T7 RNA polymerase promoter, and 5' ATCATTGGCGCCAGCGAGGAGGCTGGGACCATGCCGGCCACCAAGG GGAGAATGAATATGGG (SEQ ID NO 113)/5' ATCATTCGTCTCTTTTCCAGGTAGTGTCAAAATGCC (SEQ ID NO 114) for addition of the ribozyme component. The CAT ORF cDNA was amplified using primers 5' TCATTCGTCTCGGAAAATGGAGAAAAAAAT CACTGGATATACC (SEQ ID NO 115) and 5'ATCATTCGTCTCTCGATTTA CGCCCCGCCCTGCCACTC (SEQ ID NO 116). All three components were gel purified, trimmed with BsmBI, joined together in a four-way ligation and cloned into the NotI/NarI sites of modified pBSK S (+)(Sidhu et al., 1995) to produce the complete minireplicon plasmid, pMUVCAT.

Figure 2:
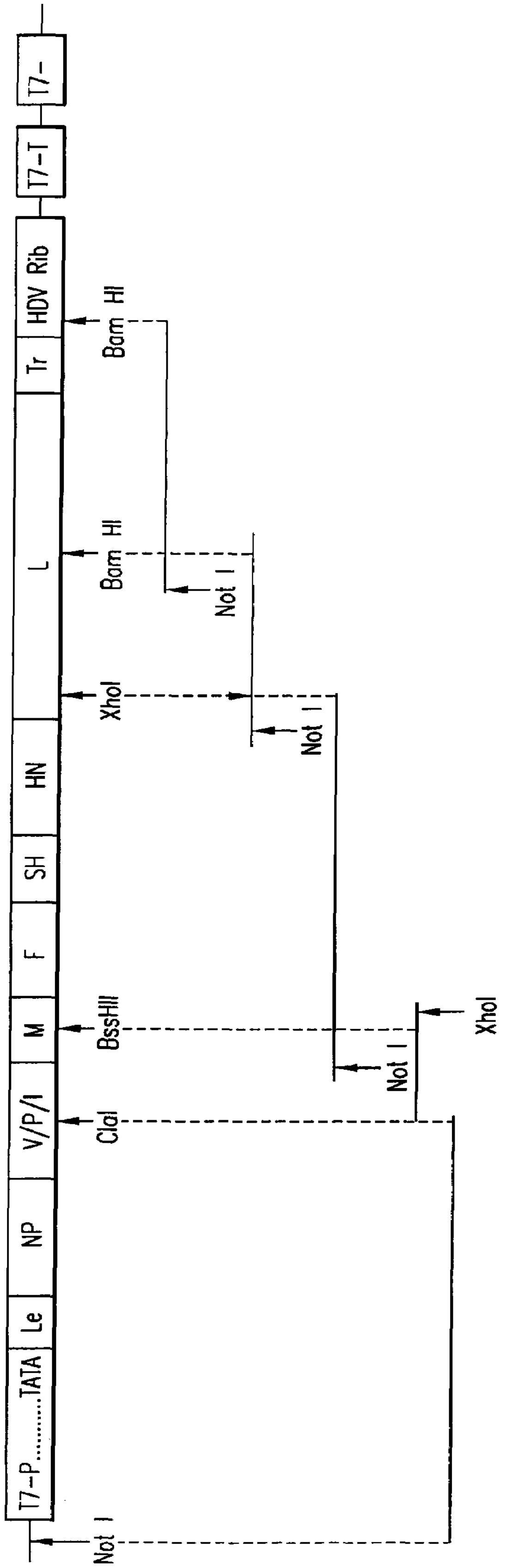
FIG. 2 is a schematic representation of the MUV full-length genome cDNA construct, including the sub-genomic fragments and restriction endonuclease sites used in the assembly process. The T7 RNA polymerase promoter and the HDV ribozyme sequence were positioned to initiate transcription with the exact 5' terminal nucleotide and generate the precise 3' terminal nucleotide of the MUV antisense genome, respectively. Tandem T7 RNA polymerase termination sequences were placed adjacent to the HDV ribozyme to help improve the efficiency of RNA cleavage. Nucleotide substitutions utilized as identifying tags for rescued MUV are shown at Table 1 (See FIG. 8).

1.D Construction of a full length genome cDNA for MUV. The full length genome cDNA of MUV (pMUVFL) was assembled 5' end to 3' end by the successive cloning of contiguous cDNA fragments into the same plasmid backbone that was used for the construction of pMUVCAT (See FIG. 2). Each cDNA fragment was amplified from total infected-cell RNA by RT-PCR using primer pairs which contained suitably unique restriction sites; in each case the positive sense primer contained a 5' proximal NotI site in addition to the virus specific endonuclease site, to facilitate the step-wise cloning strategy. Prior to addition to the growing full length clone, the cDNA fragment spanning the virus 3' end to the BssHII site was assembled separately in pBluescript II SK(+) (Stratagene, La Jolla, Calif.). In the first step the BssHII/ClaI cDNA fragment was cloned into the ClaI/XhoI sites of pBluescript, using a 5' extended primer to generate an XhoI site adjacent to the virus specific BssHII site. In the second step the virus 3' end to ClaI cDNA fragment was cloned into the NotI/ClaI sites of plasmid from the first step to complete the virus 3' end to BssHII sequence. The T7 RNA polymerase promoter sequence was added to the virus 3' end by incorporation into the (+) sense RT/PCR primer used to generate the virus 3'end/ClaI terminal fragment. The 5' terminal fragment (BamHI/NarI) of the genome cDNA was separately modified in a second round of PCR amplification in order to add the 5'end to NarI portion of the HDV ribozyme sequence. A total of four cloning cycles was employed for assembly of pMUVFL; after each round, four clones were sequenced in the region of newly added cDNA and compared to MUV consensus sequence. The cDNA clone containing the least number of mutations was then selected for addition of the next cDNA fragment. The fully assembled cDNA clone was resequenced to verify stability during bacterial amplification. Electrocompetent SURE cells (Stratagene, La Jolla, Calif.) and DH5alpha cells (GibcoBRL, Grand Island, N.Y.) were used as bacterial hosts for cloning of MUV cDNA.

1.E Rescue of CAT activity from transfected cells. For rescue of CAT activity, cells were either infected with MUV and transfected with in vitro transcribed MUVCAT minireplicon RNA or infected with MVA-T7 and transfected with pMUVCAT along with pMUVNP, pMUVP and pMUVL expression plasmids. In vitro transcriptions were carried out with 4 μg of pMUVCAT as the template for T7 RNA polymerase in a 20 μl final volume according to the manufacturer's protocol (Promega, Madison, Wis.); template DNA was then digested with RQ-1 DNase. Overnight cultures of 293 cells grown to approximately 80% confluence in six-well dishes were infected with MUV at a moi of 1-2; at 1 hour post infection (hpi) a mixture containing 5-10 μl of in vitro transcription reaction (approximately 5-10 μg RNA) and 10-12 μl of LipofectACE (GibcoBRL) was added to each well, according to the manufactuer's protocol. At 48 hpi cells were scraped into suspension, collected by centrifugation, resuspended in 100 μl of 0.25M tris buffer pH 7.8, and subjected to three rounds of freeze-thaw. The clarified cell extracts were then assayed for CAT activity using either $^{14}C$ labelled chloramphenicol (Sidhu et al., 1995) or fluorescein labelled chloramphenicol as substrate (Molecular Probes. Eugene, Ore), followed by analysis of reaction products on a Thin Layer Chromatogram.

For rescue of CAT activity in the absence of MUV helper virus, 293, Hep2 and A549 cells were grown overnight in six-well dishes to approximately 80% confluence, infected with MVA-T7 at an moi of 10 and transfected 1 hpi with a mixture containing 200 ng pMUVCAT, 300 ng pMUVNP, 50 ng pMUVP, 200 ng pMUVL, and 10-12 μl of LipofectACE. At 24 hpi the transfection mixture was replaced with 2 ml of fresh growth medium and cells were incubated for a further 24 hr, followed by preparation of cell extracts and CAT assay as described above.

1.F Recovery of infectious full length MUV from transfected cells. For rescue of infectious MUV from cDNA, A549 cells grown overnight to approximately 90% confluence in six-well dishes were infected with MVA-T7 at an moi of 4; at 1 hpi cells were transfected with a mixture containing 3-7ug pMUVFL, 300 ng pMUVNP, 50 ng pMUVP, 200 ng pMUVL and 14 μl of Lipofectace. At 24 hpi the transfection mixture was replaced with growth medium (DMEM containing 10% fetal calf serum), and cells were incubated at 37° C. for a further 48 hr; either supernatants (P1) or total transfected cell monolayers scraped into suspension were then transferred directly onto confluent A549 cell monolayers, which were incubated at 37° C. for four days and then prepared for whole cell ELISA (see below) in order to detect MUV infectious foci. Supernatants (P2) from these A549 indicator cells were further passaged onto confluent Vero cell monolayers and incubated at 37° C. for 3-4 days to observe MUV induced syncytia.

1.G Identification and authentication of rescued MUV. Initial identification of rescued MUV (rMUV) was carried out using a whole cell ELISA; A549 cells infected with transfection supernatants (see above) were fixed with 10% formaldehyde in 1× phosphate buffered saline (PBS) for 30 mins at room temperature; cells were then rinsed once with PBS and once with blocking solution (5% (w/v) milk in x1 PBS), followed by incubation overnight at 4° C. in blocking solution. The overnight blocking solution was then removed and cells were incubated at room temperature for 2-3 hr with MUV polyclonal rabbit antiserum (Access Biomedical, San Diego) diluted 1/400 in fresh blocking solution. The polyclonal antiserum was then removed; cells were rinsed 5× with blocking solution and were then incubated at room temperature for 2-3 hr with horseradish peroxidase (HRP) conjugated goat anti-rabbit serum (DAKO Corporation, Carpinteria, Calif.), diluted 1/1000 in blocking solution. The goat serum was then removed; cells were washed 5× with blocking solution and 1× with PBS, followed by addition of enough AEC substrate (DAKO Corporation) to cover cell monolayers, which were then incubated at 37° C. for 15-20 mins to facilitate stain development.

Nucleotide tags present only in pMUVFL (not present in any laboratory grown Jeryl Lynn MUV) were verified in rMUV by sequence analysis of cDNA fragments amplified by RT/PCR from Vero cells infected with (P2) rMUV. RNA was prepared from infected cells in a six-well dish by extraction with Trizol (GibcoBRL) according to the manufacturer's protocol; one-fifth of the total RNA from each well was used as the template for RT/PCR amplification according to directions for the Titan Kit (Boehringer Mannheim, Indianapolis, Ind.), with primer pairs flanking each of three separate nucleotide tags. The resulting RT/PCR fragments were purified from a 1% agarose gel by electroelution, and sequenced using an Applied Biosystems (ABI) 377 sequencer (Applied Biosystems, Inc., Foster City, Calif.) according to the manufacturer's protocols.

Example 2

Rescue of reporter gene activity from transfected cells. In order to help define a system which would permit the rescue of infectious mumps virus from cDNA, a mumps virus minireplicon containing the CAT reporter gene was assembled. The construct was designed to allow synthesis of a RNA minigenome of negative polarity under control of the T7RNA polymerase promoter. The three terminal G residues of the T7 promoter were omitted during construction of the minireplicon in order to provide a transcriptional start site which began with the precise 5' nucleotide of the MUV genome. Inclusion of the HDV ribozyme in the minireplicon construct permitted cleavage of the T7RNA polymerase transcript to produce the authentic MUV specific 3' end. The total number of nucleotides (966) in the MUVCAT minireplicon RNA was divisible by six, in agreement with the Rule of Six (Calain and Roux, 1993), which states that unless the genome length is a multiple of six, efficient replication will not occur. Expression of the CAT gene was under control of a MUV specific promoter, and could occur only if minireplicon RNA became encapsidated with NP protein and then interacted with functional MUV specific RNA polymerase proteins.

Figure 3A:
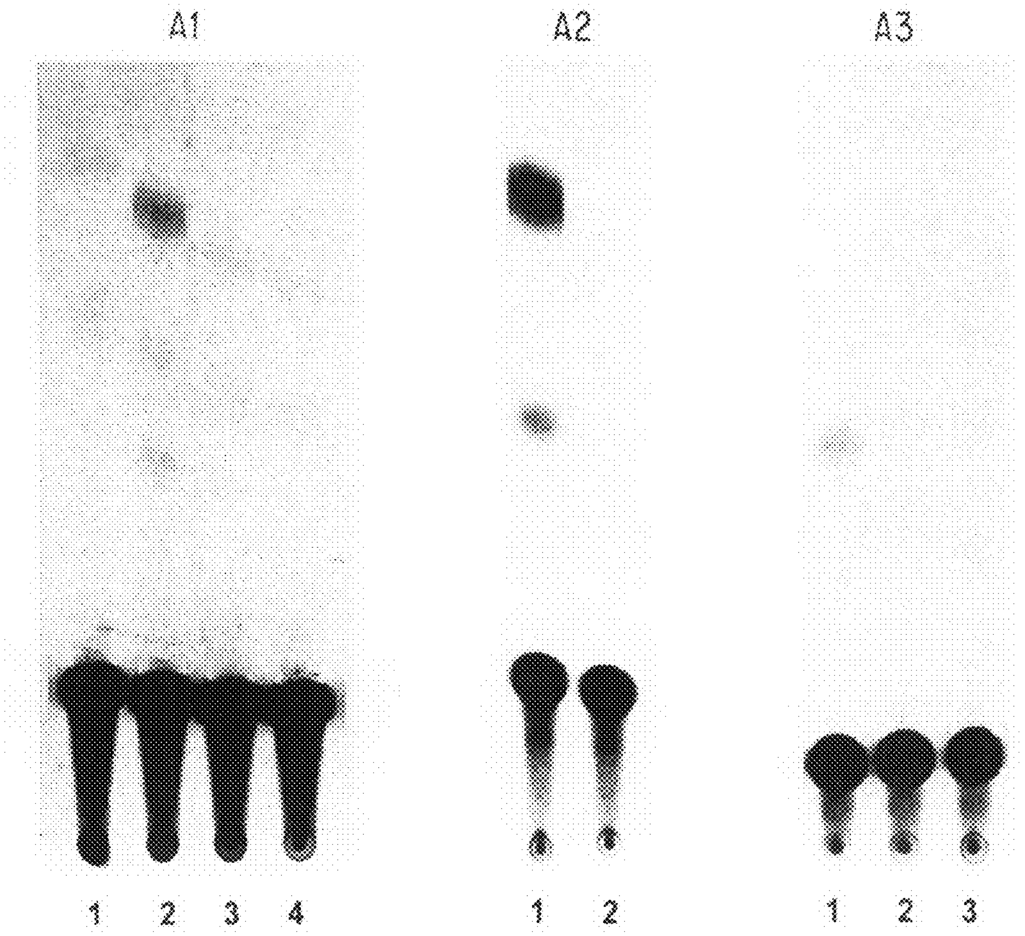
FIG. 3A depicts three thin layer chromatograms that show CAT activity present in 293 cells following infection with MUV and transfection with RNA transcribed in vitro from pMUVCAT as described in Example 2.

Recovery of CAT activity was observed here using two different rescue systems. In the first procedure in vitro transcribed MUVCAT RNA was transfected into 293 cells which had been previously infected with MUV. Under these conditions rescued CAT activity was usually relatively low, but was reproducible and always well above background levels (See FIG. 3A). Panels A1, A2 and A3 show the results from three separate rescue experiments; panel A1, lane 1 shows CAT activity in MUV-infected cells transfected without in vitro transcribed pMUVCAT RNA, lane 2 shows CAT activity in MUV-infected cells transfected with RNA transcribed in vitro from pMUVCAT; lane 3 shows CAT activity in MUV-infected cells transfected with RNA transcribed in vitro from pMUVCAT-GG; lane 4 shows CAT activity in uninfected cells transfected with RNA transcribed in vitro from pMUVCAT. Each CAT assay shown in panel A1 was carried out at 37° C. for 3-4 hrs with 20% of the extract from approximately $10^6$ transfected cells. Panel A2 lane 1 shows MUV-infected cells transfected with RNA transcribed in vitro from pMUVCAT; lane 2 shows uninfected cells transfected with RNA transcribed in vitro from pMUVCAT. Each CAT assay shown in panel A2 was carried out at 37° C. for 5 hrs using 50% of the extract from approximately $10^6$ transfected cells. Panel A3 lane 1 shows MUV infected cells transfected with RNA transcribed in vitro from pMUVCAT; lane 2 shows MUV-infected cells transfected without in vitro transcribed pMUVCAT RNA; lane 3 shows uninfected cells transfected with in vitro transcribed RNA from pMUVCAT. Each CAT assay shown in panel A3 was carried out at 37° C. for 4 hrs using 50% of the extract from approximately $10^6$ transfected cells.

Figure 3B:
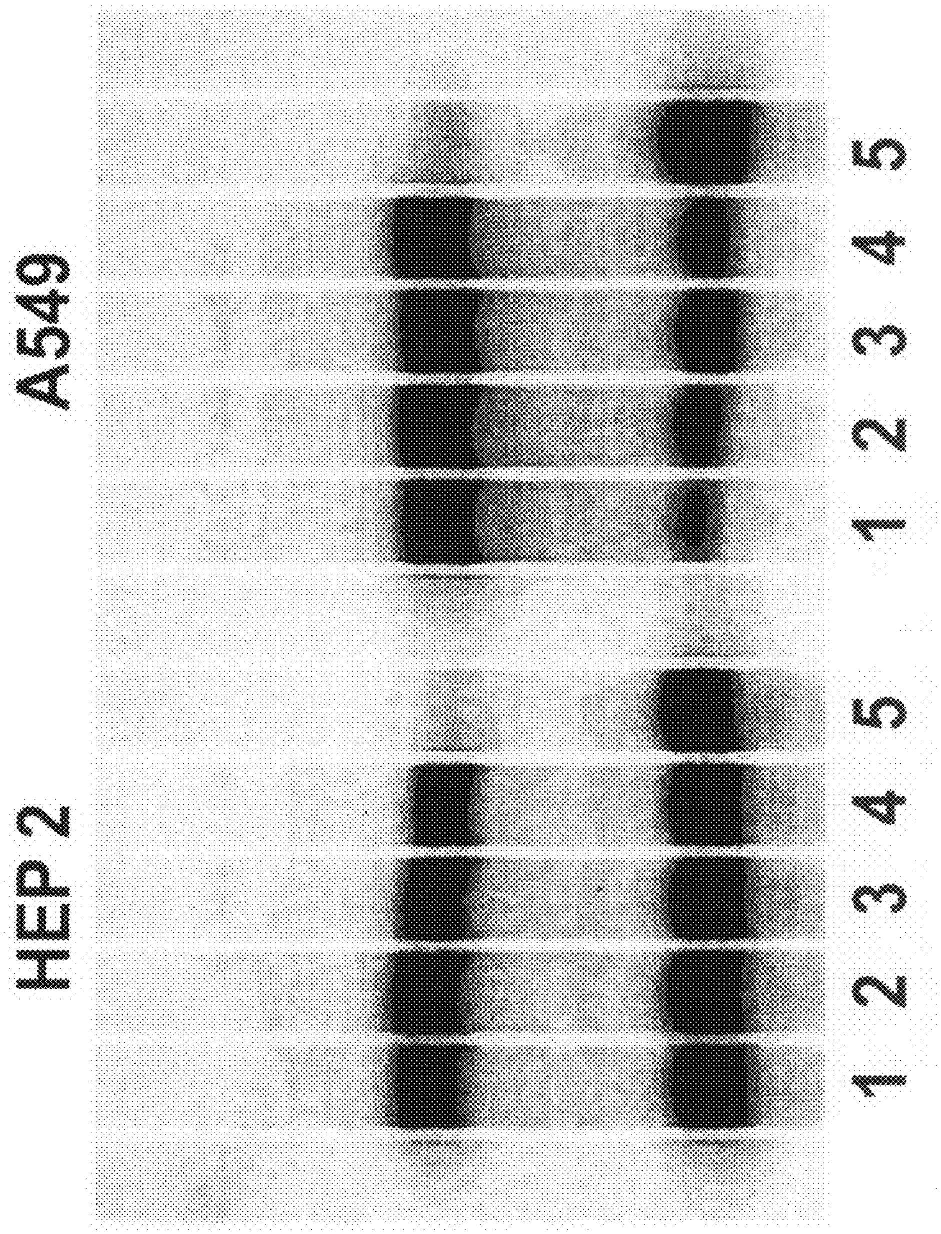
FIG. 3B depicts thin layer chromatograms showing CAT activity in MVA-T7 infected Hep2 and A549 cells following transfection with pMUVCAT and plasmids expressing MUV NP, P and L proteins. The level of pMUVNP expression plasmid was titrated in both cell lines; lanes 1-4 show CAT activity following transfection with mixtures containing 200 ng pMUVCAT, 50 ng pMUVP, 200 ng pMUVL each, and 300 ng, 450 ng, 600 ng, 750 ng pMUVNP respectively; lane 5 shows CAT activity produced when pMUVL was omitted from the transfection mixture.

CAT activity could not be rescued from a MUVCAT construct (pMUVCAT-GG) which contained 2 of the 3 additional G residues normally present in the T7RNA polymerase promoter. However, two mutations present in the MUV trailer region of the same MUVCAT construct prevented conclusive interpretation of this observation. Results from these experiments indicated that nt1-145 and nt15223-15384 of the MUV genome contained the necessary sequences for genome encapsidation, transcription and presumably replication. Having defined a minireplicon sequence which permitted rescue of CAT activity in the presence of MUV expressed helper proteins, a second system was designed to carry out rescue of CAT activity from transfected DNA, including pMUVCAT, pMUVNP, pMUVP and pMUVL. In this system MUV NP, P and L proteins and MUVCAT minireplicon RNA transcripts were co-expressed inside 293, Hep2, and A549 cells, under control of MVA-T7 induced T7RNA polymerase. Initial experiments carried out in 293 cells indicated that CAT rescue was efficient and reproducible. Increased efficiency of CAT rescue was seen in Hep2 cells relative to 293 cells, and a series of plasmid titrations was performed to optimize the relative amounts of each plasmid in the transfection mixture. Further increase in rescue efficiency was observed in A549 cells relative to Hep2 cells, with almost 100% conversion of substrate in a 3 hr CAT assay, using 20% of A549 cell lysate from one well of a six well dish. (FIG. 3B). These results demonstrated that the MUV helper proteins expressed from pMUVNP, pMUVP and pMUVL were sufficient to promote encapsidation, replication and transcription of MUVCAT antisense RNA minigenomes. Furthermore, the optimal conditions observed for CAT rescue provided a starting point for the rescue of infectious MUV entirely from cDNA.

Example 3

Recovery of full length mumps virus from transfected cells. The full length MUV cDNA was assembled in such a way as to permit the synthesis of a precise 15,384 nt positive sense RNA copy of the virus genome under control of the T7 RNA polymerase promoter. As with the MUVCAT minireplicon, the T7 RNA polymerase promoter sequence was modified to omit the three terminal G residues, providing a transcriptional start site beginning at the exact MUV terminal nucleotide. The HDV ribozyme was employed to generate the exact MUV 3' terminal nucleotide of the positive sense genome transcripts.

Figure 4A:
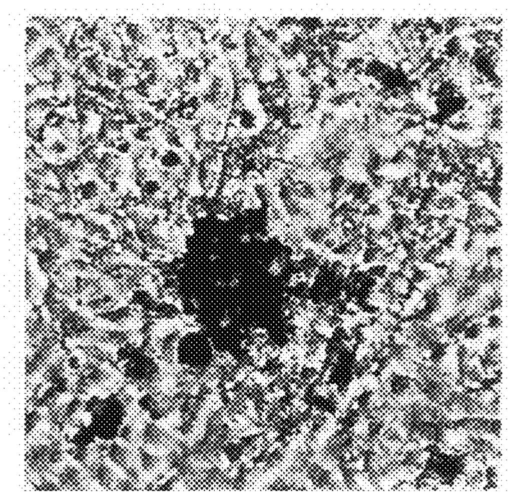
FIG. 4 depicts the Passage (P1) of transfected cell supernatants on A549 cells, as described in Example 3. Views A, B and C correspond to rescued mumps virus, no mumps virus (control) and Jeryl Lynn strain of mumps. The views show similar infectious foci for A and C.
Figure 4B:
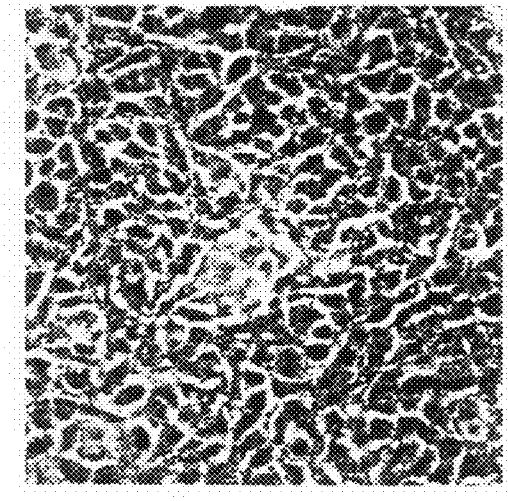
Figure 4C:
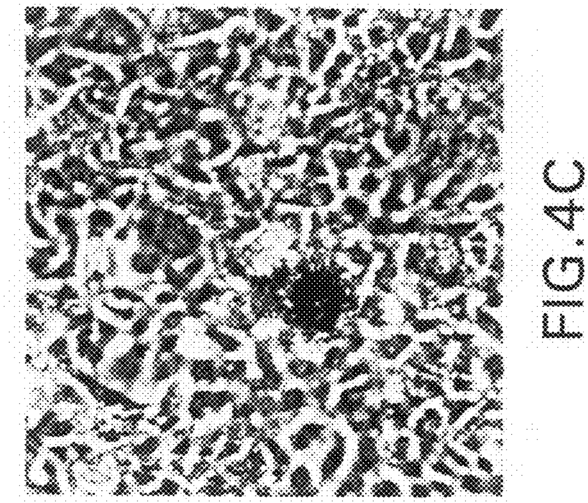
Figure 5C:
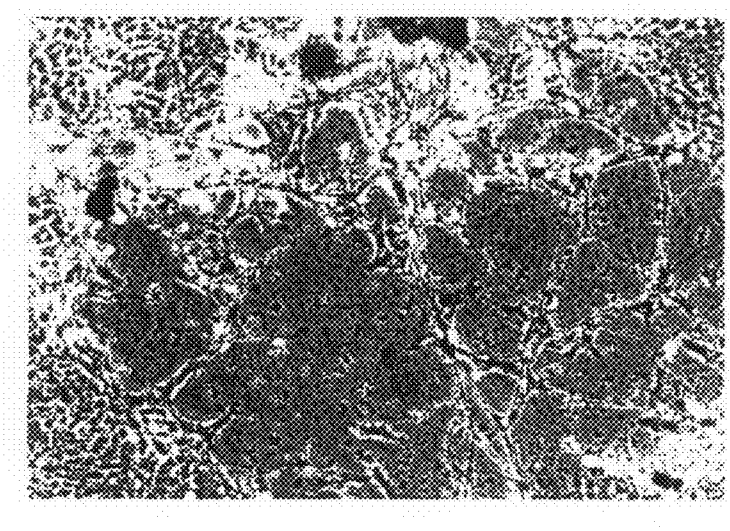
FIG. 5 depicts a whole cell ELISA of rescued mumps virus on a Vero cell monolayer, as described in Example 3.
Figure 5B:
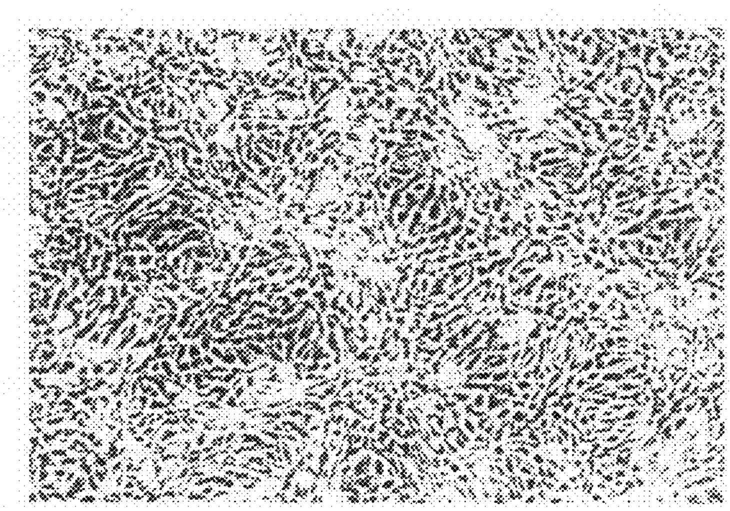
Figure 5A:
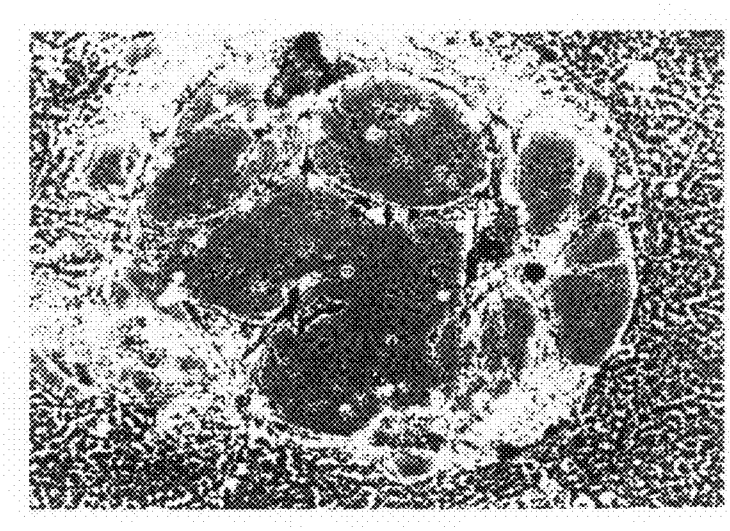

To recover MUV from cDNA, A549 cells were infected with MVA-T7 which expresses T7 RNA polymerase, and then transfected with pMUVFL, and plasmids expressing the MUV NP, P and L proteins. Results for rescue of reporter gene activity from the MUVCAT minireplicon along with results from similar work on the related rubulavirus SV5 (He et al, 1997; Murphy and Parks, 1997) indicated that the MUV NP, P and L proteins would be sufficient to encapsidate, replicate and then transcribe the T7 RNA polymerase generated positive sense genome RNA transcripts, provided all the interacting components were present at operable levels and ratios. A549 cells were chosen for MUV rescue experiments because they supported MUV replication and more efficient CAT rescue activity than other cell lines tested (potentially through more efficient transfection), and they were also more resistant to MVA-T7 induced cytopathology. In the first successful rescue experiment, supernatant medium (without clarification) from transfected cells was transferred to fresh A549 indicator cells. Three infectious foci were observed by whole cell ELISA in one out of five wells of indicator cells (FIG. 4). Following passage of supernatant from these cells onto a fresh Vero cell monolayer three syncytia were observed under the microscope. One of these syncytia was aspirated into medium as a liquid plaque pick, and used to infect fresh Vero cells; numerous syncytia were then observed on this cell monolayer (FIG. 5), and total infected-cell RNA was extracted for identification of rescued virus. In a second rescue experiment at least 10-20 infectious foci were obtained from each well of transfected cells as seen on indicator cells stained by whole cell ELISA (FIG. 5). In this experiment all wells, except where pMUVL was omitted from the transfection mixture, contained rescued virus, indicating that the rescue process was very reproducible. The optimal level of each plasmid so far determined for the rescue of MUV from cDNA is 300 ng pMUVNP, 50 ng pMUVP, 200 ng pMUVL and 3-7 μg of pMUVFL.

Example 4

Figure 6:
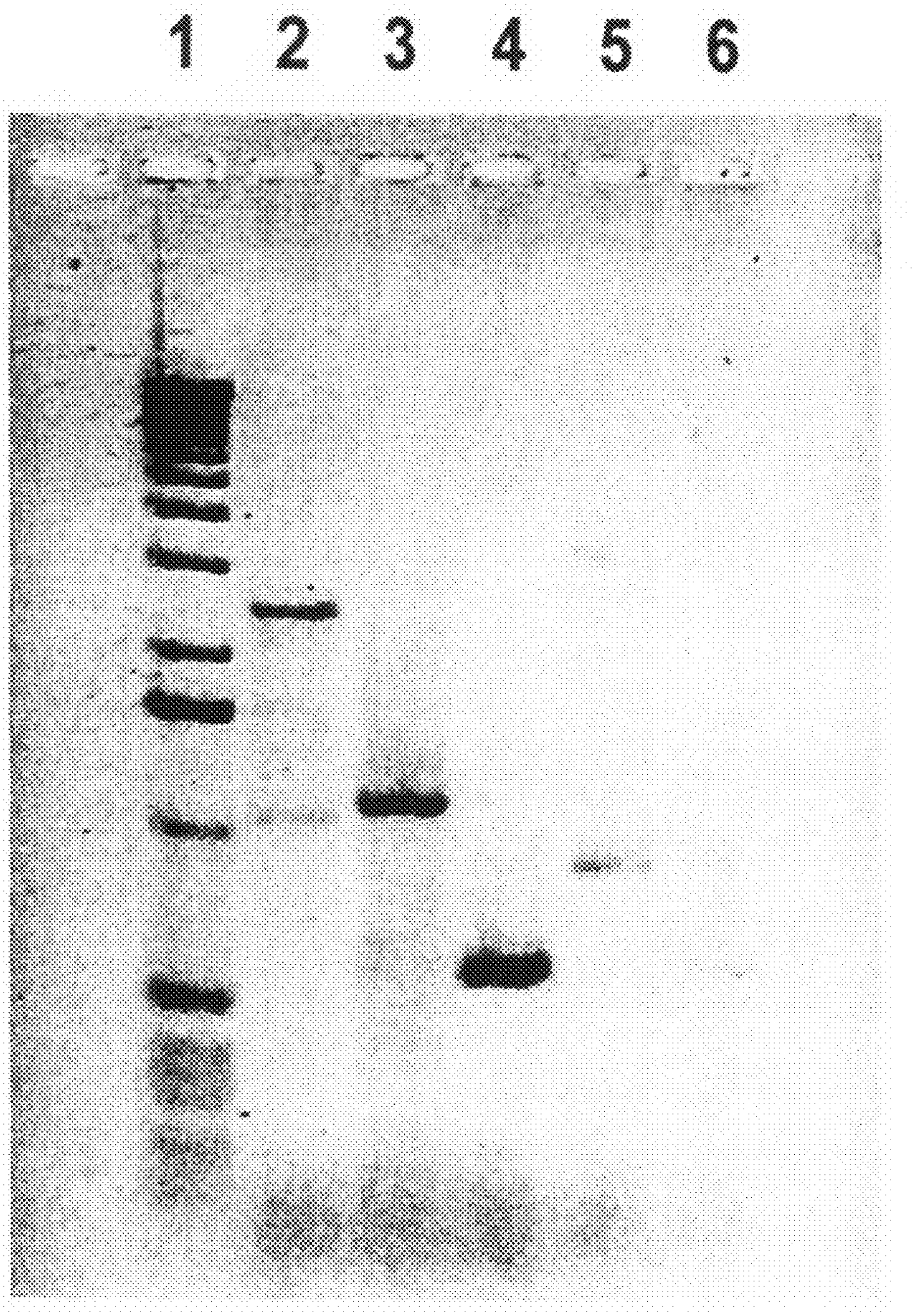
FIG. 6 shows the gel analysis of RT/PCR products used to identify rMUV (as described in Example 4). Total RNA was prepared from Vero cell monolayers infected with passage 2 of rMUV virus from transfected cells. RT/PCR reactions were set up to generate cDNA products spanning the 3 separate nucleotide tag sites present only in pMUVFL and rMUV. Lane 1 shows marker 1 kb ladder (Gibco/BRL); lanes 2, 3 and 4 show RT/PCR products spanning nucleotide tag positions 6081, 8502 and 11731, respectively. To demonstrate that these RT/PCR products were not derived from contaminating plasmid DNAs, an identical reaction to that used for the generation of the cDNA shown in lane 4 was performed without RT; the product(s) of this reaction are shown in lane 5. To demonstrate that no rMUV could be recovered when pMUVL was omitted from transfection mixtures, a RT/PCR reaction identical to that used to generate the cDNA products shown in lane 4 was set up using Vero cell RNA derived from transfections carried out without pMUVL; products from this reaction are shown in lane 6.

Identification of rescued MUV. It was important to demonstrate that rMUV was derived from pMUVFL. This was made possible by the presence of three nucleotide tags in pMUVFL, introduced by RT/PCR mis-incorporation during assembly of the full length genome cDNA. These tags differentiated pMUVFL from both the consensus sequences of the Jeryl Lynn vaccine virus, and a passaged plaque isolate of the Jeryl Lynn vaccine preparation from which pMUVFL was derived. Two of the tags represented silent changes at nucleotides 6081 and 11731 in the F and L genes respectively; a third tag resulted in a Lys to Arg substitution at amino acid 22 of the L protein (corresponding to nucleotide position 8502) of pMUVFL. To show that rMUV was generated from pMUVFL and not from either of the other two MUV populations grown in the laboratory, RT/PCR products, prepared from rMUV infected-cell RNA, spanning each of the three nucleotide tags were sequenced at the relevant position(s). To demonstrate that these RT/PCR products were derived solely from infected cell RNA, and not from carry-over of trace quantities of transfecting plasmid DNA, one reaction was carried out with rMUV infected cell RNA as the template for PCR amplification without prior reverse transcription. Results from the RT/PCR amplifications, and subsequent sequencing analysis of RT/PCR products are shown in FIG. 6. Total RNA was prepared from Vero cell monolayers infected with P2 rMUV virus from transfected cells. RT/PCR reactions were set up to generate cDNA products spanning the 3 separate nucleotide tag sites present only in pMUVFL and rMUV. Lane 1 shows marker 1 kb ladder (Gibco/BRL); lanes 2,3 and 4 show RT/PCR products spanning nucleotide tag positions 6081, 8502 and 11731 respectively. To demonstrate these RT/PCR products were not derived from contaminating plasmid DNAs, an identical reaction to that used for the generation of the cDNA shown in lane 4 was performed without RT; the product(s) of this reaction are shown in lane 5. To demonstrate that no rMUV could be recovered when pMUVL was omitted from transfection mixtures, a RT/PCR reaction identical to that used to generate the cDNA products shown in lane 4 was set up using Vero cell RNA derived from transfections carried out without pMUVL; products from this reaction are shown in lane 6.

Figure 7:
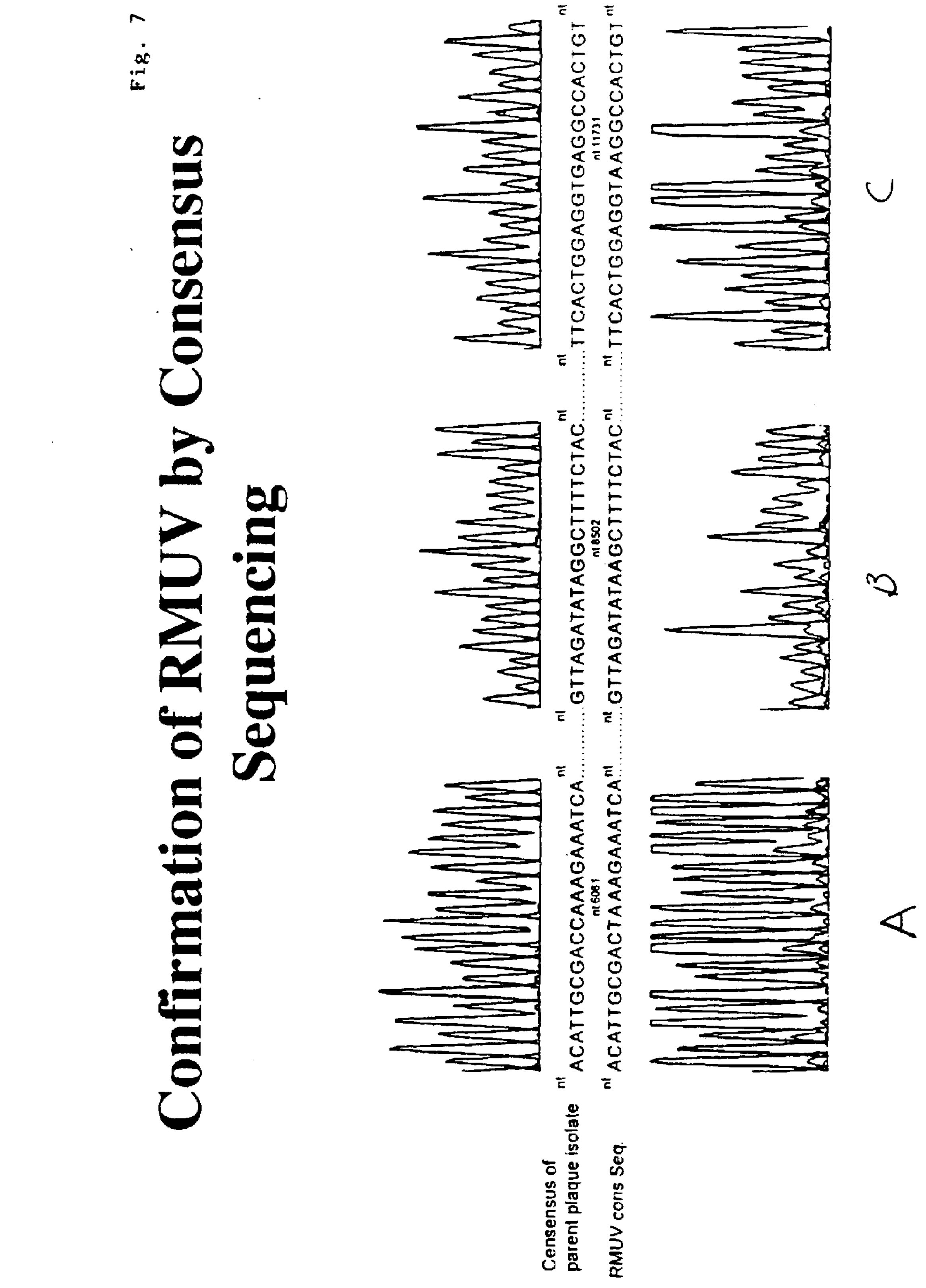
FIG. 7 depicts three electropherograms (A, B, and C) showing nucleotide sequence across identifying tag sites in rMUV. RT/PCR products (FIG. 6), which were sequenced across each of the three tag sites. The nucleotide sequence at each tag site obtained for rMUV cDNA is compared with consensus sequence for the plaque isolate of MUV (plaque isolate 4, PI 4) used to derive pMUVFL.

The consensus sequence data generated from the RT/PCR products shown in FIG. 6 clearly demonstrate that the rescued MUV contained the same nucleotide tags present only in the full length genome cDNA of MUV (FIG. 7). See Table 1 of FIG. 8 for a listing of the nucleotide and amino acid differences between the full length cDNA clone and the plaque isolate 4 (PI 4) and the consensus sequence for Jeryl Lynn strain (SEQ ID NO 1).

In view of the above examples, it is concluded that infectious mumps virus has been produced from a DNA copy of the virus genome. This procedure required the co-transfection of MVA-T7-infected A549 cells with plasmids encoding MUV NP, P and L proteins, along with a plasmid containing the complete genome cDNA of mumps virus. The success of this process was contingent upon the development of a consensus sequence for the entire mumps virus genome (Jeryl Lynn strain) and the novel development of a mumps virus minireplicon rescue system.

Note: A Lys to Arg substitution at amino acid 22 of the L protein in the full length construct did not disrupt obtaining the rescued mumps virus.

Example 5

Mumps Virus as an Expression Vector for One or More Heterologous Genes

The following experiments establish mumps virus as an expression vector. This embodiment is demonstrated by the recovery of infectious recombinant mumps virus expressing one or more reporter genes.

Figure 11:
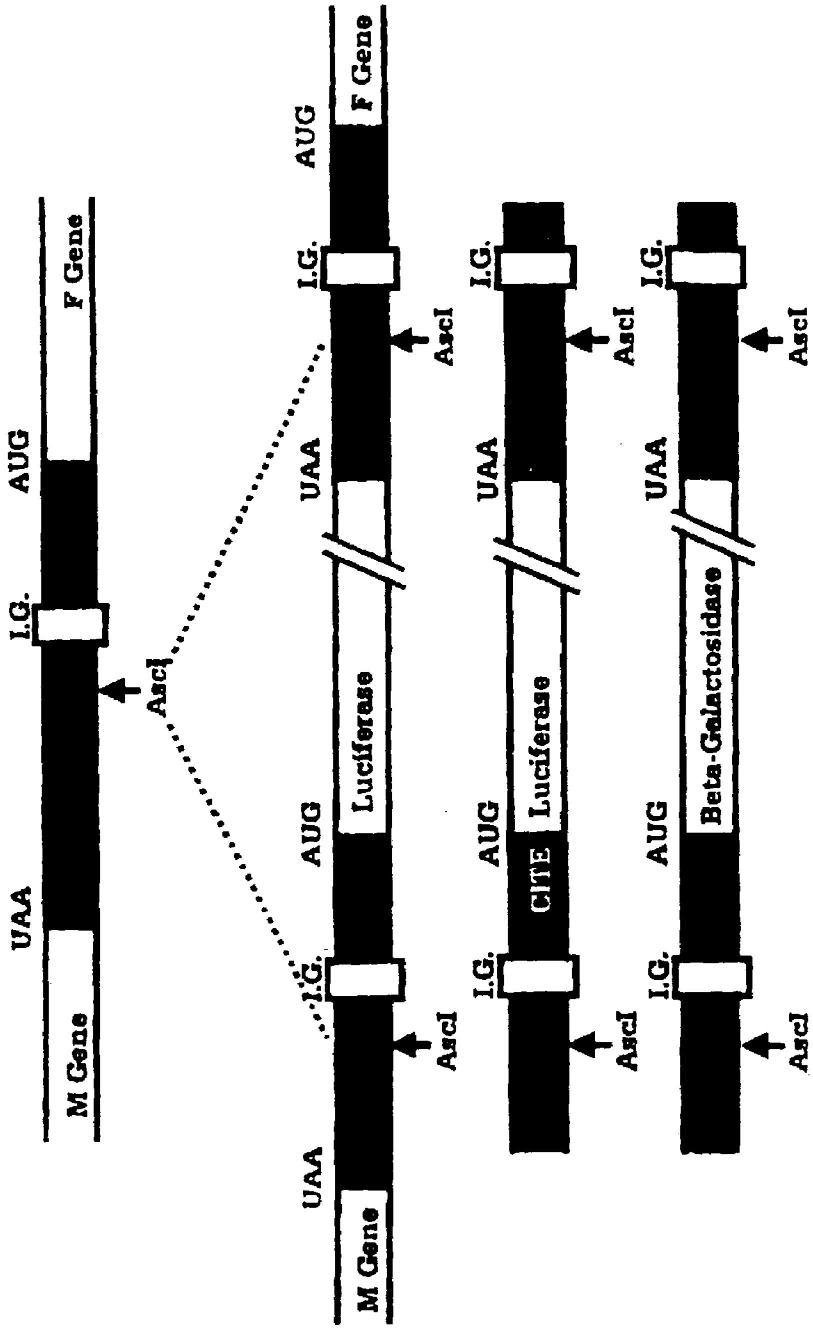
FIG. 11 is a diagram showing the insertion of the luciferase and beta-galactosidase gene(s) into the mumps virus genome between the M and the F genes. An AscI site was generated by site directed mutagenesis in the 5' non-coding region of the M gene. Nested PCR was used to generate mumps virus specific M-F intergenic sequence(s) and terminal AscI sites flanking each reporter gene. The resulting PCR product(s) were digested with AscI and imported into the genome AscI site.

Construction of recombinant mumps virus that contain either the Beta-Galactosidase gene, the Firefly Luciferase gene, or the Firefly Luciferase gene and the CAT gene. In order to permit insertion of heterologous genes or foreign genetic information into the mumps virus genome, a unique AscI restriction endonuclease site was generated in the full length genome cDNA, using site directed mutagenesis. The AscI site was positioned in the 5' non-coding region of the M gene (genome nucleotides 4451-4458), such that additional heterologous genes containing the appropriate flanking regulatory sequences of mumps virus and terminal AscI sites, could be integrated into the mumps genome between the virus M and F genes, to produce novel infectious mumps virus recombinant(s) capable of expressing the foreign gene(s). Mumps virus recombinants containing either the beta-galactosidase gene or the firefly luciferase gene have been constructed (see FIG. 11). Another recombinant mumps virus containing the EMC virus CITE adjacent to the luciferase translation initiation codon was also constructed for comparison with protein (luciferase) levels produced by the luciferase-containing recombinant which utilized the normal mumps virus cis-acting regulatory elements for initiation of translation.

The firefly luciferase gene was prepared for insertion into the mumps virus genome by two rounds of nested PCR, using primers which incorporated mumps virus specific sequences (genome nucleotides 4459-4538 and 4392-4449 respectively) adjacent to the ATG and UAA of the luciferase gene. In this process genome nucleotide 4450 was deleted from the PCR-generated DNA fragment to maintain the "rule-of-six" in the final luciferase-containing recombinant genome; also, in the same DNA fragment, genome nucleotides 4539-4545 were replaced by the seven nucleotides normally found upstream of the luciferase ATG. Terminal AscI sites present in the final PCR product facilitated addition of the luciferase gene and flanking mumps virus specific sequence into the mumps virus genome. Similarly, a separate mumps virus recombinant containing the beta-galactosidase gene was constructed. The PCR-generated DNA fragment incorporating the beta-galactosidase gene and flanking mumps virus specific sequences contained the same deletion of genome nucleotide 4450, as in the luciferase-containing DNA fragment. However a second TAA trinucleotide was incorporated adjacent to the normal TAA translation termination codon of the Beta-galactosidase gene, in order to preserve the "rule-of-six" in the final recombinant mumps virus genome. Also, unlike the luciferase-containing construct the seven upstream nucleotides flanking the Beta-galactosidase ATG (genome nucleotides 4539-4545) were mumps virus specific. A third mumps virus recombinant containing the EMC virus CITE adjacent to the ATG of the luciferase gene, was also constructed. As for the recombinant containing only the luciferase gene, nested PCR reactions were used to separately add mumps virus specific sequence at the 5' end and 3' end of the CITE and luciferase gene, respectively. In a three way ligation, the 3' end of the CITE and the 5' end of the luciferase gene were joined at the NcoI restriction endonuclease site and added into the AscI site of the mumps virus genome. Genome nucleotide 4450 was deleted, and the trinucleotide ACT was added to the 5' end of the CITE during PCR in order to preserve the "rule-of-six" in the resulting recombinant mumps virus.

Figure 12:
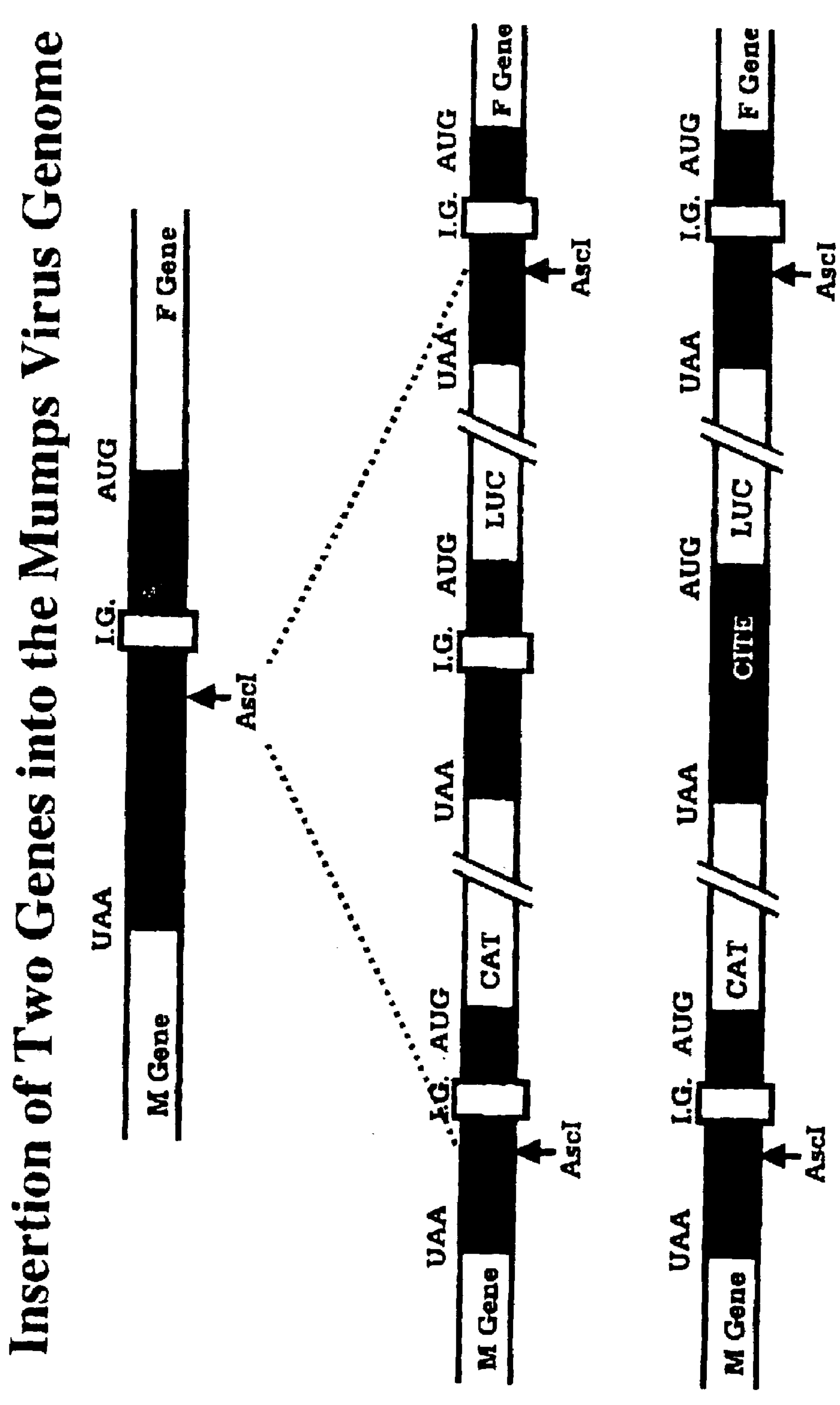
FIG. 12 is a diagram showing the insertion of two genes (luciferase and CAT) into the mumps virus genome. Two separate transcription units and a single transcription unit containing an internal ribosomal entry site for expression of the second gene of the polycistron, were separately inserted into the AscI site present in the M-F intergenic region. Nested PCR was used to generate the appropriate mumps virus M-F intergenic sequence flanking each gene and transcriptional unit.

Mumps virus recombinants were constructed that contained both the CAT gene and the luciferase gene, either as two separate transcriptional units, or as a single transcriptional unit containing the EMC CITE as an internal ribosomal entry site for translation of the second gene (luciferase) of the polycistron (see FIG. 12). Nested PCR was used to generate two DNA fragments, one containing the CAT gene and the other the luciferase gene, each flanked with the appropriate mumps virus specific intergenic cDNA sequence. Both of these fragments were joined and then ligated into the mumps virus genome cDNA via the AscI site previously used for the insertion of single reporter genes. Similarly, nested PCR was used to separately generate DNA fragments containing the CAT gene and the EMC CITE fused to the luciferase gene, each flanked with appropriate mumps virus specific intergenic cDNA sequence. Both DNA fragments were joined and ligated into the AscI site of the mumps virus genome cDNA. The order of reporter genes in both genome constructs was 5' CAT-LUC 3' and 5' CAT CITE LUC 3'

Rescue of mumps virus recombinants. Plasmids containing the recombinant mumps virus genomes, along with support plasmids expressing the mumps virus NP, P and L proteins were transfected into MVA-T7-infected A549 cells, as previously described above in Example 3. Total rescued virus from transfected cells was amplified first in fresh A549 cells (Passage1), and subsequently in Vero cells. At Passage 3, rescued virus was assayed for reporter gene activity.

Assay of reporter gene activity. Reporter gene activity was measured either in extracts of cells which had been infected with mumps virus recombinants or by cytological staining of infected cell monolayers. Extracts from cells infected with mumps virus recombinants containing either the luciferase gene, or the luciferase gene fused to the EMC virus CITE were assayed for luciferase activity in a luminomiter (Analytical Luminescence Laboratory, Monolight 2010). The preparation of cell extracts and luciferase assays were performed according to the manufacturer's protocol for the Enhanced Luciferase Assay Kit (Pharmingen, San Diego, Calif.). Extracts from cells infected with mumps virus recombinants containing the beta-galactosidase gene were assayed by cytological staining according to the protocol for the beta-gal staining kit (Promega, Madison, Wis.). Measurement of CAT activity was carried out on freeze-thaw lysates of infected cells, as previously described in the above Examples.

Figure 14:
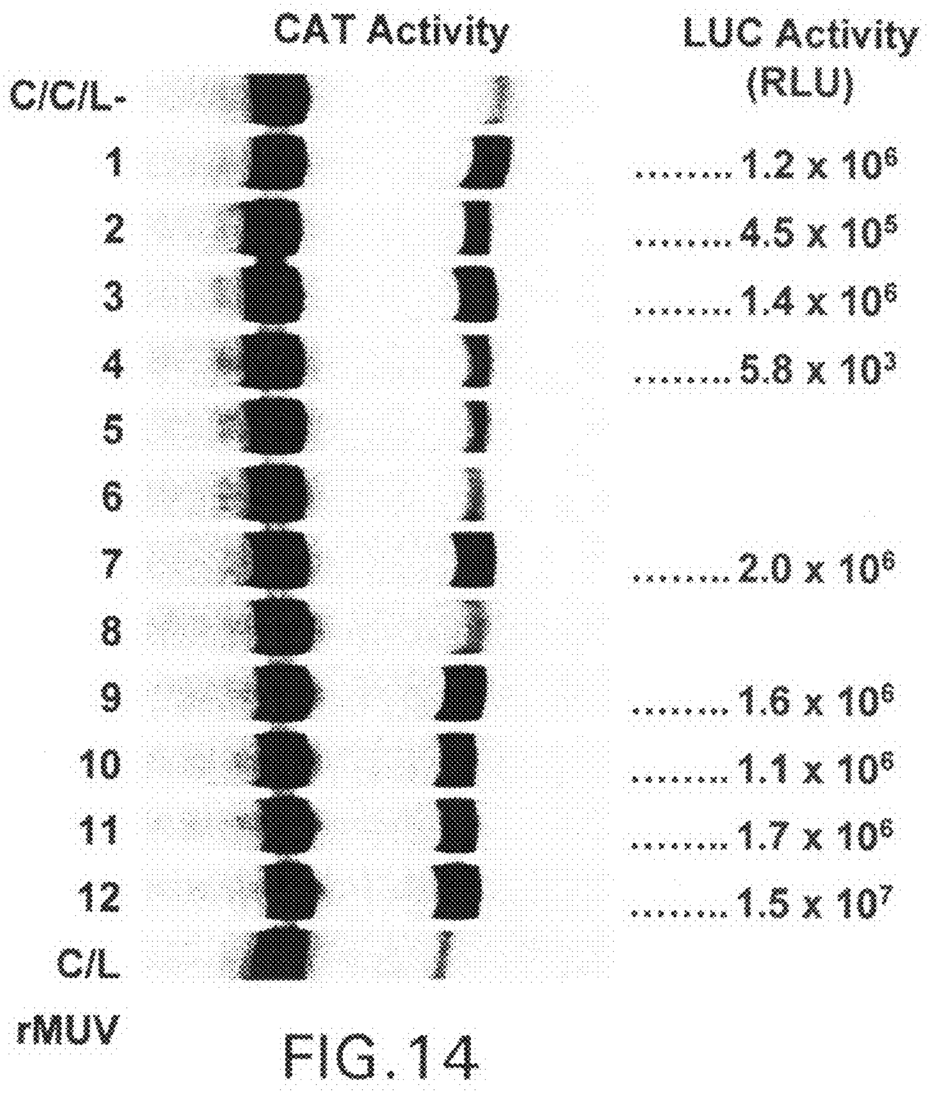
FIG. 14 depicts a thin layer chromatogram that shows CAT activity present in the extracts of Vero cells which were infected with rMUV containing both the CAT and luciferase genes, as described in Example 5.

Expression of Firefly luciferase by mumps virus. Robust luciferase activity was detected in the extracts of cells which had been infected with rescued virus. In each case, the rescued virus was derived from recombinant mumps virus genomic cDNAs which contained either the firefly luciferase gene alone or both the CAT gene and the luciferase gene in tandem. See FIG. 14, which is a thin layer chromatogram that shows CAT activity present in the extracts of Vero cells which were infected with rMUV containing both the CAT and luciferase genes. Recombinant virus containing the CAT and luciferase genes as one transcriptional unit (rMUVC/C/L) were plaque purified (1X) from total rescued virus prior to CAT assay. Rescued recombinant virus containing the CAT and luciferase genes as individual transcription units (rMUVC/L) was assayed as a total population without plaque purification. Where indicated in FIG. 14, luciferase activity in Vero cell extracts was also measured for both rMUVC/C/L and rMUVC/L virus recombinants.

In addition, Table 5 below shows the relative light units (RLU) readouts for clonal populations of mumps virus recombinants containing the luciferase gene (rMUV LUC and rMUV CITE-LUC), that were isolated from rescued virus populations by three successive rounds of plaque purification. The robust expression of luciferase activity by mumps virus recombinants, as shown in Table 5, clearly demonstrates the potential for mumps virus to express one or more heterologous genes from a recombinant genome(s).

TABLE 5

Quantitation of Luciferase produced by rMUVLUC and rMUVCITE-LUC

| Virus | RLU* | LUC (pg) | Total LUC (ng) | LUC/cell (fg) |
|---|---|---|---|---|
| rMUVLUC-2 | $2.9 \times 10^5$ | 8.7 pg | 300 ng | 150 fg |
| rMUVLUC-3 | $1.3 \times 10^5$ | 7.9 pg | 170 ng | 85 fg |
| rMUVLUC-4 | $2.0 \times 10^5$ | 8.3 pg | 400 ng | 200 fg |
| rMUVCITE-LUC-1 | $0.9 \times 10^5$ | 6.7 pg | 190 ng | 95 fg |
| rMUVCITE-LUC-2 | $0.2 \times 10^5$ | 3.2 pg | 180 ng | 90 fg |
| rMUVCITE-LUC-4 | $1.1 \times 10^5$ | 7.7 pg | 190 ng | 95 fg |
| RMUV | 0 | 0 | 0 | 0 |

*Average of two monolayer infections normalized to $10^4$ input pfu.

Figure 15A:
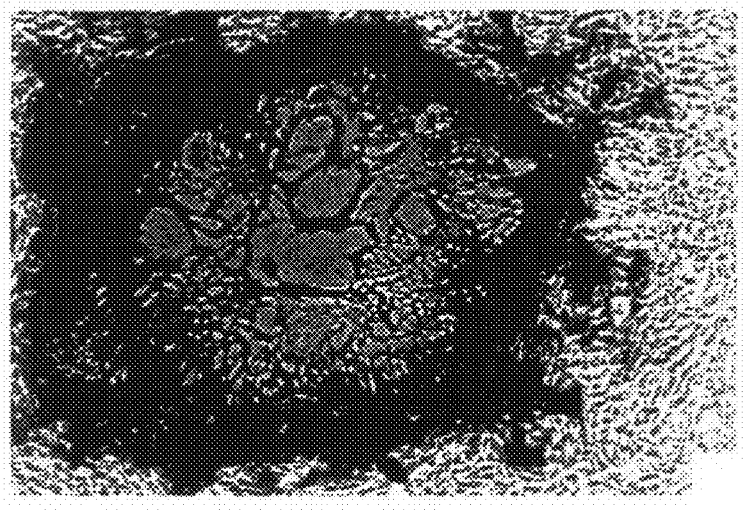
FIG. 15 is a photograph showing cytological staining of Vero cell monolayers which were infected with rMUV containing the beta-galactosidase gene, as described n Example 5. The presence of intense blue stain indicated beta-galactosidase expression and activity. Panel C also shows a "clear" plaque made by rMUV which did not contain any additional foreign genes.
Figure 15B:
Figure 15C:
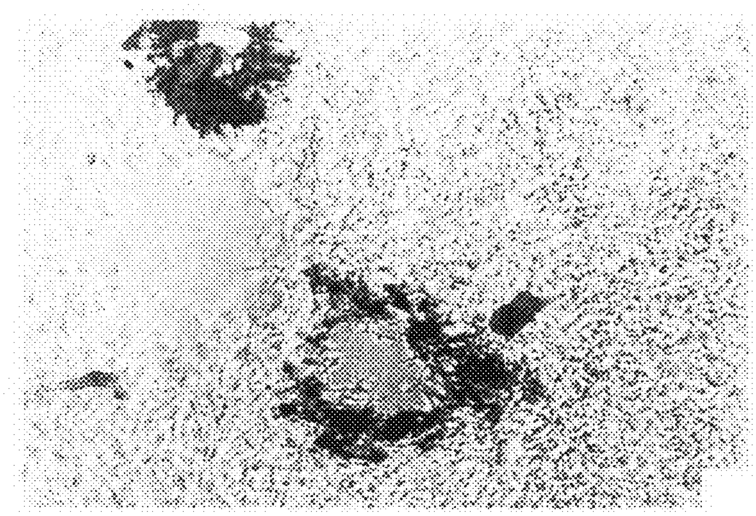

Expression of beta-galactosidase by mumps virus. Rescued mumps virus containing beta-galactosidase has been identified. Rescued virus was derived from recombinant mumps virus genomic cDNA containing the beta-galactosidase gene. Beta-galactosidase activity was evident in cells infected by recombinant mumps virus, following direct cytological staining. The intense blue stain of the beta-galactosidase activity was present only in cells infected by recombinant mumps virus which contained the beta-galactosidase gene. Rescued mumps virus which did not contain any additional heterologous genes produced clear plaques in the same staining assay (see FIG. 15). The expression of beta-galactosidase activity by recombinant mumps virus further demonstrates the ability of mumps virus to express relatively large heterologous genes under control of the mumps virus transcriptional promoter.

Example 6

Determination of the Consensus Sequence for JL5 and JL2

The Jeryl Lynn vaccine strain of mumps virus has been shown to consist of two individual variants, JL5 and JL2 (Afzal et al., 1993). The two variants, called JL5 and JL2, were shown to exist in a ratio of about 1 JL2 to 5 JL5 in the vaccine preparation. Since these variants possess sequence differences in the genome near the SH and HN genes, this difference was used to distinguish the variants on the genetic level by isolating pure populations of each and sequencing their entire genomes.

Isolation of JL5 and JL2 Variants from Mumps Virus Jeryl Lynn Strain.

Mumps virus Jeryl Lynn strain was cultured directly on chick embryo fibroblasts (CEFs) for one passage. This virus stock was then serially diluted in 10-fold increments and used to infect confluent CEFs on 6-well plates (Becton Dickinson, Franklin Lakes, N.J.). Cells were infected by rocking at room temperature for 1½ hours. The inoculum on each well was then replaced with an agarose overlay (containing 0.9% agarose [Seaplaque, FMC Bioproducts, Rockland, Me.], minimal essential media [MEM], 0.2 mM non-essential amino acids, 0.2 mg/ml penicillin/streptomycin, 2% FBS, and 0.3375% sodium bicarbonate). After the overlays solidified at room temperature, the infected cells were incubated at 37° C. for 6 to 8 days until plaques were visible by eye and light microscopy.

Individual plaques containing viruses were isolated using sterile Pasteur pipettes (VWR Scientific, New York, N.Y.) to remove an agarose plug over each plaque. The isolated plaques were placed in 1 ml of media (MEM supplemented with 2% FBS, 20 mM HEPES, and 0.1 mg/ml penicillin/streptomycin), vortexed, and used to infect for a second round of plaque purification. For subsequent steps, 10, 50, 75, 100, or 200 μl of each diluted plaque was used to infect fresh cells on 6-well plates. Infections, overlays, and plaque isolation were performed as described above. After isolating virus from the second round of plaquing, the process was repeated a third time.

Viruses isolated from third-round plaques were propagated on CEFs on 6-well plates for 4 to 6 days at 37° C. to prepare stocks. Viruses were then expanded by propagation on CEFs in T-25 flasks. After 5 to 7 days, when the infected cells showed the greatest cytopathology, viruses were harvested and stored frozen at −80° C.

RT-PCR and Sequencing of Isolated Variants.

RNA isolation and RT-PCR were performed as described in the "Isolation of viral RNA, amplification, and sequencing" section of example 1.A. The following gene-specific primers were used to amplify portions of the SH and HN genes: $_{6223}$TGAATCTCCTAGGGTCGTAACGTC$_{6246}$ (SEQ ID NO 27) and $_{8969}$ACCCACTCCACTCATTGTTGAACC$_{8946}$ (SEQ ID NO 69). Amplified products were gel-purified on 1% agarose and isolated from the gel slices using the Wizard PCR Purification Kit (Promega, Madison, Wis.). Amplified products were then sequenced in the SH gene region [using primers $_{6223}$TGAATCTCCTAGGGTCGTAACGTC$_{6246}$ (SEQ ID NO 27, $_{6783}$GGATGATCAATGATCAAGGC$_{6802}$ (SEQ ID NO 30), $_{7325}$CATCACTGAGATATTGGATC$_{7306}$ (SEQ ID NO 74), $_{6909}$GATACCGTTACTCCGTGAAT$_{6980}$ (SEQ ID NO 75)] to identify them as JL5 or JL2.

Preliminary sequence analysis in the SH gene region was performed to define which purified viruses were JL5 and which were JL2. Initially, all triple-plaque-purified viruses matched JL5. To obtain JL2 isolates, viruses that had been plaque-purified once and stored frozen were screened by RT-PCR and sequencing in the SH gene region to determine whether they were JL2 or JL5. Two isolates identified in this manner as JL2-containing plaques were subjected to two additional consecutive rounds of plaque purification. As above, these isolates were expanded twice in CEFs followed by RNA extraction, amplification, and sequencing.

After defining each plaque isolate as either JL5 or JL2, two separate isolates of each variant were chosen for sequencing the entire genome. RT-PCR was performed on isolated RNA using the following primer pairs to amplify fragments spanning the entire genome: $_{1}$ACCAAGGGGAGAATGAATATGGG$_{23}$ (SEQ ID NO 95) and $_{2507}$TGAGGCTCCATTCCCGTCTATG$_{2486}$ (SEQ ID NO 86), $_{2107}$CGTTGCACCAGTACTCATTG$_{2126}$ (SEQ ID NO 17) and $_{3875}$CTGAACTGCTCTTACTAATCTGGAC$_{3851}$ (SEQ ID NO 82), $_{3773}$CTGTGTTACATTCTTATCTGTGACAG$_{3798}$ (SEQ ID NO 21) and $_{6347}$CAGACATACAGGGTTATGATGAG$_{6325}$ (SEQ ID NO 76), $_{6223}$TGAATCTCCTAGGGTCGTAACGTC$_{6246}$ (SEQ ID NO 27) and $_{8969}$ACCCACTCCACTCATTGTTGAACC$_{8946}$ (SEQ ID NO 69), $_{7678}$AGAGTTAGATCAGCGTGCTTTGAG$_{7701}$ (SEQ ID NO 32) and $_{9753}$TCATGCCGCATCTCAATGAG$_{9734}$ (SEQ ID NO 67), $_{9583}$CCGAGAGTCCATGTGTGCTC$_{9602}$ (SEQ ID NO 37) and $_{11685}$CCTTGGATCT- $GTTTTCTTCTACCG_{11662}$ (SEQ ID NO 62), $_{11529}GTGTTAATCCCATGCTCCGTGGAG_{11552}$ (SEQ ID NO 42) and $_{13412}CATATTCGACAGTTTGGAGT_{13393}$ (SEQ ID NO 58), $_{13219}CGATTATGAGATAGTTGTTC_{13238}$ (SEQ ID NO 46) and $_{15384}ACCAAGGGGAGAAAG-TAAAATC_{15363}$ (SEQ ID NO 53). Amplified products were purified and sequenced as described in the "Isolation of viral RNA, amplification, and sequencing" section of example 1.A. To determine the sequences of the genomic termini of each virus isolate, the RNA termini were ligated, followed by RT-PCR across the junction, and sequencing (as described in Example 1.A).

Sequences were aligned using Sequencher software (Genecodes, Ann Arbor, Mich.). The JL5 and JL2 sequences represent the consensus determined by comparing both sequenced plaque isolates for each variant. Purified JL5 and JL2 viruses were sequenced with the same series of primers as listed in Table 4 of Example 1.A. For both variants, two separate plaque isolates were sequenced entirely (See SEQ ID NOS 11 and 12 for respective consensus sequences for JL5 and JL2, plaque 2 for each. As expected, a few sequence differences were observed between the two JL5 plaque isolates (See table 6) and the two JL2 plaque isolates (See Table 7). The consensus sequences of JL5 plaques 1 and 2 differed from Jeryl Lynn consensus sequence by 4 and 3 nucleotides, respectively (See Table 6).

The sequence of JL2 contains 413 differences from JL5, spread across the entire genome, as summarized in Table 8. Five of these differences are present in the viral 5' or 3' leader sequences. A total of 360 sequence differences lie within the coding regions of the viral genes; however, only 73 of these differences encode amino acid differences. The remaining 48 sequence differences lie within the noncoding regions of the viral genes. It is of interest to note that there are no sequence differences in the intergenic regions or within any of the internal cis-acting signals (i.e. gene start or gene end signals).

TABLE 6

Sequence differences between plaque isolates for JL5.

| Position | Jeryl Lynn Consensus | JL5 Plaque 1 | JL5 Plaque 2 | Amino acid | Gene/ AA position |
|---|---|---|---|---|---|
| 1405 | G | A | A | pro (silent) | N/420 |
| 1685 | T | C | C | tyr(T) or his(C) | N/514 |
| 1703 | T | A | T | ser(T) or thr(A) | N/520 |
| 9619 | T | C | C | phe (silent) | L/394 |

TABLE 7

Sequence differences between plaque isolates for JL2.

| Position | Jeryl Lynn Consensus | JL2 Plaque 1 | JL2 Plaque 2 | amino acid | gene/AA position |
|---|---|---|---|---|---|
| 4 | A | C | A | NA | leader |
| 3352 | A | C | A | gln(A) or his (C) | M/30 |
| 3508 | T | T | C | val(T) or ala(C) | M/82 |
| 3517 | T | T | C | val(T) or ala(C) | M/85 |
| 13467 | A | G | A | lys(A) or arg (G) | L/1677 |

TABLE 8

Summary of sequence differences between JL5 and JL2 variants.

| | Differences between JL5 and JL2 | | | |
|---|---|---|---|---|
| | noncoding region | | | |
| Gene | 3' end | 5' end | Coding | silent |
| Leader | 4 | — | Na | na |
| NP | 3 | 9 | 8 | 30 |
| P | 2 | 2 | 14 | 22 |
| M | 2 | 1 | 5 | 17 |
| F | 2 | 6 | 12 | 33 |
| SH | 1 | 6 | 5 | 5 |
| HN | 4 | 3 | 16 | 35 |
| L | 0 | 7 | 13 | 145 |
| Trailer | — | 1 | Na | na |
| TOTALS: | 18 | 35 | 73 | 287 |

na = not applicable.

Example 7

Determination of Relative Abundance of JL5 and JL2 in the Jeryl Lynn Vaccine.

In order to determine the relative ratios of JL5 to JL2 in a vaccine lot of Jeryl Lynn, an assay was developed that exploited sequence differences due to a restriction endonuclease polymorphism between the two variants. The assay is called mutational analysis by PCR and restriction endonuclease cleavage (MAPREC). At position 3828 (antigenomic sense), there is a BssH II restriction endonuclease recognition site in the JL5 genome. In JL2, a G to A nucleotide variation at this site results in a lack of BssH II recognition. RNA from a mixed population of JL5 and JL2 was isolated and amplified using primers surrounding this site, resulting in a 254 base pair product. The primers used were primers $_{3708}CAGGCCAGCGCCGATAAATATG_{3729}$ (SEQ ID NO 117) and $_{3962}AATGACACCCTTCTCCATCAGGG_{3941}$ (SEQ ID NO 118). The primers contained identical sequences to both JL5 and JL2; thus, the fragments from either variant were expected to amplify at equal probability. Furthermore, the first primer listed above contained fluorescein at its 5' end. The fluoresceinated fragment was cleaved with BssH II, and separated on an acrylamide gel. A FluorImager was used to scan the gel and to quantitate the relative abundance of cleaved and uncleaved products, which represent JL5 and JL2, respectively. Cleavage with BssH II left a 120-base pair fluorescent product for JL5 and a 254-base pair (i.e. uncleaved) fluorescent product for JL2.

RNA was isolated from ten vaccine vials of mumps virus Jeryl Lynn (Mumpsvax lot # 0656J, Merck and Co., Inc., West Point, Pa.). The RNA was amplified (by using the above primers) and the PCR products were digested with BssH II, separated on a gel, and scanned on the FluorImager. The enzyme digestion was performed by adding 5 units of BssH II (Roche Molecular Biology, Indianapolis, Ind.) to one-fifth of the PCR reaction mix and incubating at 50° C. for 2½ hours. The cleaved products were then separated on a 6% acrylamide gel that was then scanned using a FluorImager (Molecular Dynamics, Sunnyvale, Calif.).

Scanned images were quantitated using ImageQuant software (Molecular Dynamics, Sunnyvale, Calif.). A series of controls were used as standards; these samples consisted of pure JL5 and JL2 viruses mixed in the following ratios based on titers: 99% JL5/1% JL2, 95% JL5/5% JL2, 85% JL5/15%

Figure 13:
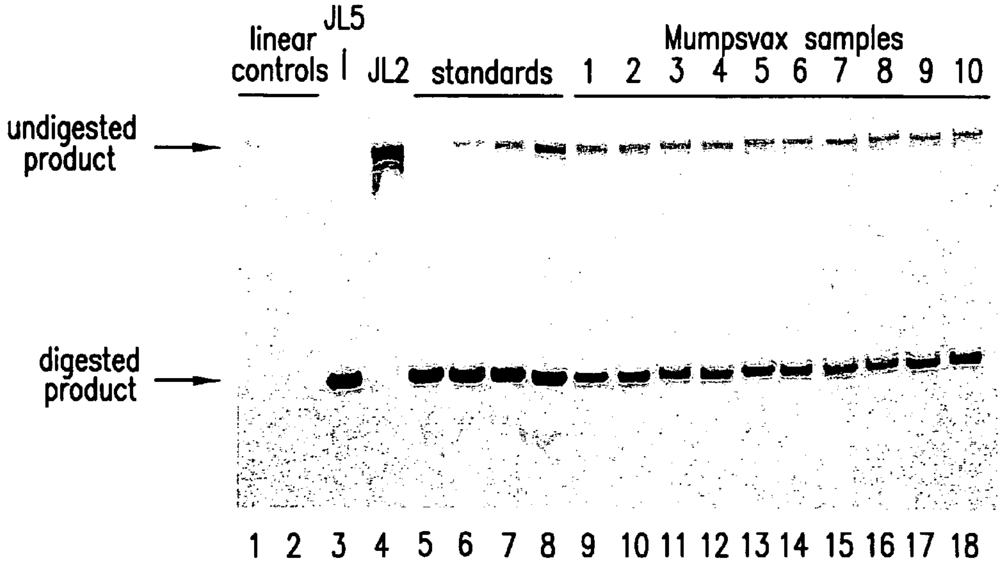
FIG. 13 depicts the results from the MAPREC analysis of ten Mumpsvax® vaccine samples for relative portions of JL5/JL2 as determined from RNA was isolated from ten vials of mumps Jeryl Lynn vaccine and amplified by RT-PCR, as described in Example 7. The tested samples in Lanes 1 and 2 are serial dilutions of undigested PCR product used to define the lower limits of linearity for the assay. In Lane 3 the PCR product is from a purified isolate of JL5. In Lane 4, the PCR product is from a purified isolate of JL2. In Lanes 5-8, the PCR products are from samples of JL5 and JL2 viruses mixed in the following ratios: 99 JL5/1 JL2, 95 JL5/5 JL2, 85 JL5/15 JL2, and 75 JL5/25 JL2, respectively. For Lanes 9-18, the PCR products are from Mumpsvax® samples 1-10.

JL2, and 75% JL5/25% JL2. RNA was isolated from the mixed viruses and used in the MAPREC procedure. Results from these controls were used to generate a standard curve for the assay, which was used to determine the relative percentages of JL5 and JL2 in the vaccine mixtures. In addition, a series of two-fold dilutions of undigested JL5 PCR product was used to determine the linear range of the results measured on the FluorImager. Furthermore, pure JL2 viral RNA was used as a negative control and pure JL5 viral RNA was used as a positive control. The pure JL5 sample also served as a control to determine the efficiency of the BssH II enzyme. The MAPREC assay and quantitation were repeated three times for reproducibility. The results were averaged over the three experiments. FIG. 13 shows a representative scanned gel image. The cleaved and uncleaved products are marked with arrows. The uncleaved product, which corresponds to JL2, is 254 base pairs long while the cleaved product, which corresponds to JL5, is 120 base pairs in length. To quantitate relative abundance for each scanned gel, values were first corrected for background fluorescence and for the amount of undigested DNA in a pure JL5 control sample. The % JL5 values were determined by dividing the amount of digested DNA by the total of digested and undigested DNA, and by multiplying that value by 100%. For each experiment, RNA from a set of mixed JL5 and JL2 viruses was used to generate a standard curve. The results of the described calculations for the vaccine samples were plotted on the standard curves to obtain the values shown in Table 9. In the final column, the averages for each vaccine sample are given for the three experiments. An overall average for the ten vaccine samples, which was generated by averaging the results in the last column, is shown at the bottom of the table.

Table 9 summarizes the results for the ten vaccine vials of Mumpsvax used in this assay. The relative abundance of the two variants within the vaccine for these samples was in the range of 73.1% JL5/26.9% JL2 to 76.1% JL5/23.9% JL2. The overall average for all ten vaccine samples for all three experiments was 73.9% JL5/26.1% JL2.

TABLE 9

Relative abundance of JL5 and JL2 in Mumpsvax samples.

| MumpsVax Sample | Expt 1 (% JL5/ % JL2) | Expt 2 (% JL5/ % JL2) | Expt 3 (% JL5/ % JL2) | Avg. (% JL5/ % JL2) |
|---|---|---|---|---|
| 1 | 73.7/26.3 | 72.5/27.5 | 74.5/25.5 | 73.6/26.4 |
| 2 | 74.1/25.9 | 72.0/28.0 | 73.3/26.7 | 73.1/26.9 |
| 3 | 73.0/27.0 | 76.8/23.2 | 73.3/26.7 | 74.4/25.6 |
| 4 | 73.9/26.1 | 75.1/24.9 | 71.2/28.8 | 73.4/26.6 |
| 5 | 74.6/25.4 | 73.9/26.1 | 70.9/29.1 | 73.1/26.9 |
| 6 | 76.0/24.0 | 76.3/23.7 | 69.8/30.3 | 74.0/26.0 |
| 7 | 77.2/22.8 | 75.9/24.1 | 70.4/29.6 | 74.5/25.5 |
| 8 | 76.2/23.8 | 74.8/25.2 | 68.7/31.3 | 73.2/26.8 |
| 9 | 79.1/20.9 | 72.1/27.9 | 77.0/23.0 | 76.1/23.9 |
| 10 | 78.8/21.2 | 73.0/27.0 | 69.7/30.3 | 73.8/26.2 |
| | | | Overall average: | 73.9/26.1 |

Provided below are a list of references which are incorporated herein.

REFERENCES

Afzal, M. A., Pickford, A. R., Forsey, T., Heath, A. B., and Minor P. D. (1993). The Jeryl Lynn vaccine strain of mumps virus is a mixture of two distinct isolates. J Gen Virol. 74; 917-920.

Baron, M. D., and Barrett, T. (1997). Rescue of rinderpest virus from cloned cDNA. J Virol, 71, 1265-1271.

Been, M. D., and G. S. Wickham. 1997. Self-cleaving ribozymes of hepatitis delta virus RNA. Eur. J. Biochem, 247:741-753.

Boyer, J. C. and Haenni, A. L. (1994). Infectious transcripts and cDNA clones of RNA viruses. Virology 198, 415-426.

Buchholz, U. J., Finke, S. and Conzelmann, K. K. (1999). Generation of bovine respiratory syncytial virus (BRSV) from cDNA: BRSV NS2 is not essential for virus replication in tissue culture, and the human RSV leader region acts as a functional BRSV genome promoter. J. Virol. 73: 251-259.

Calain, P. and Roux, L. (1993). The rule of six, a basic feature for efficient replication of Sendai virus defective interfering RNA. J. Virol. 67: 4822-4830.

Collins, P. L., Hill, M. G., Camargo, E., Grosfield, H., Chanock, R. M., and Murphy, B. R.(1995). Production of infectious human respiratory syncytial virus from cloned cDNA confirms an essential role for the transcription elongation factor from the 5" proximal open reading frame of the M2 mRNA in gene expression and provides a capability for vaccine development. Proc. Natl. Acad. Sci. USA 92; 11563-11567.

Durbin, A. P., Hall, S. L., Siew, J. W., Whitehead, S. S., Collins, P.

L. and Murphy, B. R. (1997). Recovery of infectious human parainfluenza virus type 3 from cDNA. Virology 235, 323-332.

Elango, N., Varsanyi, T., Kovamees, J., Norrby, E. Molecular cloning and characterization of six genes, determination of gene order and intergenic sequences and leader sequence of mumps virus. J. Gen. Virol. 1988; 69: 2893-2900.

Fuerst, T. R., Niles, E. G., Studier, F. W. and Moss, B. (1986). Eukaryotic transient expression system based on recombinant vaccinia virus that synthesizes bacteriophage T7 RNA polymerase. Proc. Natl. Acad. Sci. USA 83: 8122-8126.

Garcin, D., Pelet, T., Calain, P., Sakai, Y., Shioda, T., Roux, L., Curran, J., Kolakofsky, D. (1995). A highly recombinogenic system for the recovery of infectious Sendia paramyxovirus from cDNA: generation of a novel copy-back nondefective interfering virus. EMBO J. 14: 6087-6094.

He, B., Paterson, R. G., Ward, C. D. and Lamb, R. A. (1997). Recovery of infectious SV5 from cloned DNA and expression of a foreign gene. Virology, 237: 249-260.

Hoffman, M. A., and Banerjee, A. K. (1997). An infectious clone of human parainfluenza virus type 3. J. Virol. 71; 4272-4277.

Jin, H., D. Clarke, H. Z.-Y. Zhou, X. Cheng, K. Coelingh, M. Bryant, and S. Li. 1998. Recombinant human respiratory syncytial virus (RSV) from cDNA and construction of subgroup A and B chimeric RSV. Virology 251: 206-214.

Johnson, C. D. and Goodpasture, E. W. (1935). The etiology of mumps. Am. J. Hyg. 21: 46-57.

Kyte, J and Doolittle, R. F. (1992). J. Mol. Biol. 157: 105-137.

Lamb, R. A. and Kolakofsky, D. (1996) Paramyxoviridae. The viruses and their replication. In "Virology" (B N Fields, D M Knipe, and P M Howley, Eds.) 3rd edition, Vol1, pp 1177-1204. Raven Press, New York.

Lawson, N., Stillman, E., Whitt, M., and Rose, J. (1995). Recombinant vesicular stomatitis viruses from DNA. Proc. Natl. Acad. Sci. USA 92; 4471-4481.

Murphy, S. K. and Parks, G. D. (1997). Genome nucleotide lengths that are divisible by six are not essential but enhance replication of defective interfering RNAs of the paramyxovirus simian virus 5. Virology; 232, 145-157.

Moss, B., Elroy-Stein, O., Mizukami, T., Alexander, W. A., and Fuerst, T. R. 1990. New mammalian expression vectors. Nature 348:91-92.

Paterson, R. G. and Lamb, R. A. RNA editing by G-nucleotide insertion in mumps virus P-gene mRNA transcripts. J. Virol. 1990; 64: 4137-4145.

Peeters, B. P. H., deLeeuw, O. S., Koch, G., and Gielkens A. L. J. (1999) Rescue of Newcastle disease virus from cloned cDNA: evidence that cleavability of the fusion protein is a major determinant for virulence. J. Virol. 73: 5001-5009.

Perrotta, A. T., and Been, M. D. (1991) A pseudoknot-like structure required for efficient self-cleavage of hepatitis delta virus RNA. Nature, 350: 434-436.

Racaniello, V. R., and Baltimore, D. (1981). Cloned poliovirus complementary DNA is infectious in mammalian cells. Science 214: 916-918.

Radecke, F., Spielhofer, P., Schneider, H, Kaelin, K, Huber, M., Dotsch, C., Christiansen, G., and Billeter, M. A. (1995). Rescue of measles virus from cloned DNA. EMBO J; 14: 5773-5784.

Sambrook, Fritsch and Maniatis. Molecular Cloning—A Laboratory Manual. Cold Spring Press (Cold Spring Harbor, N.Y.). 1989.

Schnell, M. J., Mebatsion, T. and Conzelmann, K. K. (1994). Infectious rabies viruses from cloned cDNA. EMBO J. 13; 4195-4203.

Sidhu, M. S., Chan, J., Kaelin, K., Spielhofer, P., Radecke, F., Schreider, H., Masurekar, M., Dowling, P. C., Billeter, M. A. and Udem, S. A. (1995). Rescue of synthetic measles virus minireplicons: Measles genomic termini direct efficient expression and propagation of a reporter gene. Virology 208: 800-807.

Schneider, H., Speilhofer, P., Kaelin, K., Dotsch, C., Radecke, F., Sutter, G. and Billeter, M. (1997-February). Rescue of measles virus using a replication-deficient vaccinia-T7 vector. 64(1): 75-64.

Sutter, G., and Moss, B., (1992-November). Non-replicating vaccinia vector efficiently expresses recombinant genes. Proceedings of the National Academy of Sciences of the United States of America. 89(22): 10847-51.

Sutter, G., Ohlmann, M. and Erfle, V. Non-replicating vaccinia vector efficiently expressing bacteriophage T7 RNA polymerase.(1995-August). FEBS Letters 371 (1): 9-12.

Takeuchi, K., Tanabayashi, K., Hishiyama, M., Yamada, A. The mumps virus SH protein is a membrane protein and not essential for virus growth. Virology 225(1): 156-162, 1996.

Taniguchi, T., Palmieri, M., and Weissman, C. (1978). QB DNA-containing hybrid plasmids giving rise to QB phage formation in the bacterial host. Nature 274, 2293-2298.

Whelan, S. P., Ball, L. A., Barr, J. N. and Wertz, G. T. (1995). Efficient recovery of infectious vesicular stomatitis virus entirely from cDNA clones. Proc. Natl. Acad. Sci. USA 92; 8388-8392.

Wyatt, L. S., Moss, B. and Rozenblat, S. (1995-June). Replication-deficient vaccinia virus encoding bacteriophage T7 RNA polymerase for transient gene expression in mammalian cells. Virology. 210 (1); 202-5.

We claim:

1. A method for producing a recombinant mumps virus comprising;

in at least one host cell, conducting transfection or transformation, in media, of a rescue composition which comprises (i) a transcription vector comprising an isolated nucleic acid molecule which comprises a polynucleotide sequence encoding an antigenome of mumps virus, or variant polynucleotide sequence thereof, and (ii) at least one expression vector which comprises one more isolated nucleic acid molecule(s) comprising a polynucleotide sequence encoding the trans-acting proteins (NP, P and L) necessary for encapsidation, transcription and replication; under conditions sufficient to permit the co-expression of said vectors and the production of the recombinant virus;

wherein the isolated nucleic acid molecule encoding an antigenome of mumps virus comprises the polynucleotide sequence selected from the group consisting of SEQ. ID NOS. 1, 11 and 12;

and wherein the recombinant virus is harvested.

* * * * *

SEQUENCE LISTING

```
<160> NUMBER OF SEQ ID NOS: 12

<210> SEQ ID NO 1
<211> LENGTH: 15384
<212> TYPE: DNA
<213> ORGANISM: Mumps virus

<400> SEQUENCE: 1

accaagggga gaatgaatat gggatattgg tagaacaaat agtgtaagaa acagtaagcc     60

cggaagtggt gttttgcgat ttcgaggccg agctcgatcc tcaccttcca tcgtcgctag    120

ggggcatttt gacactacct ggaaaatgtc atctgtgctc aaggcatttg agcggttcac    180

gatagaacag gaacttcaag acaggggtga ggagggttca attccaccgg agactttaaa    240

gtcagcagtc aaagtcttcg ttattaacac acccaatccc accacacgct atcagatgct    300

aaacttttgc ttaagaataa tctgcagtca aaatgctagg gcatctcaca gggtaggtgc    360

attgataaca ttattctcac ttccctcagc aggcatgcaa aatcatatta gattagcaga    420

tagatcaccc gaagctcaga tagaacgctg tgagattgat ggttttgagc ctggtacata    480

taggctgatt ccaaatgcac gcgccaatct tactgccaat gaaattgctg cctatgcttt    540

gcttgcagat gacctccctc caaccataaa taatggaact ccttacgtac atgcagatgt    600

tgaaggacag ccatgtgatg agattgagca gttcctggat cggtgttaca gtgtactaat    660

ccaggcttgg gtaatggtct gtaaatgtat gacagcgtac gaccaacctg ccgggtctgc    720

tgatcggcga tttgcgaaat accagcagca aggtcgcctt gaggcaagat acatgctgca    780
```

-continued

```
accggaggcc caaaggttga ttcaaactgc catcaggaaa agtcttgttg ttagacagta    840
ccttaccttc gaactccagt tggcgagacg gcagggattg ctatcaaaca gatactatgc    900
aatggtgggt gacatcggaa agtacattga gaattcaggc cttactgcct tctttctcac    960
tctcaaatat gcactaggga ccaaatggag tcctctatca ttggctgcat tcaccggtga   1020
actcaccaag ctccgatcct tgatgatgtt atatcgaggt ctcggagaac aagccagata   1080
ccttgctctg ttagaggctc cccaaataat ggactttgca cccgggggct acccattgat   1140
attcagttat gctatgggag tcggtacagt cctagatgtt caaatgcgaa attacactta   1200
tgcacgacct ttcctaaacg gttattattt ccagattggg gttgagaccg cacgaagaca   1260
acaaggcact gttgacaaca gagtagcaga tgatctgggc ctgactcctg agcaaagaac   1320
tgaggtcact cagcttgttg acaggcttgc aaggggaaga ggtgctggga taccaggtgg   1380
gcctgtgaat ccttttgttc ctccggttca acagcaacaa cctgctgccg tatatgagga   1440
cattcctgca ttggaggaat cagatgacga tggtgatgaa gatggaggcg caggattcca   1500
aaatggagta caattaccag ctgtaagaca gggaggtcaa actgacttta gagcacagcc   1560
tttgcaagat ccaattcaag cacaactttt catgccatta tatcctcaag tcagcaacat   1620
gccaaataat cagaatcatc agatcaatcg catcgggggg ctggaacacc aagatttatt   1680
acgatacaac gagaatggtg attcccaaca agatgcaagg ggcgaacacg taaacacttt   1740
cccaaacaat cccaatcaaa acgcacagtt gcaagtggga gactgggatg agtaaatcac   1800
tgacatgatc aaactaaccc caatcgcaac aatcccagga caatccagcc acagctaact   1860
gcccaaatcc actacattcc attcatattt agtctttaag aaaaaattag gcccggaaag   1920
aattaggtcc acgatcacag gcacaatcat ttttatcgtg tttctttccg ggcaagccat   1980
ggatcaattt ataaaacagg atgagaccgg tgatttaatt gagacaggaa tgaatgttgc   2040
gaatcatttc ctatccaccc caattcaggg aaccaattcg ctgagcaagg cctcaatcct   2100
ccctggtgtt gcacctgtac tcattggcaa tccagagcaa aagaacattc agcaccctac   2160
cgcatcacat cagggatcca agacaaaggg cagaggctca ggagtcaggt ccatcatagt   2220
ctcaccctcc gaagcaggca atggagggac tcagattcct gagccccttt ttgcacaaac   2280
aggacagggt ggtatagtca ccacagttta ccaggatcca actatccaac caacaggttc   2340
ataccgaagt gtggaattgg cgaagatcgg aaaagagaga atgattaatc gatttgttga   2400
gaaacctaga acctcaacgc cggtgacaga atttaagagg ggggccggga gcggctgctc   2460
aaggccagac aatccaagag gagggcatag acgggaatgg agcctcagct gggtccaagg   2520
agaggtccgg gtctttgagt ggtgcaaccc tatatgctca cctatcactg ccgcagcaag   2580
attccactcc tgcaaatgtg ggaattgccc cgcaaagtgc gatcagtgcg aacgagatta   2640
tggacctcct taggggggatg gatgctcgcc tgcaacatct tgaacaaaag gtggacaagg   2700
tgcttgcaca gggcagcatg gtgacccaaa taaagaatga attatcaaca gtaaagacaa   2760
cattagcaac aattgaaggg atgatggcaa cagtaaagat catggatcct ggaaatccga   2820
caggggtccc agttgatgag cttagaagaa gttttagtga tcacgtgaca attgttagtg   2880
gaccaggaga tgtgtcgttc agctccagtg aaaaacccac actgtatttg gatgagctgg   2940
cgaggcccgt ctccaagcct cgtcctgcaa agcagacaaa atcccaacca gtaaaggatt   3000
tagcaggaca gaaagtgatg attaccaaaa tgatcactga ttgtgtggct aatcctcaaa   3060
tgaagcaggc gttcgagcaa cgattggcaa aggccagcac cgaggatgct ctgaacgata   3120
```

-continued

```
tcaagagaga catcatacga agcgccatat gaattcacca ggagcaccag actcaaggaa   3180
aaatctatga actgagagcc acaatgattc cctattaaat aaaaaataag cacgaacaca   3240
agtcaaatcc aaccatagca gaaatggcag gatcacagat caaaattcct cttccaaagc   3300
cccccgattc agactctcaa agactaaatg ccttccctgt catcatggct caagaaggca   3360
aaggacgact ccttagacaa atcaggctta ggaaaatatt atcaggggat ccgtctgatc   3420
agcaaattac atttgtgaat acatatggat tcatccgtgc cactccagaa acatccgagt   3480
tcatctctga atcatcacaa caaaaggtaa ctcctgtagt gacagcgtgc atgctgtcct   3540
ttggtgccgg accagtgcta gaagatccac aacatatgct caaggctctt gatcagacag   3600
acattagggt tcggaaaaca gcaagtgata aagagcagat cttattcgag atcaaccgca   3660
tccccaatct attcaggcat tatcaaatat ctgcggacca tctgattcag gccagctccg   3720
ataaatatgt caaatcacca gcaaaattga ttgcaggagt aaattacatc tactgtgtta   3780
cattcttatc tgtgacagtt tgttctgcct cactcaagtt tcgagttgcg cgcccattgc   3840
ttgctgcacg gtccagatta gtaagagcag ttcagatgga aattttgctt cgggtaactt   3900
gcaaaaaaga ttctcaaatg gcaaagagca tgttaaatga ccctgatgga gaagggtgca   3960
ttgcatccgt gtggttccac ctatgtaatc tgtgcaaagg cagaaataaa cttagaagtt   4020
acgatgaaaa ttattttgct tctaagtgcc gtaagatgaa tctgacagtc agcataggag   4080
atatgtgggg accaaccatt ctagtccatg caggcggtca cattccgaca actgcaaaac   4140
ctttttttcaa ctcaagaggc tgggtctgcc acccaatcca ccaatcatca ccatcgttgg   4200
cgaagaccct atggtcatct gggtgtgaaa tcaaggctgc cagtgctatt ctccagggtt   4260
cagactatgc atcacttgca aagactgatg acataatata ttcgaagata aaagtcgata   4320
aagacgcggc caactacaaa ggagtatcct ggagtccatt caggaagtct gcctcaatga   4380
gaaacctatg agaatttcct ctatttccac tgatgcctat aggagaatca acaatcaagc   4440
aaatttgacc ggtggtaatt cgattgaaat tatagaaaaa ataagcctag aaggatatcc   4500
tacttctcga ctttccaact ttgaaaatag aatagatcag taatcatgaa cgcttttcca   4560
gttatttgct tgggctatgc aatcttttca tcctctatat gtgtgaatat caataccttg   4620
cagcaaattg gatacatcaa gcaacaggtc aggcaactaa gctattactc acaaagttca   4680
agctcctacg tagtagtcaa gcttttaccg aatatccaac ccactgataa cagctgtgaa   4740
tttaagagtg taactcaata caataagacc ttgagtaatt tgctccttcc aattgcagaa   4800
aacataaaca atattgcatc gccctcactt gggtcaagac gtcataaacg gtttgctggc   4860
attgccattg gcattgctgc gctcggtgtt gcgaccgcag cacaagtgac tgccgctgtc   4920
tcattagttc aagcacagac aaatgcacgt gcaatagcag cgatgaaaaa ttcaatacag   4980
gcaactaatc gggcagtctt cgaagtgaag gaaggcaccc aacagttagc tatagcggta   5040
caagcaatac aagaccatat caatactatt atgagcaccc aattgaacaa tatgtcttgt   5100
cagatccttg ataaccaact tgcaacctcc ctaggattat acctaacaga attaacaaca   5160
gtgtttcagc cacaattaat taatccagca ttgtcaccga ttagtataca agccttgagg   5220
tctttgcttg gaagtatgac gcctgcagtg gttcaagcaa cattatctac ttcaatttct   5280
gctgctgaga tactaagtgc cggtctaatg gagggtcaga tagtttctgt tctgctagat   5340
gagatgcaga tgatagttaa gataaacatt ccaactattg tcacacaatc aaatgcattg   5400
gtgattgact tctactcaat ttcgagcttt attaataatc aagaatccat aattcaattg   5460
ccagacagga tcttggagat cgggaacgaa caatggcgct atccagctaa gaattgtaag   5520
```

-continued

```
ttgacaagac accacatgtt ctgccaatac aatgaggcag agaggctgag cctagaaaca   5580
aaactatgcc ttgcaggcaa tattagtgcc tgtgtgttct cacctatagc agggagttat   5640
atgaggcgat ttgtagcact ggatggaaca attgttgcaa actgccggag tctaacatgt   5700
ctatgtaaga gtccatctta tcctatatac caacctgacc atcatgcagt cacgaccatt   5760
gatctaacat catgtcaaac attgtccttg gacggactgg atttcagcat tgtctcgcta   5820
agcaatatca cttacactga gaatcttact atttcattgt ctcagacaat caatacccaa   5880
cccattgata tatcaactga gctgagtaag gttaatgcat cccttcaaaa tgccgttaaa   5940
tacataaaag aaagcaacca tcaactccaa tcctttagtg tgggttctaa aatcggagct   6000
ataattgtat cagccttggt tttgagcatc ctgtcgatta tcatttcgct attgttttgc   6060
tgctgggctt acattgcgac taaagaaatc agaagaatca acttcaaaac aaatcatatc   6120
aacacaatat caagtagtgt cgatgatctc atcaggtact aatcttagat tggtgattcg   6180
tcctgcaatt ttaaaagatt tagaaaaaaa ctaaaataag aatgaatctc ctagggtcgt   6240
aacgtctcgt gaccctgccg tcgcactatg ccggcaatcc aacctccctt atacctaaca   6300
tttctagtgc taatccttct ctatctcatc ataaccctgt atgtctggac tatattgact   6360
attaactata agacggcggt gcgatatgca gcactgtacc agcgatcctt ctctcgctgg   6420
ggttttgatc actcactcta gaaagatccc caattaggac aagtcccgat ccgtcacgct   6480
agaacaagct gcattcaaat gaagctgtgc taccatgaga cataaagaaa aaagcaagcc   6540
agaacaaacc taggatcata acacaataca gaatattagc tgctatcaca actgtgttcc   6600
ggccactaag aaaatggagc cctcgaaact atttataatg tcggacaatg ccacctttgc   6660
acctggacct gttgttaatg cggctggtaa gaagacattc cgaacctgtt tccgaatatt   6720
ggtcctatct gtacaagcag ttatccttat attggttatt gtcactttag gtgagcttat   6780
taggatgatc aatgatcaag gcttgagcaa tcagttgtct tcaattacag acaagataag   6840
agaatcagct gctgtgattg catctgctgt gggagtaatg aatcaagtta ttcatggagt   6900
aacggtatcc ttacctctac aaattgaggg taaccaaaat caattattat ccacacttgc   6960
tacaatctgc acaaacagaa atcaagtctc aaactgctcc acaaacatcc ccttaattaa   7020
tgaccttagg tttataaatg gaatcaataa attcatcatt gaagattatg caacccatga   7080
tttctccatc ggccatccac ttaacatgcc tagctttatc cccactgcaa cctcacccaa   7140
tggttgcacg agaattccat ccttttcttt aggtaagaca cactggtgtt acacacataa   7200
tgtaattaat gccaactgca aggatcatac ttcatccaac caatatgttt ccatggggat   7260
tcttgctcaa accgcgtcag ggtatcccat gttcaaaacc ctaaaaatcc aatatctcag   7320
tgatggcctg aatcggaaaa gctgctcaat tgcaacagtc cctgatggtt gcgcgatgta   7380
ctgttacgtt tcaactcaac ttgaaaccga cgactatgcg gggtccagcc cacctaccca   7440
gaaacttatc ctgttattct ataatgacac catcacagaa aggacaatat ctccatctgg   7500
tcttgaaggg aattgggcta ctttggtgcc aggagtgggg agtggaatat atttcgaaaa   7560
taagttgatc tttcctgcat acgggggtgt attgcccaat agtacactag gagttaaatt   7620
agcaagagaa tttttccggc ccgttaatcc atataatcca tgttcaggac cacaacaaga   7680
gttagatcag cgtgctttga gatcatattt cccaagttac ttctctagtc gacgggtaca   7740
gagtgcattt ctggtctgtg cttggaatca gatcctagtt acaaattgcg agctagttgt   7800
cccctcaaac aatcagacac tgatgggtgc agaaggaaga gttttattga tcaacaatcg   7860
```

-continued

```
actattatat tatcagagga gtactagctg gtggccgtat gaactcctct atgagatatc   7920
attcacattt acaaactacg gtcaatcatc tgtgaatatg tcctggatac ctatatattc   7980
attcactcgt cctggttcgg gccactgcag tggtgaaaat gtatgcccaa tagtctgtgt   8040
atcaggagtt tatcttgatc cctggccatt aactccatac agacaccaat caggcattaa   8100
cagaaatttc tatttcacag gtgcactgct aaattcaagc acaaccaggg tgaatcctac   8160
actttatgtc tctgccctta ataatcttaa agtactagcc ccatatggta ctcaaggatt   8220
gtttgcttca tacaccacaa ccacctgctt tcaagatacc ggcgacgcca gtgtgtattg   8280
tgtctatatt atggaactgg catcgaatat tgttggggaa ttccaaattc tacctgtgct   8340
agccagattg accatcactt gagttgtagt gaatgtagca ggaagcttta cgggcgtgtc   8400
tcatttctta ttgattatta agaaaaaaca ggccagaatg gcgggcctaa atgagatact   8460
cctacccgaa gtacatttaa actcccccat cgttagatat aagcttttct actatatatt   8520
gcatggccag ttaccaaatg acttggagcc ggatgacttg ggcccattag caaatcagaa   8580
ttggaaggca attcgagctg aagaatcaca ggttcatgca cgtttaaaac agatcagagt   8640
agaactcatt gcaaggattc ctagtctccg gtggacccga tctcaaagag agattgccat   8700
actcatttgg ccaagaatac ttccaatact gcaagcatat gatcttcggc aaagtatgca   8760
attgcccaca gtgtgggaga aactgactca atccacggtt aatcttataa gtgacggtct   8820
agaacgggtt gtattacaca tcagcaatca actaacaggc aagcctaact tgtttaccag   8880
atctcgagcc ggacaagaca caaaagatta ctcaattcca tccactagag agctatctca   8940
aatatggttc aacaatgagt ggagtgggtc tgtaaagacc tggcttatga ttaaatatag   9000
aatgaggcag ctaatcacaa atcaaaagac aggtgagtta acagatctag taaccattgt   9060
ggatactagg tccactctat gcattattac tccagaatta gtcgctttat actccagtga   9120
gcacaaagca ttaacgtacc tcacctttga aatggtatta atggtcactg atatgttaga   9180
gggacggctg aatgtttctt ctctgtgcac agctagtcat tatctgtccc ctttaaaaaa   9240
gagaatcgaa gttctcctga cattagttga tgaccttgca ctactcatgg gggataaagt   9300
atacggtatt gtctcttcac ttgagagttt tgtttacgcc caattacagt atggtgatcc   9360
tgttatagac attaaaggta cattctatgg atttatatgt aatgagattc tcgacctact   9420
gactgaagac aacatcttta ctgaagaaga ggctaataag gttcttctgg acttaacatc   9480
acaatttgac aatctatccc ctgatttaac tgctgagctc ctctgcatta tgagactttg   9540
gggccatccc accttaactg ccagccaagc agcatccaag gtccgagagt ccatgtgcgc   9600
tcctaaggta ttagactttc aaacaataat gaagaccctg gctttctttc acgcaatcct   9660
aattaacggt tataggagga gccataatgg aatctggccg cctaccactc ttcatggcaa   9720
tgcccccaaa agcctcattg agatgcggca tgataattca gagcttaagt atgagtatgt   9780
cctcaagaat tggaaaagta tatctatgtt aagaatacac aaatgctttg atgcatcacc   9840
tgatgaagat ctcagcatat tcatgaagga taaggcaata agctgtccaa ggcaagactg   9900
gatgggagta tttaggagga gcctgattaa acagcgctat cgtgacgcga atcggcctct   9960
accacaacca tttaaccgga gactgctgtt gaattttcta gaggatgacc gattcgatcc  10020
tattaaagag cttgagtatg tcaccagtgg agaatatctt agggaccctg aattttgtgc  10080
atcttactct ctcaaggaga aggagataaa ggctacaggt cgtatatttg caaaaatgac  10140
aaagagaatg agatcgtgcc aagtaattgc agaatcattg ttagccaatc acgcaggtaa  10200
attaatgaga gagaatgggg ttgtcttaga ccagttaaaa ttaacaaaat ctttattaac  10260
```

-continued

```
tatgaaccaa attggtatta tatcagagca cagccgaaga tccaccgctg acaacatgac  10320
tttagcacac tccggttcaa ataagcacag gattaataat agtcaattca agaagaataa  10380
agacaataaa catgagatgc ctgatgatgg gtttgagata gcagcctgct tcctaacaac  10440
tgacctcaca aaatactgct tgaattggag gtaccaggtc atcatcccct ttgcgcgtac  10500
attgaattca atgtatggta taccccactt gtttgaatgg atacatttaa ggctgatgcg  10560
aagcactctt tatgtcggtg atcccttcaa tcctccatca gatcctaccc aacttgacct  10620
tgatacagcc ctcaatgatg atatatttat agtttcccct cgtggcggaa tcgagggttt  10680
atgtcaaaaa ttatggacta tgatttccat ctcaacaatc atattgtccg caactgaggc  10740
aaacactaga gtaatgagca tggttcaggg cgataaccaa gcaattgcaa tcaccactag  10800
agtagtacgt tcgctcagtc attccgagaa gaaggagcaa gcctataaag caagtaaatt  10860
attctttgaa aggcttagag ctaacaacca tggaattgga caccacttaa aagaacaaga  10920
aacaatcctt agttctgatt tcttcattta cagtaagagg gtgttttaca aaggtcgaat  10980
cttgactcaa gcgttaaaga acgtgagcaa gatgtgctta acagctgata tactggggga  11040
ttgttcacaa gcatcatgct ccaatttagc taccactgta atgcgcctga ctgagaatgg  11100
ggtcgagaaa gatttgtgtt atttcctaaa tgcattcatg acaattagac aattatgtta  11160
tgatctagta tttccccaaa ctaaatctct tagtcaggac attactaatg cttatcttaa  11220
tcatccaata cttatctcaa gattgtgtct attaccatct caattggggg gcttaaactt  11280
tctttcatgt agtcgcctgt ttaatagaaa cataggagat ccactagtgt ctgcaattgc  11340
tgatgtgaaa cgattaatta aagcgggctg tctagatatc tgggtcctgt acaacatcct  11400
tggaaggagg ccaggaaaag gtaagtggag cactctggca gctgatccct atactttaaa  11460
catagattat ttagtccctt caacaacttt tttgaagaaa catgcccaat atacattgat  11520
ggaacggagt gttaatccca tgctccgcgg agtatttagt gaaaatgcag cagaggagga  11580
agaagaactc gcacagtatc tattagatcg cgaagtagtc atgcccaggg ttgcacatgt  11640
tatacttgct cagtctagtt gcggtagaag aaaacagatc caaggttact tggattctac  11700
tagaactatt attaggtatt cactggaggt aaggccactg tcagcaaaga agctgaatac  11760
agtaatagaa tataacttat tgtacctgtc ctacaatttg gagattattg aaaaacccaa  11820
tatagtccaa cctttttga atgcaatcaa tgttgatact tgtagcatcg atatagctag  11880
gtcccttaga aaattatcct gggcaacttt acttaatgga cgtcccatcg agggattaga  11940
aacacctgat cctattgaat tggtacatgg gtgtttaata atcgggtcag atgagtgtga  12000
gcattgcagt agtggtgatg acaaattcac ctggtttttc ctccctaagg ggataaggtt  12060
agatgatgat ccggcatcta acccacccat cagagtacct tatatcggat ccaaaacaga  12120
tgaacgaagg gttgcatcaa tggcttatat caaaggggca tcagtatcac ttaaatcagc  12180
actcagatta gcgggggtat atatatgggc tttcggagat acagaggaat catggcagga  12240
tgcctatgag ttagcttcca ctcgtgttaa tctcacacta gagcaattgc aatctctcac  12300
tcctttacca acatctgcca acttagtcca cagattggat gatggcacta ctcaattaaa  12360
atttacccca gcaagctcct atgcattctc tagctttgtt catatatcta acgactgtca  12420
aattcttgag atcgatgatc aggtaacgga ttctaacctg atttaccagc aagtcatgat  12480
tactggcctt gctctaattg agacatggaa taatcctcca atcaacttct ccgtttatga  12540
aaccacatta cacttgcaca caggctcatc ttgctgtata agacctgtcg agtcttgtgt  12600
```

-continued

```
agtaaatccg cctttacttc ctgtccctct cattaatgtt cctcaaatga ataaatttgt  12660
atatgatcct gaaccactta gtttgttaga aatggaaaaa attgaggata ttgcttatca  12720
aaccagaatt ggtggtttag atcaaatccc gcttctggaa aaaataccct tactagctca  12780
ccttaccgcc aagcagatgg taaatagcat cactgggctt gatgaagcaa catctataat  12840
gaatgatgct gtagttcaag cagactatac tagcaattgg attagtgaat gctgctatac  12900
ttacattgac tctgtgtttg tttactccgg ctgggcatta ttattggaac tttcatacca  12960
aatgtattac ctaagaattc aaggcataca aggaatccta gactatgtgt atatgacctt  13020
gaggaggata ccaggaatgg ccataacagg catctcatcc acaattagtc accctcgtat  13080
actcagaaga tgcatcaatt tggatgtcat agccccaatc aattctccac acatagcttc  13140
actggattac acaaaattga gcatagatgc agtaatgtgg ggaaccaagc aggtgttgac  13200
caacatttcg caaggtatcg attatgagat agttgttcct tctgaaagcc aacttacact  13260
cagtgataga gtcctaaatc tagttgctcg aaaattatca ctactggcaa tcatctgggc  13320
caattacaac tatcctccga aggttaaagg tatgtcacct gaagacaaat gtcaggcttt  13380
aactacacat ctactccaaa ctgttgaata tgtcgagtac attcagattg aaaagacaaa  13440
catcaggagg atgattattg agccaaaatt aactgcctac cctagtaatt tgttttacct  13500
ctctcgaaag ctgcttaatg ctattcgaga ctcagaagaa ggacaattcc tgattgcatc  13560
ctattataac agttttggat atctggaacc gatattaatg gaatctaaaa tattcaatct  13620
gagttcatcc gaatcagcat ctcttacaga atttgatttc atcctcaact tggaattgtc  13680
cgacgccagc cttgagaaat actctctccc aagtttgctt atgacggctg agaatatgga  13740
taacccattt cctcaacccc cacttcatca cgttctcaga ccactaggtt tgtcatccac  13800
ctcatggtat aaaacaatca gtgttttaaa ttatattagc catatgaaga tatctgacgg  13860
tgcccatcta tacttggcag agggaagtgg agcctctatg tcacttatag aaactttctt  13920
gcccggggaa acaatatggt acaacagcct gttcaatagt ggtgagaatc cccctcaacg  13980
taatttcgcc cctttgccca cccagtttat tgaaagtgtc ccctatagat tgattcaggc  14040
aggtatagca gcaggaaatg gcatagtgca aagtttctat ccgctctgga acggaaacag  14100
cgatataact gacttaagca cgaaaactag tgttgaatac attatccaca aggtaggagc  14160
tgatacttgt gcattagttc atgtggattt ggaaggtgta cctggctcaa tgaacagcat  14220
gttggagaga gctcaagtac atgcgctgct aattacagtg actgtattaa aaccaggcgg  14280
cttactaatc ttgaaagctt catgggaacc ttttaatcga ttttcctttt tactcacagt  14340
actctggcaa ttcttttcca caattaggat cttgcgatct tcatactccg atccgaataa  14400
tcacgaggtt tacataatag ccacattggc agttgatccc accacatcct cctttacaac  14460
tgctctgaat agggcacgca ccctgaatga acagggcttt tcactcatcc cacctgaatt  14520
agtgagtgag tactggagga agcgtgttga acaaggacag attatacagg actgtataga  14580
taaagttata tcagagtgtg tcagagatca atatctggca gacaacaaca ttatcctcca  14640
agcgggaggt actccgagca caagaaaatg gttggatctt cctgactatt cttcgttcaa  14700
tgaattacaa tctgaaatgg ccagactcat aacaattcat cttaaagagg taatagaaat  14760
cctaaagggc caagcatcag atcatgacac cctattattt acttcataca acgtaggtcc  14820
cctcggaaaa ataaatacaa tactcagatt gattgttgag agaattctta tgtatactgt  14880
gaggaactgg tgtatcttgc ctacccaaac tcgtctcacc ttacgacaat ctatcgagct  14940
tggagagttt agactaagag atgtgataac acccatggag attctaaaac tatcccccaa  15000
```

-continued

```
caggaaatat ctgaagtctg cattaaatca atcaacattc aatcatctaa tgggagaaac  15060

atctgacata ttgttaaacc gagcttatca gaagagaatt tggaaagcta ttgggtgtgt  15120

aatctattgc tttggtttgc tcaccccaga tgttgaaggt tctgagcgca ttgatgttga  15180

taatgacata cctgattatg atattcacgg ggacataatt taaatcgact aaagactcct  15240

ctggcattac acatcaccaa aaagtgccga actaacatcc aaattcttct aaaccgcaca  15300

cgacctcgaa caatcataac cacatcagta ttaaatctag gagatccttt taagaaaaaa  15360

ttgattttac tttctcccct tggt                                         15384


<210> SEQ ID NO 2
<211> LENGTH: 549
<212> TYPE: PRT
<213> ORGANISM: Mumps virus

<400> SEQUENCE: 2

Met Ser Ser Val Leu Lys Ala Phe Glu Arg Phe Thr Ile Glu Gln Glu
  1               5                  10                  15

Leu Gln Asp Arg Gly Glu Glu Gly Ser Ile Pro Pro Glu Thr Leu Lys
             20                  25                  30

Ser Ala Val Lys Val Phe Val Ile Asn Thr Pro Asn Pro Thr Thr Arg
         35                  40                  45

Tyr Gln Met Leu Asn Phe Cys Leu Arg Ile Ile Cys Ser Gln Asn Ala
     50                  55                  60

Arg Ala Ser His Arg Val Gly Ala Leu Ile Thr Leu Phe Ser Leu Pro
 65                  70                  75                  80

Ser Ala Gly Met Gln Asn His Ile Arg Leu Ala Asp Arg Ser Pro Glu
                 85                  90                  95

Ala Gln Ile Glu Arg Cys Glu Ile Asp Gly Phe Glu Pro Gly Thr Tyr
            100                 105                 110

Arg Leu Ile Pro Asn Ala Arg Ala Asn Leu Thr Ala Asn Glu Ile Ala
        115                 120                 125

Ala Tyr Ala Leu Leu Ala Asp Asp Leu Pro Pro Thr Ile Asn Asn Gly
    130                 135                 140

Thr Pro Tyr Val His Ala Asp Val Glu Gly Gln Pro Cys Asp Glu Ile
145                 150                 155                 160

Glu Gln Phe Leu Asp Arg Cys Tyr Ser Val Leu Ile Gln Ala Trp Val
                165                 170                 175

Met Val Cys Lys Cys Met Thr Ala Tyr Asp Gln Pro Ala Gly Ser Ala
            180                 185                 190

Asp Arg Arg Phe Ala Lys Tyr Gln Gln Gln Gly Arg Leu Glu Ala Arg
        195                 200                 205

Tyr Met Leu Gln Pro Glu Ala Gln Arg Leu Ile Gln Thr Ala Ile Arg
    210                 215                 220

Lys Ser Leu Val Val Arg Gln Tyr Leu Thr Phe Glu Leu Gln Leu Ala
225                 230                 235                 240

Arg Arg Gln Gly Leu Leu Ser Asn Arg Tyr Tyr Ala Met Val Gly Asp
                245                 250                 255

Ile Gly Lys Tyr Ile Glu Asn Ser Gly Leu Thr Ala Phe Phe Leu Thr
            260                 265                 270

Leu Lys Tyr Ala Leu Gly Thr Lys Trp Ser Pro Leu Ser Leu Ala Ala
        275                 280                 285

Phe Thr Gly Glu Leu Thr Lys Leu Arg Ser Leu Met Met Leu Tyr Arg
    290                 295                 300
```

-continued

Gly Leu Gly Glu Gln Ala Arg Tyr Leu Ala Leu Leu Glu Ala Pro Gln
305 310 315 320

Ile Met Asp Phe Ala Pro Gly Gly Tyr Pro Leu Ile Phe Ser Tyr Ala
325 330 335

Met Gly Val Gly Thr Val Leu Asp Val Gln Met Arg Asn Tyr Thr Tyr
340 345 350

Ala Arg Pro Phe Leu Asn Gly Tyr Tyr Phe Gln Ile Gly Val Glu Thr
355 360 365

Ala Arg Arg Gln Gln Gly Thr Val Asp Asn Arg Val Ala Asp Asp Leu
370 375 380

Gly Leu Thr Pro Glu Gln Arg Thr Glu Val Thr Gln Leu Val Asp Arg
385 390 395 400

Leu Ala Arg Gly Arg Gly Ala Gly Ile Pro Gly Gly Pro Val Asn Pro
405 410 415

Phe Val Pro Pro Val Gln Gln Gln Gln Pro Ala Ala Val Tyr Glu Asp
420 425 430

Ile Pro Ala Leu Glu Glu Ser Asp Asp Asp Gly Asp Glu Asp Gly Gly
435 440 445

Ala Gly Phe Gln Asn Gly Val Gln Leu Pro Ala Val Arg Gln Gly Gly
450 455 460

Gln Thr Asp Phe Arg Ala Gln Pro Leu Gln Asp Pro Ile Gln Ala Gln
465 470 475 480

Leu Phe Met Pro Leu Tyr Pro Gln Val Ser Asn Met Pro Asn Asn Gln
485 490 495

Asn His Gln Ile Asn Arg Ile Gly Gly Leu Glu His Gln Asp Leu Leu
500 505 510

Arg Tyr Asn Glu Asn Gly Asp Ser Gln Gln Asp Ala Arg Gly Glu His
515 520 525

Val Asn Thr Phe Pro Asn Asn Pro Asn Gln Asn Ala Gln Leu Gln Val
530 535 540

Gly Asp Trp Asp Glu
545

<210> SEQ ID NO 3
<211> LENGTH: 391
<212> TYPE: PRT
<213> ORGANISM: Mumps virus

<400> SEQUENCE: 3

Met Asp Gln Phe Ile Lys Gln Asp Glu Thr Gly Asp Leu Ile Glu Thr
1 5 10 15

Gly Met Asn Val Ala Asn His Phe Leu Ser Thr Pro Ile Gln Gly Thr
20 25 30

Asn Ser Leu Ser Lys Ala Ser Ile Leu Pro Gly Val Ala Pro Val Leu
35 40 45

Ile Gly Asn Pro Glu Gln Lys Asn Ile Gln His Pro Thr Ala Ser His
50 55 60

Gln Gly Ser Lys Thr Lys Gly Arg Gly Ser Gly Val Arg Ser Ile Ile
65 70 75 80

Val Ser Pro Ser Glu Ala Gly Asn Gly Gly Thr Gln Ile Pro Glu Pro
85 90 95

Leu Phe Ala Gln Thr Gly Gln Gly Gly Ile Val Thr Thr Val Tyr Gln
100 105 110

Asp Pro Thr Ile Gln Pro Thr Gly Ser Tyr Arg Ser Val Glu Leu Ala

-continued

```
        115                 120                 125

Lys Ile Gly Lys Glu Arg Met Ile Asn Arg Phe Val Glu Lys Pro Arg
    130                 135                 140

Thr Ser Thr Pro Val Thr Glu Phe Lys Arg Gly Gly Pro Gly Ala Ala
145                 150                 155                 160

Ala Gln Gly Gln Thr Ile Gln Glu Glu Gly Ile Asp Gly Asn Gly Ala
                165                 170                 175

Ser Ala Gly Ser Lys Glu Arg Ser Gly Ser Leu Ser Gly Ala Thr Leu
            180                 185                 190

Tyr Ala His Leu Ser Leu Pro Gln Gln Asp Ser Thr Pro Ala Asn Val
        195                 200                 205

Gly Ile Ala Pro Gln Ser Ala Ile Ser Ala Asn Glu Ile Met Asp Leu
    210                 215                 220

Leu Arg Gly Met Asp Ala Arg Leu Gln His Leu Glu Gln Lys Val Asp
225                 230                 235                 240

Lys Val Leu Ala Gln Gly Ser Met Val Thr Gln Ile Lys Asn Glu Leu
                245                 250                 255

Ser Thr Val Lys Thr Thr Leu Ala Thr Ile Glu Gly Met Met Ala Thr
            260                 265                 270

Val Lys Ile Met Asp Pro Gly Asn Pro Thr Gly Val Pro Val Asp Glu
        275                 280                 285

Leu Arg Arg Ser Phe Ser Asp His Val Thr Ile Val Ser Gly Pro Gly
    290                 295                 300

Asp Val Ser Phe Ser Ser Ser Glu Lys Pro Thr Leu Tyr Leu Asp Glu
305                 310                 315                 320

Leu Ala Arg Pro Val Ser Lys Pro Arg Pro Ala Lys Gln Thr Lys Ser
                325                 330                 335

Gln Pro Val Lys Asp Leu Ala Gly Gln Lys Val Met Ile Thr Lys Met
            340                 345                 350

Ile Thr Asp Cys Val Ala Asn Pro Gln Met Lys Gln Ala Phe Glu Gln
        355                 360                 365

Arg Leu Ala Lys Ala Ser Thr Glu Asp Ala Leu Asn Asp Ile Lys Arg
    370                 375                 380

Asp Ile Ile Arg Ser Ala Ile
385                 390


<210> SEQ ID NO 4
<211> LENGTH: 171
<212> TYPE: PRT
<213> ORGANISM: Mumps virus

<400> SEQUENCE: 4

Met Asp Gln Phe Ile Lys Gln Asp Glu Thr Gly Asp Leu Ile Glu Thr
  1               5                  10                  15

Gly Met Asn Val Ala Asn His Phe Leu Ser Thr Pro Ile Gln Gly Thr
             20                  25                  30

Asn Ser Leu Ser Lys Ala Ser Ile Leu Pro Gly Val Ala Pro Val Leu
         35                  40                  45

Ile Gly Asn Pro Glu Gln Lys Asn Ile Gln His Pro Thr Ala Ser His
     50                  55                  60

Gln Gly Ser Lys Thr Lys Gly Arg Gly Ser Gly Val Arg Ser Ile Ile
 65                  70                  75                  80

Val Ser Pro Ser Glu Ala Gly Asn Gly Gly Thr Gln Ile Pro Glu Pro
                 85                  90                  95
```

```
Leu Phe Ala Gln Thr Gly Gln Gly Gly Ile Val Thr Thr Val Tyr Gln
            100                 105                 110

Asp Pro Thr Ile Gln Pro Thr Gly Ser Tyr Arg Ser Val Glu Leu Ala
        115                 120                 125

Lys Ile Gly Lys Glu Arg Met Ile Asn Arg Phe Val Glu Lys Pro Arg
    130                 135                 140

Thr Ser Thr Pro Val Thr Glu Phe Lys Arg Gly Gly Gly Arg Glu Arg
145                 150                 155                 160

Leu Leu Lys Ala Arg Gln Ser Lys Arg Arg Ala
                165                 170


<210> SEQ ID NO 5
<211> LENGTH: 224
<212> TYPE: PRT
<213> ORGANISM: Mumps virus

<400> SEQUENCE: 5

Met Asp Gln Phe Ile Lys Gln Asp Glu Thr Gly Asp Leu Ile Glu Thr
  1               5                  10                  15

Gly Met Asn Val Ala Asn His Phe Leu Ser Thr Pro Ile Gln Gly Thr
             20                  25                  30

Asn Ser Leu Ser Lys Ala Ser Ile Leu Pro Gly Val Ala Pro Val Leu
         35                  40                  45

Ile Gly Asn Pro Glu Gln Lys Asn Ile Gln His Pro Thr Ala Ser His
     50                  55                  60

Gln Gly Ser Lys Thr Lys Gly Arg Gly Ser Gly Val Arg Ser Ile Ile
 65                  70                  75                  80

Val Ser Pro Ser Glu Ala Gly Asn Gly Gly Thr Gln Ile Pro Glu Pro
                 85                  90                  95

Leu Phe Ala Gln Thr Gly Gln Gly Gly Ile Val Thr Thr Val Tyr Gln
            100                 105                 110

Asp Pro Thr Ile Gln Pro Thr Gly Ser Tyr Arg Ser Val Glu Leu Ala
        115                 120                 125

Lys Ile Gly Lys Glu Arg Met Ile Asn Arg Phe Val Glu Lys Pro Arg
    130                 135                 140

Thr Ser Thr Pro Val Thr Glu Phe Lys Arg Gly Ala Gly Ser Gly Cys
145                 150                 155                 160

Ser Arg Pro Asp Asn Pro Arg Gly Gly His Arg Arg Glu Trp Ser Leu
                165                 170                 175

Ser Trp Val Gln Gly Glu Val Arg Val Phe Glu Trp Cys Asn Pro Ile
            180                 185                 190

Cys Ser Pro Ile Thr Ala Ala Ala Arg Phe His Ser Cys Lys Cys Gly
        195                 200                 205

Asn Cys Pro Ala Lys Cys Asp Gln Cys Glu Arg Asp Tyr Gly Pro Pro
    210                 215                 220


<210> SEQ ID NO 6
<211> LENGTH: 375
<212> TYPE: PRT
<213> ORGANISM: Mumps virus

<400> SEQUENCE: 6

Met Ala Gly Ser Gln Ile Lys Ile Pro Leu Pro Lys Pro Pro Asp Ser
  1               5                  10                  15

Asp Ser Gln Arg Leu Asn Ala Phe Pro Val Ile Met Ala Gln Glu Gly
             20                  25                  30
```

-continued

```
Lys Gly Arg Leu Leu Arg Gln Ile Arg Leu Arg Lys Ile Leu Ser Gly
        35                  40                  45

Asp Pro Ser Asp Gln Gln Ile Thr Phe Val Asn Thr Tyr Gly Phe Ile
    50                  55                  60

Arg Ala Thr Pro Glu Thr Ser Glu Phe Ile Ser Glu Ser Ser Gln Gln
65                  70                  75                  80

Lys Val Thr Pro Val Val Thr Ala Cys Met Leu Ser Phe Gly Ala Gly
                85                  90                  95

Pro Val Leu Glu Asp Pro Gln His Met Leu Lys Ala Leu Asp Gln Thr
            100                 105                 110

Asp Ile Arg Val Arg Lys Thr Ala Ser Asp Lys Glu Gln Ile Leu Phe
        115                 120                 125

Glu Ile Asn Arg Ile Pro Asn Leu Phe Arg His Tyr Gln Ile Ser Ala
    130                 135                 140

Asp His Leu Ile Gln Ala Ser Ser Asp Lys Tyr Val Lys Ser Pro Ala
145                 150                 155                 160

Lys Leu Ile Ala Gly Val Asn Tyr Ile Tyr Cys Val Thr Phe Leu Ser
                165                 170                 175

Val Thr Val Cys Ser Ala Ser Leu Lys Phe Arg Val Ala Arg Pro Leu
            180                 185                 190

Leu Ala Ala Arg Ser Arg Leu Val Arg Ala Val Gln Met Glu Ile Leu
        195                 200                 205

Leu Arg Val Thr Cys Lys Lys Asp Ser Gln Met Ala Lys Ser Met Leu
    210                 215                 220

Asn Asp Pro Asp Gly Glu Gly Cys Ile Ala Ser Val Trp Phe His Leu
225                 230                 235                 240

Cys Asn Leu Cys Lys Gly Arg Asn Lys Leu Arg Ser Tyr Asp Glu Asn
                245                 250                 255

Tyr Phe Ala Ser Lys Cys Arg Lys Met Asn Leu Thr Val Ser Ile Gly
            260                 265                 270

Asp Met Trp Gly Pro Thr Ile Leu Val His Ala Gly Gly His Ile Pro
        275                 280                 285

Thr Thr Ala Lys Pro Phe Phe Asn Ser Arg Gly Trp Val Cys His Pro
    290                 295                 300

Ile His Gln Ser Ser Pro Ser Leu Ala Lys Thr Leu Trp Ser Ser Gly
305                 310                 315                 320

Cys Glu Ile Lys Ala Ala Ser Ala Ile Leu Gln Gly Ser Asp Tyr Ala
                325                 330                 335

Ser Leu Ala Lys Thr Asp Asp Ile Ile Tyr Ser Lys Ile Lys Val Asp
            340                 345                 350

Lys Asp Ala Ala Asn Tyr Lys Gly Val Ser Trp Ser Pro Phe Arg Lys
        355                 360                 365

Ser Ala Ser Met Arg Asn Leu
    370                 375


<210> SEQ ID NO 7
<211> LENGTH: 538
<212> TYPE: PRT
<213> ORGANISM: Mumps virus

<400> SEQUENCE: 7

Met Asn Ala Phe Pro Val Ile Cys Leu Gly Tyr Ala Ile Phe Ser Ser
  1               5                  10                  15

Ser Ile Cys Val Asn Ile Asn Thr Leu Gln Gln Ile Gly Tyr Ile Lys
             20                  25                  30
```

-continued

```
Gln Gln Val Arg Gln Leu Ser Tyr Tyr Ser Gln Ser Ser Ser Ser Tyr
        35                  40                  45

Val Val Val Lys Leu Leu Pro Asn Ile Gln Pro Thr Asp Asn Ser Cys
    50                  55                  60

Glu Phe Lys Ser Val Thr Gln Tyr Asn Lys Thr Leu Ser Asn Leu Leu
 65                  70                  75                  80

Leu Pro Ile Ala Glu Asn Ile Asn Asn Ile Ala Ser Pro Ser Leu Gly
                85                  90                  95

Ser Arg Arg His Lys Arg Phe Ala Gly Ile Ala Ile Gly Ile Ala Ala
            100                 105                 110

Leu Gly Val Ala Thr Ala Ala Gln Val Thr Ala Ala Val Ser Leu Val
        115                 120                 125

Gln Ala Gln Thr Asn Ala Arg Ala Ile Ala Ala Met Lys Asn Ser Ile
    130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Ser Thr Gln Leu Asn Asn Met Ser Cys Gln Ile Leu Asp Asn Gln Leu
            180                 185                 190

Ala Thr Ser Leu Gly Leu Tyr Leu Thr Glu Leu Thr Thr Val Phe Gln
        195                 200                 205

Pro Gln Leu Ile Asn Pro Ala Leu Ser Pro Ile Ser Ile Gln Ala Leu
    210                 215                 220

Arg Ser Leu Leu Gly Ser Met Thr Pro Ala Val Val Gln Ala Thr Leu
225                 230                 235                 240

Ser Thr Ser Ile Ser Ala Ala Glu Ile Leu Ser Ala Gly Leu Met Glu
                245                 250                 255

Gly Gln Ile Val Ser Val Leu Leu Asp Glu Met Gln Met Ile Val Lys
            260                 265                 270

Ile Asn Ile Pro Thr Ile Val Thr Gln Ser Asn Ala Leu Val Ile Asp
        275                 280                 285

Phe Tyr Ser Ile Ser Ser Phe Ile Asn Asn Gln Glu Ser Ile Ile Gln
    290                 295                 300

Leu Pro Asp Arg Ile Leu Glu Ile Gly Asn Glu Gln Trp Arg Tyr Pro
305                 310                 315                 320

Ala Lys Asn Cys Lys Leu Thr Arg His His Met Phe Cys Gln Tyr Asn
                325                 330                 335

Glu Ala Glu Arg Leu Ser Leu Glu Thr Lys Leu Cys Leu Ala Gly Asn
            340                 345                 350

Ile Ser Ala Cys Val Phe Ser Pro Ile Ala Gly Ser Tyr Met Arg Arg
        355                 360                 365

Phe Val Ala Leu Asp Gly Thr Ile Val Ala Asn Cys Arg Ser Leu Thr
    370                 375                 380

Cys Leu Cys Lys Ser Pro Ser Tyr Pro Ile Tyr Gln Pro Asp His His
385                 390                 395                 400

Ala Val Thr Thr Ile Asp Leu Thr Ser Cys Gln Thr Leu Ser Leu Asp
                405                 410                 415

Gly Leu Asp Phe Ser Ile Val Ser Leu Ser Asn Ile Thr Tyr Thr Glu
            420                 425                 430

Asn Leu Thr Ile Ser Leu Ser Gln Thr Ile Asn Thr Gln Pro Ile Asp
        435                 440                 445
```

-continued

```
Ile Ser Thr Glu Leu Ser Lys Val Asn Ala Ser Leu Gln Asn Ala Val
    450                 455                 460

Lys Tyr Ile Lys Glu Ser Asn His Gln Leu Gln Ser Phe Ser Val Gly
465                 470                 475                 480

Ser Lys Ile Gly Ala Ile Ile Val Ser Ala Leu Val Leu Ser Ile Leu
                485                 490                 495

Ser Ile Ile Ile Ser Leu Leu Phe Cys Cys Trp Ala Tyr Ile Ala Thr
            500                 505                 510

Lys Glu Ile Arg Arg Ile Asn Phe Lys Thr Asn His Ile Asn Thr Ile
        515                 520                 525

Ser Ser Ser Val Asp Asp Leu Ile Arg Tyr
    530                 535
```

<210> SEQ ID NO 8
<211> LENGTH: 57
<212> TYPE: PRT
<213> ORGANISM: Mumps virus

<400> SEQUENCE: 8

```
Met Pro Ala Ile Gln Pro Pro Leu Tyr Leu Thr Phe Leu Val Leu Ile
  1               5                  10                  15

Leu Leu Tyr Leu Ile Ile Thr Leu Tyr Val Trp Thr Ile Leu Thr Ile
             20                  25                  30

Asn Tyr Lys Thr Ala Val Arg Tyr Ala Ala Leu Tyr Gln Arg Ser Phe
         35                  40                  45

Ser Arg Trp Gly Phe Asp His Ser Leu
     50                  55
```

<210> SEQ ID NO 9
<211> LENGTH: 582
<212> TYPE: PRT
<213> ORGANISM: Mumps virus

<400> SEQUENCE: 9

```
Met Glu Pro Ser Lys Leu Phe Ile Met Ser Asp Asn Ala Thr Phe Ala
  1               5                  10                  15

Pro Gly Pro Val Val Asn Ala Ala Gly Lys Lys Thr Phe Arg Thr Cys
             20                  25                  30

Phe Arg Ile Leu Val Leu Ser Val Gln Ala Val Ile Leu Ile Leu Val
         35                  40                  45

Ile Val Thr Leu Gly Glu Leu Ile Arg Met Ile Asn Asp Gln Gly Leu
     50                  55                  60

Ser Asn Gln Leu Ser Ser Ile Thr Asp Lys Ile Arg Glu Ser Ala Ala
 65                  70                  75                  80

Val Ile Ala Ser Ala Val Gly Val Met Asn Gln Val Ile His Gly Val
                 85                  90                  95

Thr Val Ser Leu Pro Leu Gln Ile Glu Gly Asn Gln Asn Gln Leu Leu
            100                 105                 110

Ser Thr Leu Ala Thr Ile Cys Thr Asn Arg Asn Gln Val Ser Asn Cys
        115                 120                 125

Ser Thr Asn Ile Pro Leu Ile Asn Asp Leu Arg Phe Ile Asn Gly Ile
    130                 135                 140

Asn Lys Phe Ile Ile Glu Asp Tyr Ala Thr His Asp Phe Ser Ile Gly
145                 150                 155                 160

His Pro Leu Asn Met Pro Ser Phe Ile Pro Thr Ala Thr Ser Pro Asn
                165                 170                 175
```

-continued

```
Gly Cys Thr Arg Ile Pro Ser Phe Ser Leu Gly Lys Thr His Trp Cys
            180                 185                 190

Tyr Thr His Asn Val Ile Asn Ala Asn Cys Lys Asp His Thr Ser Ser
        195                 200                 205

Asn Gln Tyr Val Ser Met Gly Ile Leu Ala Gln Thr Ala Ser Gly Tyr
    210                 215                 220

Pro Met Phe Lys Thr Leu Lys Ile Gln Tyr Leu Ser Asp Gly Leu Asn
225                 230                 235                 240

Arg Lys Ser Cys Ser Ile Ala Thr Val Pro Asp Gly Cys Ala Met Tyr
                245                 250                 255

Cys Tyr Val Ser Thr Gln Leu Glu Thr Asp Asp Tyr Ala Gly Ser Ser
            260                 265                 270

Pro Pro Thr Gln Lys Leu Ile Leu Leu Phe Tyr Asn Asp Thr Ile Thr
        275                 280                 285

Glu Arg Thr Ile Ser Pro Ser Gly Leu Glu Gly Asn Trp Ala Thr Leu
    290                 295                 300

Val Pro Gly Val Gly Ser Gly Ile Tyr Phe Glu Asn Lys Leu Ile Phe
305                 310                 315                 320

Pro Ala Tyr Gly Gly Val Leu Pro Asn Ser Thr Leu Gly Val Lys Leu
                325                 330                 335

Ala Arg Glu Phe Phe Arg Pro Val Asn Pro Tyr Asn Pro Cys Ser Gly
            340                 345                 350

Pro Gln Gln Glu Leu Asp Gln Arg Ala Leu Arg Ser Tyr Phe Pro Ser
        355                 360                 365

Tyr Phe Ser Ser Arg Arg Val Gln Ser Ala Phe Leu Val Cys Ala Trp
    370                 375                 380

Asn Gln Ile Leu Val Thr Asn Cys Glu Leu Val Val Pro Ser Asn Asn
385                 390                 395                 400

Gln Thr Leu Met Gly Ala Glu Gly Arg Val Leu Leu Ile Asn Asn Arg
                405                 410                 415

Leu Leu Tyr Tyr Gln Arg Ser Thr Ser Trp Trp Pro Tyr Glu Leu Leu
            420                 425                 430

Tyr Glu Ile Ser Phe Thr Phe Thr Asn Tyr Gly Gln Ser Ser Val Asn
        435                 440                 445

Met Ser Trp Ile Pro Ile Tyr Ser Phe Thr Arg Pro Gly Ser Gly His
    450                 455                 460

Cys Ser Gly Glu Asn Val Cys Pro Ile Val Cys Val Ser Gly Val Tyr
465                 470                 475                 480

Leu Asp Pro Trp Pro Leu Thr Pro Tyr Arg His Gln Ser Gly Ile Asn
                485                 490                 495

Arg Asn Phe Tyr Phe Thr Gly Ala Leu Leu Asn Ser Ser Thr Thr Arg
            500                 505                 510

Val Asn Pro Thr Leu Tyr Val Ser Ala Leu Asn Asn Leu Lys Val Leu
        515                 520                 525

Ala Pro Tyr Gly Thr Gln Gly Leu Phe Ala Ser Tyr Thr Thr Thr Thr
    530                 535                 540

Cys Phe Gln Asp Thr Gly Asp Ala Ser Val Tyr Cys Val Tyr Ile Met
545                 550                 555                 560

Glu Leu Ala Ser Asn Ile Val Gly Glu Phe Gln Ile Leu Pro Val Leu
                565                 570                 575

Ala Arg Leu Thr Ile Thr
            580
```

-continued

<210> SEQ ID NO 10
<211> LENGTH: 2261
<212> TYPE: PRT
<213> ORGANISM: Mumps virus

<400> SEQUENCE: 10

```
Met Ala Gly Leu Asn Glu Ile Leu Leu Pro Glu Val His Leu Asn Ser
  1               5                  10                  15

Pro Ile Val Arg Tyr Lys Leu Phe Tyr Tyr Ile Leu His Gly Gln Leu
             20                  25                  30

Pro Asn Asp Leu Glu Pro Asp Asp Leu Gly Pro Leu Ala Asn Gln Asn
         35                  40                  45

Trp Lys Ala Ile Arg Ala Glu Glu Ser Gln Val His Ala Arg Leu Lys
     50                  55                  60

Gln Ile Arg Val Glu Leu Ile Ala Arg Ile Pro Ser Leu Arg Trp Thr
 65                  70                  75                  80

Arg Ser Gln Arg Glu Ile Ala Ile Leu Ile Trp Pro Arg Ile Leu Pro
                 85                  90                  95

Ile Leu Gln Ala Tyr Asp Leu Arg Gln Ser Met Gln Leu Pro Thr Val
            100                 105                 110

Trp Glu Lys Leu Thr Gln Ser Thr Val Asn Leu Ile Ser Asp Gly Leu
        115                 120                 125

Glu Arg Val Val Leu His Ile Ser Asn Gln Leu Thr Gly Lys Pro Asn
    130                 135                 140

Leu Phe Thr Arg Ser Arg Ala Gly Gln Asp Thr Lys Asp Tyr Ser Ile
145                 150                 155                 160

Pro Ser Thr Arg Glu Leu Ser Gln Ile Trp Phe Asn Asn Glu Trp Ser
                165                 170                 175

Gly Ser Val Lys Thr Trp Leu Met Ile Lys Tyr Arg Met Arg Gln Leu
            180                 185                 190

Ile Thr Asn Gln Lys Thr Gly Glu Leu Thr Asp Leu Val Thr Ile Val
        195                 200                 205

Asp Thr Arg Ser Thr Leu Cys Ile Ile Thr Pro Glu Leu Val Ala Leu
    210                 215                 220

Tyr Ser Ser Glu His Lys Ala Leu Thr Tyr Leu Thr Phe Glu Met Val
225                 230                 235                 240

Leu Met Val Thr Asp Met Leu Glu Gly Arg Leu Asn Val Ser Ser Leu
                245                 250                 255

Cys Thr Ala Ser His Tyr Leu Ser Pro Leu Lys Lys Arg Ile Glu Val
            260                 265                 270

Leu Leu Thr Leu Val Asp Asp Leu Ala Leu Leu Met Gly Asp Lys Val
        275                 280                 285

Tyr Gly Ile Val Ser Ser Leu Glu Ser Phe Val Tyr Ala Gln Leu Gln
    290                 295                 300

Tyr Gly Asp Pro Val Ile Asp Ile Lys Gly Thr Phe Tyr Gly Phe Ile
305                 310                 315                 320

Cys Asn Glu Ile Leu Asp Leu Leu Thr Glu Asp Asn Ile Phe Thr Glu
                325                 330                 335

Glu Glu Ala Asn Lys Val Leu Leu Asp Leu Thr Ser Gln Phe Asp Asn
            340                 345                 350

Leu Ser Pro Asp Leu Thr Ala Glu Leu Leu Cys Ile Met Arg Leu Trp
        355                 360                 365

Gly His Pro Thr Leu Thr Ala Ser Gln Ala Ala Ser Lys Val Arg Glu
    370                 375                 380
```

-continued

```
Ser Met Cys Ala Pro Lys Val Leu Asp Phe Gln Thr Ile Met Lys Thr
385                 390                 395                 400

Leu Ala Phe Phe His Ala Ile Leu Ile Asn Gly Tyr Arg Arg Ser His
                405                 410                 415

Asn Gly Ile Trp Pro Pro Thr Thr Leu His Gly Asn Ala Pro Lys Ser
            420                 425                 430

Leu Ile Glu Met Arg His Asp Asn Ser Glu Leu Lys Tyr Glu Tyr Val
        435                 440                 445

Leu Lys Asn Trp Lys Ser Ile Ser Met Leu Arg Ile His Lys Cys Phe
    450                 455                 460

Asp Ala Ser Pro Asp Glu Asp Leu Ser Ile Phe Met Lys Asp Lys Ala
465                 470                 475                 480

Ile Ser Cys Pro Arg Gln Asp Trp Met Gly Val Phe Arg Arg Ser Leu
                485                 490                 495

Ile Lys Gln Arg Tyr Arg Asp Ala Asn Arg Pro Leu Pro Gln Pro Phe
            500                 505                 510

Asn Arg Arg Leu Leu Leu Asn Phe Leu Glu Asp Asp Arg Phe Asp Pro
        515                 520                 525

Ile Lys Glu Leu Glu Tyr Val Thr Ser Gly Glu Tyr Leu Arg Asp Pro
    530                 535                 540

Glu Phe Cys Ala Ser Tyr Ser Leu Lys Glu Lys Glu Ile Lys Ala Thr
545                 550                 555                 560

Gly Arg Ile Phe Ala Lys Met Thr Lys Arg Met Arg Ser Cys Gln Val
                565                 570                 575

Ile Ala Glu Ser Leu Leu Ala Asn His Ala Gly Lys Leu Met Arg Glu
            580                 585                 590

Asn Gly Val Val Leu Asp Gln Leu Lys Leu Thr Lys Ser Leu Leu Thr
        595                 600                 605

Met Asn Gln Ile Gly Ile Ile Ser Glu His Ser Arg Arg Ser Thr Ala
    610                 615                 620

Asp Asn Met Thr Leu Ala His Ser Gly Ser Asn Lys His Arg Ile Asn
625                 630                 635                 640

Asn Ser Gln Phe Lys Lys Asn Lys Asp Asn Lys His Glu Met Pro Asp
                645                 650                 655

Asp Gly Phe Glu Ile Ala Ala Cys Phe Leu Thr Thr Asp Leu Thr Lys
            660                 665                 670

Tyr Cys Leu Asn Trp Arg Tyr Gln Val Ile Ile Pro Phe Ala Arg Thr
        675                 680                 685

Leu Asn Ser Met Tyr Gly Ile Pro His Leu Phe Glu Trp Ile His Leu
    690                 695                 700

Arg Leu Met Arg Ser Thr Leu Tyr Val Gly Asp Pro Phe Asn Pro Pro
705                 710                 715                 720

Ser Asp Pro Thr Gln Leu Asp Leu Asp Thr Ala Leu Asn Asp Asp Ile
                725                 730                 735

Phe Ile Val Ser Pro Arg Gly Gly Ile Glu Gly Leu Cys Gln Lys Leu
            740                 745                 750

Trp Thr Met Ile Ser Ile Ser Thr Ile Ile Leu Ser Ala Thr Glu Ala
        755                 760                 765

Asn Thr Arg Val Met Ser Met Val Gln Gly Asp Asn Gln Ala Ile Ala
    770                 775                 780

Ile Thr Thr Arg Val Val Arg Ser Leu Ser His Ser Glu Lys Lys Glu
785                 790                 795                 800

Gln Ala Tyr Lys Ala Ser Lys Leu Phe Phe Glu Arg Leu Arg Ala Asn
```

-continued

```
                805                 810                 815

Asn His Gly Ile Gly His His Leu Lys Glu Gln Glu Thr Ile Leu Ser
            820                 825                 830

Ser Asp Phe Phe Ile Tyr Ser Lys Arg Val Phe Tyr Lys Gly Arg Ile
        835                 840                 845

Leu Thr Gln Ala Leu Lys Asn Val Ser Lys Met Cys Leu Thr Ala Asp
    850                 855                 860

Ile Leu Gly Asp Cys Ser Gln Ala Ser Cys Ser Asn Leu Ala Thr Thr
865                 870                 875                 880

Val Met Arg Leu Thr Glu Asn Gly Val Glu Lys Asp Leu Cys Tyr Phe
                885                 890                 895

Leu Asn Ala Phe Met Thr Ile Arg Gln Leu Cys Tyr Asp Leu Val Phe
            900                 905                 910

Pro Gln Thr Lys Ser Leu Ser Gln Asp Ile Thr Asn Ala Tyr Leu Asn
        915                 920                 925

His Pro Ile Leu Ile Ser Arg Leu Cys Leu Leu Pro Ser Gln Leu Gly
    930                 935                 940

Gly Leu Asn Phe Leu Ser Cys Ser Arg Leu Phe Asn Arg Asn Ile Gly
945                 950                 955                 960

Asp Pro Leu Val Ser Ala Ile Ala Asp Val Lys Arg Leu Ile Lys Ala
                965                 970                 975

Gly Cys Leu Asp Ile Trp Val Leu Tyr Asn Ile Leu Gly Arg Arg Pro
            980                 985                 990

Gly Lys Gly Lys Trp Ser Thr Leu Ala Ala Asp Pro Tyr Thr Leu Asn
        995                 1000                1005

Ile Asp Tyr Leu Val Pro Ser Thr Thr Phe Leu Lys Lys His Ala Gln
   1010                1015                1020

Tyr Thr Leu Met Glu Arg Ser Val Asn Pro Met Leu Arg Gly Val Phe
1025                1030                1035                1040

Ser Glu Asn Ala Ala Glu Glu Glu Glu Glu Leu Ala Gln Tyr Leu Leu
               1045                1050                1055

Asp Arg Glu Val Val Met Pro Arg Val Ala His Val Ile Leu Ala Gln
           1060                1065                1070

Ser Ser Cys Gly Arg Arg Lys Gln Ile Gln Gly Tyr Leu Asp Ser Thr
       1075                1080                1085

Arg Thr Ile Ile Arg Tyr Ser Leu Glu Val Arg Pro Leu Ser Ala Lys
   1090                1095                1100

Lys Leu Asn Thr Val Ile Glu Tyr Asn Leu Leu Tyr Leu Ser Tyr Asn
1105                1110                1115                1120

Leu Glu Ile Ile Glu Lys Pro Asn Ile Val Gln Pro Phe Leu Asn Ala
               1125                1130                1135

Ile Asn Val Asp Thr Cys Ser Ile Asp Ile Ala Arg Ser Leu Arg Lys
           1140                1145                1150

Leu Ser Trp Ala Thr Leu Leu Asn Gly Arg Pro Ile Glu Gly Leu Glu
       1155                1160                1165

Thr Pro Asp Pro Ile Glu Leu Val His Gly Cys Leu Ile Ile Gly Ser
   1170                1175                1180

Asp Glu Cys Glu His Cys Ser Ser Gly Asp Asp Lys Phe Thr Trp Phe
1185                1190                1195                1200

Phe Leu Pro Lys Gly Ile Arg Leu Asp Asp Asp Pro Ala Ser Asn Pro
               1205                1210                1215

Pro Ile Arg Val Pro Tyr Ile Gly Ser Lys Thr Asp Glu Arg Arg Val
           1220                1225                1230
```

-continued

```
Ala Ser Met Ala Tyr Ile Lys Gly Ala Ser Val Ser Leu Lys Ser Ala
       1235                1240                1245

Leu Arg Leu Ala Gly Val Tyr Ile Trp Ala Phe Gly Asp Thr Glu Glu
   1250                1255                1260

Ser Trp Gln Asp Ala Tyr Glu Leu Ala Ser Thr Arg Val Asn Leu Thr
1265                1270                1275                1280

Leu Glu Gln Leu Gln Ser Leu Thr Pro Leu Pro Thr Ser Ala Asn Leu
               1285                1290                1295

Val His Arg Leu Asp Asp Gly Thr Thr Gln Leu Lys Phe Thr Pro Ala
           1300                1305                1310

Ser Ser Tyr Ala Phe Ser Ser Phe Val His Ile Ser Asn Asp Cys Gln
       1315                1320                1325

Ile Leu Glu Ile Asp Asp Gln Val Thr Asp Ser Asn Leu Ile Tyr Gln
   1330                1335                1340

Gln Val Met Ile Thr Gly Leu Ala Leu Ile Glu Thr Trp Asn Asn Pro
1345                1350                1355                1360

Pro Ile Asn Phe Ser Val Tyr Glu Thr Thr Leu His Leu His Thr Gly
               1365                1370                1375

Ser Ser Cys Cys Ile Arg Pro Val Glu Ser Cys Val Val Asn Pro Pro
           1380                1385                1390

Leu Leu Pro Val Pro Leu Ile Asn Val Pro Gln Met Asn Lys Phe Val
       1395                1400                1405

Tyr Asp Pro Glu Pro Leu Ser Leu Leu Glu Met Glu Lys Ile Glu Asp
   1410                1415                1420

Ile Ala Tyr Gln Thr Arg Ile Gly Gly Leu Asp Gln Ile Pro Leu Leu
1425                1430                1435                1440

Glu Lys Ile Pro Leu Leu Ala His Leu Thr Ala Lys Gln Met Val Asn
               1445                1450                1455

Ser Ile Thr Gly Leu Asp Glu Ala Thr Ser Ile Met Asn Asp Ala Val
           1460                1465                1470

Val Gln Ala Asp Tyr Thr Ser Asn Trp Ile Ser Glu Cys Cys Tyr Thr
       1475                1480                1485

Tyr Ile Asp Ser Val Phe Val Tyr Ser Gly Trp Ala Leu Leu Leu Glu
   1490                1495                1500

Leu Ser Tyr Gln Met Tyr Tyr Leu Arg Ile Gln Gly Ile Gln Gly Ile
1505                1510                1515                1520

Leu Asp Tyr Val Tyr Met Thr Leu Arg Arg Ile Pro Gly Met Ala Ile
               1525                1530                1535

Thr Gly Ile Ser Ser Thr Ile Ser His Pro Arg Ile Leu Arg Arg Cys
           1540                1545                1550

Ile Asn Leu Asp Val Ile Ala Pro Ile Asn Ser Pro His Ile Ala Ser
       1555                1560                1565

Leu Asp Tyr Thr Lys Leu Ser Ile Asp Ala Val Met Trp Gly Thr Lys
   1570                1575                1580

Gln Val Leu Thr Asn Ile Ser Gln Gly Ile Asp Tyr Glu Ile Val Val
1585                1590                1595                1600

Pro Ser Glu Ser Gln Leu Thr Leu Ser Asp Arg Val Leu Asn Leu Val
               1605                1610                1615

Ala Arg Lys Leu Ser Leu Leu Ala Ile Ile Trp Ala Asn Tyr Asn Tyr
           1620                1625                1630

Pro Pro Lys Val Lys Gly Met Ser Pro Glu Asp Lys Cys Gln Ala Leu
       1635                1640                1645
```

-continued

```
Thr Thr His Leu Leu Gln Thr Val Glu Tyr Val Glu Tyr Ile Gln Ile
   1650                1655                1660

Glu Lys Thr Asn Ile Arg Arg Met Ile Ile Glu Pro Lys Leu Thr Ala
1665                1670                1675                1680

Tyr Pro Ser Asn Leu Phe Tyr Leu Ser Arg Lys Leu Leu Asn Ala Ile
                1685                1690                1695

Arg Asp Ser Glu Glu Gly Gln Phe Leu Ile Ala Ser Tyr Tyr Asn Ser
            1700                1705                1710

Phe Gly Tyr Leu Glu Pro Ile Leu Met Glu Ser Lys Ile Phe Asn Leu
        1715                1720                1725

Ser Ser Ser Glu Ser Ala Ser Leu Thr Glu Phe Asp Phe Ile Leu Asn
   1730                1735                1740

Leu Glu Leu Ser Asp Ala Ser Leu Glu Lys Tyr Ser Leu Pro Ser Leu
1745                1750                1755                1760

Leu Met Thr Ala Glu Asn Met Asp Asn Pro Phe Pro Gln Pro Pro Leu
                1765                1770                1775

His His Val Leu Arg Pro Leu Gly Leu Ser Ser Thr Ser Trp Tyr Lys
            1780                1785                1790

Thr Ile Ser Val Leu Asn Tyr Ile Ser His Met Lys Ile Ser Asp Gly
        1795                1800                1805

Ala His Leu Tyr Leu Ala Glu Gly Ser Gly Ala Ser Met Ser Leu Ile
   1810                1815                1820

Glu Thr Phe Leu Pro Gly Glu Thr Ile Trp Tyr Asn Ser Leu Phe Asn
1825                1830                1835                1840

Ser Gly Glu Asn Pro Pro Gln Arg Asn Phe Ala Pro Leu Pro Thr Gln
                1845                1850                1855

Phe Ile Glu Ser Val Pro Tyr Arg Leu Ile Gln Ala Gly Ile Ala Ala
            1860                1865                1870

Gly Asn Gly Ile Val Gln Ser Phe Tyr Pro Leu Trp Asn Gly Asn Ser
        1875                1880                1885

Asp Ile Thr Asp Leu Ser Thr Lys Thr Ser Val Glu Tyr Ile Ile His
   1890                1895                1900

Lys Val Gly Ala Asp Thr Cys Ala Leu Val His Val Asp Leu Glu Gly
1905                1910                1915                1920

Val Pro Gly Ser Met Asn Ser Met Leu Glu Arg Ala Gln Val His Ala
                1925                1930                1935

Leu Leu Ile Thr Val Thr Val Leu Lys Pro Gly Gly Leu Leu Ile Leu
            1940                1945                1950

Lys Ala Ser Trp Glu Pro Phe Asn Arg Phe Ser Phe Leu Leu Thr Val
        1955                1960                1965

Leu Trp Gln Phe Phe Ser Thr Ile Arg Ile Leu Arg Ser Ser Tyr Ser
   1970                1975                1980

Asp Pro Asn Asn His Glu Val Tyr Ile Ile Ala Thr Leu Ala Val Asp
1985                1990                1995                2000

Pro Thr Thr Ser Ser Phe Thr Thr Ala Leu Asn Arg Ala Arg Thr Leu
                2005                2010                2015

Asn Glu Gln Gly Phe Ser Leu Ile Pro Pro Glu Leu Val Ser Glu Tyr
            2020                2025                2030

Trp Arg Lys Arg Val Glu Gln Gly Gln Ile Ile Gln Asp Cys Ile Asp
        2035                2040                2045

Lys Val Ile Ser Glu Cys Val Arg Asp Gln Tyr Leu Ala Asp Asn Asn
   2050                2055                2060

Ile Ile Leu Gln Ala Gly Gly Thr Pro Ser Thr Arg Lys Trp Leu Asp
```

-continued 2065 2070 2075 2080

Leu Pro Asp Tyr Ser Ser Phe Asn Glu Leu Gln Ser Glu Met Ala Arg
2085 2090 2095

Leu Ile Thr Ile His Leu Lys Glu Val Ile Glu Ile Leu Lys Gly Gln
2100 2105 2110

Ala Ser Asp His Asp Thr Leu Leu Phe Thr Ser Tyr Asn Val Gly Pro
2115 2120 2125

Leu Gly Lys Ile Asn Thr Ile Leu Arg Leu Ile Val Glu Arg Ile Leu
2130 2135 2140

Met Tyr Thr Val Arg Asn Trp Cys Ile Leu Pro Thr Gln Thr Arg Leu
2145 2150 2155 2160

Thr Leu Arg Gln Ser Ile Glu Leu Gly Glu Phe Arg Leu Arg Asp Val
2165 2170 2175

Ile Thr Pro Met Glu Ile Leu Lys Leu Ser Pro Asn Arg Lys Tyr Leu
2180 2185 2190

Lys Ser Ala Leu Asn Gln Ser Thr Phe Asn His Leu Met Gly Glu Thr
2195 2200 2205

Ser Asp Ile Leu Leu Asn Arg Ala Tyr Gln Lys Arg Ile Trp Lys Ala
2210 2215 2220

Ile Gly Cys Val Ile Tyr Cys Phe Gly Leu Leu Thr Pro Asp Val Glu
2225 2230 2235 2240

Gly Ser Glu Arg Ile Asp Val Asp Asn Asp Ile Pro Asp Tyr Asp Ile
2245 2250 2255

His Gly Asp Ile Ile
2260

<210> SEQ ID NO 11
<211> LENGTH: 15384
<212> TYPE: DNA
<213> ORGANISM: Mumps virus

<400> SEQUENCE: 11
accaagggga gaatgaatat gggatattgg tagaacaaat agtgtaagaa acagtaagcc 60
cggaagtggt gttttgcgat ttcgaggccg agctcgatcc tcaccttcca tcgtcgctag 120
ggggcatttt gacactacct ggaaaatgtc atctgtgctc aaggcatttg agcggttcac 180
gatagaacag gaacttcaag acaggggtga ggagggttca attccaccgg agactttaaa 240
gtcagcagtc aaagtcttcg ttattaacac acccaatccc accacacgct atcagatgct 300
aaacttttgc ttaagaataa tctgcagtca aaatgctagg gcatctcaca gggtaggtgc 360
attgataaca ttattctcac ttccctcagc aggcatgcaa aatcatatta gattagcaga 420
tagatcaccc gaagctcaga tagaacgctg tgagattgat ggttttgagc ctggtacata 480
taggctgatt ccaaatgcac gcgccaatct tactgccaat gaaattgctg cctatgcttt 540
gcttgcagat gacctccctc caaccataaa taatggaact ccttacgtac atgcagatgt 600
tgaaggacag ccatgtgatg agattgagca gttcctggat cggtgttaca gtgtactaat 660
ccaggcttgg gtaatggtct gtaaatgtat gacagcgtac gaccaacctg ccgggtctgc 720
tgatcggcga tttgcgaaat accagcagca aggtcgcctt gaggcaagat acatgctgca 780
accggaggcc caaaggttga ttcaaactgc catcaggaaa agtcttgttg ttagacagta 840
ccttaccttc gaactccagt tggcgagacg gcagggattg ctatcaaaca gatactatgc 900
aatggtgggt gacatcggaa agtacattga gaattcaggc cttactgcct tctttctcac 960
tctcaaatat gcactaggga ccaaatggag tcctctatca ttggctgcat tcaccggtga 1020

-continued

```
actcaccaag ctccgatcct tgatgatgtt atatcgaggt ctcggagaac aagccagata   1080
ccttgctctg ttagaggctc cccaaataat ggactttgca cccgggggct acccattgat   1140
attcagttat gctatgggag tcggtacagt cctagatgtt caaatgcgaa attacactta   1200
tgcacgacct ttcctaaacg gttattattt ccagattggg gttgagaccg cacgaagaca   1260
acaaggcact gttgacaaca gagtagcaga tgatctgggc ctgactcctg agcaaagaac   1320
tgaggtcact cagcttgttg acaggcttgc aaggggaaga ggtgctggga taccaggtgg   1380
gcctgtgaat ccttttgttc ctccagttca acagcaacaa cctgctgccg tatatgagga   1440
cattcctgca ttggaggaat cagatgacga tggtgatgaa gatggaggcg caggattcca   1500
aaatggagta caattaccag ctgtaagaca gggaggtcaa actgacttta gagcacagcc   1560
tttgcaagat ccaattcaag cacaactttt catgccatta tatcctcaag tcagcaacat   1620
gccaaataat cagaatcatc agatcaatcg catcgggggg ctggaacacc aagatttatt   1680
acgacacaac gagaatggtg attcccaaca agatgcaagg ggcgaacacg taaacacttt   1740
cccaaacaat cccaatcaaa acgcacagtt gcaagtggga gactgggatg agtaaatcac   1800
tgacatgatc aaactaaccc caatcgcaac aatcccagga caatccagcc acagctaact   1860
gcccaaatcc actacattcc attcatattt agtctttaag aaaaaattag gcccggaaag   1920
aattaggtcc acgatcacag gcacaatcat ttttatcgtg tttctttccg ggcaagccat   1980
ggatcaattt ataaaacagg atgagaccgg tgatttaatt gagacaggaa tgaatgttgc   2040
gaatcatttc ctatccaccc caattcaggg aaccaattcg ctgagcaagg cctcaatcct   2100
ccctggtgtt gcacctgtac tcattggcaa tccagagcaa aagaacattc agcaccctac   2160
cgcatcacat cagggatcca agacaaaggg cagaggctca ggagtcaggt ccatcatagt   2220
ctcaccctcc gaagcaggca atggagggac tcagattcct gagccccttt ttgcacaaac   2280
aggacagggt ggtatagtca ccacagttta ccaggatcca actatccaac caacaggttc   2340
ataccgaagt gtggaattgg cgaagatcgg aaaagagaga atgattaatc gatttgttga   2400
gaaacctaga acctcaacgc cggtgacaga atttaagagg ggggccggga gcggctgctc   2460
aaggccagac aatccaagag gagggcatag acgggaatgg agcctcagct gggtccaagg   2520
agaggtccgg gtctttgagt ggtgcaaccc tatatgctca cctatcactg ccgcagcaag   2580
attccactcc tgcaaatgtg ggaattgccc cgcaaagtgc gatcagtgcg aacgagatta   2640
tggacctcct tagggggatg gatgctcgcc tgcaacatct tgaacaaaag gtggacaagg   2700
tgcttgcaca gggcagcatg gtgacccaaa taaagaatga attatcaaca gtaaagacaa   2760
cattagcaac aattgaaggg atgatggcaa cagtaaagat catggatcct ggaaatccga   2820
caggggtccc agttgatgag cttagaagaa gttttagtga tcacgtgaca attgttagtg   2880
gaccaggaga tgtgtcgttc agctccagtg aaaaacccac actgtatttg gatgagctgg   2940
cgaggcccgt ctccaagcct cgtcctgcaa agcagacaaa atcccaacca gtaaaggatt   3000
tagcaggaca gaaagtgatg attaccaaaa tgatcactga ttgtgtggct aatcctcaaa   3060
tgaagcaggc gttcgagcaa cgattggcaa aggccagcac cgaggatgct ctgaacgata   3120
tcaagagaga catcatacga agcgccatat gaattcacca ggagcaccag actcaaggaa   3180
aaatctatga actgagagcc acaatgattc cctattaaat aaaaaataag cacgaacaca   3240
agtcaaatcc aaccatagca gaaatggcag gatcacagat caaaattcct cttccaaagc   3300
cccccgattc agactctcaa agactaaatg ccttccctgt catcatggct caagaaggca   3360
```

-continued

```
aaggacgact ccttagacaa atcaggctta ggaaaatatt atcaggggat ccgtctgatc   3420
agcaaattac atttgtgaat acatatggat tcatccgtgc cactccagaa acatccgagt   3480
tcatctctga atcatcacaa caaaaggtaa ctcctgtagt gacagcgtgc atgctgtcct   3540
ttggtgccgg accagtgcta gaagatccac aacatatgct caaggctctt gatcagacag   3600
acattagggt tcggaaaaca gcaagtgata aagagcagat cttattcgag atcaaccgca   3660
tccccaatct attcaggcat tatcaaatat ctgcggacca tctgattcag gccagctccg   3720
ataaatatgt caaatcacca gcaaaattga ttgcaggagt aaattacatc tactgtgtta   3780
cattcttatc tgtgacagtt tgttctgcct cactcaagtt tcgagttgcg cgcccattgc   3840
ttgctgcacg gtccagatta gtaagagcag ttcagatgga aattttgctt cgggtaactt   3900
gcaaaaaaga ttctcaaatg gcaaagagca tgttaaatga ccctgatgga gaagggtgca   3960
ttgcatccgt gtggttccac ctatgtaatc tgtgcaaagg cagaaataaa cttagaagtt   4020
acgatgaaaa ttattttgct tctaagtgcc gtaagatgaa tctgacagtc agcataggag   4080
atatgtgggg accaaccatt ctagtccatg caggcggtca cattccgaca actgcaaaac   4140
ctttttttcaa ctcaagaggc tggtctgcc acccaatcca ccaatcatca ccatcgttgg   4200
cgaagaccct atggtcatct gggtgtgaaa tcaaggctgc cagtgctatt ctccagggtt   4260
cagactatgc atcacttgca aagactgatg acataatata ttcgaagata aaagtcgata   4320
aagacgcggc caactacaaa ggagtatcct ggagtccatt caggaagtct gcctcaatga   4380
gaaacctatg agaatttcct ctatttccac tgatgcctat aggagaatca acaatcaagc   4440
aaatttgacc ggtggtaatt cgattgaaat tatagaaaaa ataagcctag aaggatatcc   4500
tacttctcga ctttccaact ttgaaaatag aatagatcag taatcatgaa cgcttttcca   4560
gttatttgct tgggctatgc aatcttttca tcctctatat gtgtgaatat caataccttg   4620
cagcaaattg gatacatcaa gcaacaggtc aggcaactaa gctattactc acaaagttca   4680
agctcctacg tagtagtcaa gcttttaccg aatatccaac ccactgataa cagctgtgaa   4740
tttaagagtg taactcaata caataagacc ttgagtaatt tgctccttcc aattgcagaa   4800
aacataaaca atattgcatc gccctcactt gggtcaagac gtcataaacg gtttgctggc   4860
attgccattg gcattgctgc gctcggtgtt gcgaccgcag cacaagtgac tgccgctgtc   4920
tcattagttc aagcacagac aaatgcacgt gcaatagcag cgatgaaaaa ttcaatacag   4980
gcaactaatc gggcagtctt cgaagtgaag gaaggcaccc aacagttagc tatagcggta   5040
caagcaatac aagaccatat caatactatt atgagcaccc aattgaacaa tatgtcttgt   5100
cagatccttg ataaccaact tgcaacctcc ctaggattat acctaacaga attaacaaca   5160
gtgtttcagc cacaattaat taatccagca ttgtcaccga ttagtataca agccttgagg   5220
tctttgcttg gaagtatgac gcctgcagtg gttcaagcaa cattatctac ttcaatttct   5280
gctgctgaga tactaagtgc cggtctaatg gagggtcaga tagtttctgt tctgctagat   5340
gagatgcaga tgatagttaa gataaacatt ccaactattg tcacacaatc aaatgcattg   5400
gtgattgact tctactcaat ttcgagcttt attaataatc aagaatccat aattcaattg   5460
ccagacagga tcttggagat cgggaacgaa caatggcgct atccagctaa gaattgtaag   5520
ttgacaagac accacatgtt ctgccaatac aatgaggcag agaggctgag cctagaaaca   5580
aaactatgcc ttgcaggcaa tattagtgcc tgtgtgttct cacctatagc agggagttat   5640
atgaggcgat ttgtagcact ggatggaaca attgttgcaa actgccggag tctaacatgt   5700
ctatgtaaga gtccatctta tcctatatac caacctgacc atcatgcagt cacgaccatt   5760
```

-continued

```
gatctaacat catgtcaaac attgtccttg gacggactgg atttcagcat tgtctcgcta   5820
agcaatatca cttacactga gaatcttact atttcattgt ctcagacaat caatacccaa   5880
cccattgata tatcaactga gctgagtaag gttaatgcat cccttcaaaa tgccgttaaa   5940
tacataaaag aaagcaacca tcaactccaa tcctttagtg tgggttctaa aatcggagct   6000
ataattgtat cagccttggt tttgagcatc ctgtcgatta tcatttcgct attgttttgc   6060
tgctgggctt acattgcgac taaagaaatc agaagaatca acttcaaaac aaatcatatc   6120
aacacaatat caagtagtgt cgatgatctc atcaggtact aatcttagat tggtgattcg   6180
tcctgcaatt ttaaaagatt tagaaaaaaa ctaaaataag aatgaatctc ctagggtcgt   6240
aacgtctcgt gaccctgccg tcgcactatg ccggcaatcc aacctccctt atacctaaca   6300
tttctagtgc taatccttct ctatctcatc ataaccctgt atgtctggac tatattgact   6360
attaactata agacggcggt gcgatatgca gcactgtacc agcgatcctt ctctcgctgg   6420
ggttttgatc actcactcta gaaagatccc caattaggac aagtcccgat ccgtcacgct   6480
agaacaagct gcattcaaat gaagctgtgc taccatgaga cataaagaaa aaagcaagcc   6540
agaacaaacc taggatcata acacaataca gaatattagc tgctatcaca actgtgttcc   6600
ggccactaag aaaatggagc cctcgaaact atttataatg tcggacaatg ccacctttgc   6660
acctggacct gttgttaatg cggctggtaa gaagacattc cgaacctgtt tccgaatatt   6720
ggtcctatct gtacaagcag ttatccttat attggttatt gtcactttag gtgagcttat   6780
taggatgatc aatgatcaag gcttgagcaa tcagttgtct tcaattacag acaagataag   6840
agaatcagct gctgtgattg catctgctgt gggagtaatg aatcaagtta ttcatggagt   6900
aacggtatcc ttacctctac aaattgaggg taaccaaaat caattattat ccacacttgc   6960
tacaatctgc acaaacagaa atcaagtctc aaactgctcc acaaacatcc ccttaattaa   7020
tgaccttagg tttataaatg gaatcaataa attcatcatt gaagattatg caacccatga   7080
tttctccatc ggccatccac ttaacatgcc tagctttatc cccactgcaa cctcacccaa   7140
tggttgcacg agaattccat ccttttcttt aggtaagaca cactggtgtt acacacataa   7200
tgtaattaat gccaactgca aggatcatac ttcatccaac caatatgttt ccatggggat   7260
tcttgctcaa accgcgtcag ggtatcccat gttcaaaacc ctaaaaaatcc aatatctcag   7320
tgatggcctg aatcggaaaa gctgctcaat tgcaacagtc cctgatggtt gcgcgatgta   7380
ctgttacgtt tcaactcaac ttgaaaccga cgactatgcg gggtccagcc cacctaccca   7440
gaaacttatc ctgttattct ataatgacac catcacagaa aggacaatat ctccatctgg   7500
tcttgaaggg aattgggcta ctttggtgcc aggagtgggg agtggaatat atttcgaaaa   7560
taagttgatc tttcctgcat acgggggtgt attgcccaat agtacactag gagttaaatt   7620
agcaagagaa tttttccggc ccgttaatcc atataatcca tgttcaggac cacaacaaga   7680
gttagatcag cgtgctttga gatcatattt cccaagttac ttctctagtc gacgggtaca   7740
gagtgcattt ctggtctgtg cttggaatca gatcctagtt acaaattgcg agctagttgt   7800
cccctcaaac aatcagacac tgatgggtgc agaaggaaga gttttattga tcaacaatcg   7860
actattatat tatcagagga gtactagctg gtggccgtat gaactcctct atgagatatc   7920
attcacattt acaaactacg gtcaatcatc tgtgaatatg tcctggatac ctatatattc   7980
attcactcgt cctggttcgg gccactgcag tggtgaaaat gtatgcccaa tagtctgtgt   8040
atcaggagtt tatcttgatc cctggccatt aactccatac agacaccaat caggcattaa   8100
```

-continued

```
cagaaatttc tatttcacag gtgcactgct aaattcaagc acaaccaggg tgaatcctac   8160
actttatgtc tctgccctta ataatcttaa agtactagcc ccatatggta ctcaaggatt   8220
gtttgcttca tacaccacaa ccacctgctt tcaagatacc ggcgacgcca gtgtgtattg   8280
tgtctatatt atggaactgg catcgaatat tgttggggaa ttccaaattc tacctgtgct   8340
agccagattg accatcactt gagttgtagt gaatgtagca ggaagcttta cgggcgtgtc   8400
tcatttctta ttgattatta agaaaaaaca ggccagaatg gcgggcctaa atgagatact   8460
cctacccgaa gtacatttaa actcccccat cgttagatat aagcttttct actatatatt   8520
gcatggccag ttaccaaatg acttggagcc ggatgacttg ggcccattag caaatcagaa   8580
ttggaaggca attcgagctg aagaatcaca ggttcatgca cgtttaaaac agatcagagt   8640
agaactcatt gcaaggattc ctagtctccg gtggacccga tctcaaagag agattgccat   8700
actcatttgg ccaagaatac ttccaatact gcaagcatat gatcttcggc aaagtatgca   8760
attgcccaca gtgtgggaga aactgactca atccacggtt aatcttataa gtgacggtct   8820
agaacgggtt gtattacaca tcagcaatca actaacaggc aagcctaact tgtttaccag   8880
atctcgagcc ggacaagaca caaaagatta ctcaattcca tccactagag agctatctca   8940
aatatggttc aacaatgagt ggagtgggtc tgtaaagacc tggcttatga ttaaatatag   9000
aatgaggcag ctaatcacaa atcaaaagac aggtgagtta acagatctag taaccattgt   9060
ggatactagg tccactctat gcattattac tccagaatta gtcgctttat actccagtga   9120
gcacaaagca ttaacgtacc tcacctttga aatggtatta atggtcactg atatgttaga   9180
gggacggctg aatgtttctt ctctgtgcac agctagtcat tatctgtccc ctttaaaaaa   9240
gagaatcgaa gttctcctga cattagttga tgaccttgca ctactcatgg gggataaagt   9300
atacggtatt gtctcttcac ttgagagttt tgtttacgcc caattacagt atggtgatcc   9360
tgttatagac attaaaggta cattctatgg atttatatgt aatgagattc tcgacctact   9420
gactgaagac aacatcttta ctgaagaaga ggctaataag gttcttctgg acttaacatc   9480
acaatttgac aatctatccc ctgatttaac tgctgagctc ctctgcatta tgagactttg   9540
gggccatccc accttaactg ccagccaagc agcatccaag gtccgagagt ccatgtgcgc   9600
tcctaaggta ttagacttcc aaacaataat gaagaccctg gctttctttc acgcaatcct   9660
aattaacggt tataggagga gccataatgg aatctggccg cctaccactc ttcatggcaa   9720
tgcccccaaa agcctcattg agatgcggca tgataattca gagcttaagt atgagtatgt   9780
cctcaagaat tggaaaagta tatctatgtt aagaatacac aaatgctttg atgcatcacc   9840
tgatgaagat ctcagcatat tcatgaagga taaggcaata agctgtccaa ggcaagactg   9900
gatgggagta tttaggagga gcctgattaa acagcgctat cgtgacgcga atcggcctct   9960
accacaacca tttaaccgga gactgctgtt gaattttcta gaggatgacc gattcgatcc  10020
tattaaagag cttgagtatg tcaccagtgg agaatatctt agggaccctg aattttgtgc  10080
atcttactct ctcaaggaga aggagataaa ggctacaggt cgtatatttg caaaaatgac  10140
aaagagaatg agatcgtgcc aagtaattgc agaatcattg ttagccaatc acgcaggtaa  10200
attaatgaga gagaatgggg ttgtcttaga ccagttaaaa ttaacaaaat ctttattaac  10260
tatgaaccaa attggtatta tatcagagca cagccgaaga tccaccgctg acaacatgac  10320
tttagcacac tccggttcaa ataagcacag gattaataat agtcaattca agaagaataa  10380
agacaataaa catgagatgc ctgatgatgg gtttgagata gcagcctgct tcctaacaac  10440
tgacctcaca aaatactgct tgaattggag gtaccaggtc atcatcccct ttgcgcgtac  10500
```

-continued

```
attgaattca atgtatggta taccccactt gtttgaatgg atacatttaa ggctgatgcg  10560
aagcactctt tatgtcggtg atcccttcaa tcctccatca gatcctaccc aacttgacct  10620
tgatacagcc ctcaatgatg atatatttat agtttcccct cgtggcggaa tcgagggttt  10680
atgtcaaaaa ttatggacta tgatttccat ctcaacaatc atattgtccg caactgaggc  10740
aaacactaga gtaatgagca tggttcaggg cgataaccaa gcaattgcaa tcaccactag  10800
agtagtacgt tcgctcagtc attccgagaa gaaggagcaa gcctataaag caagtaaatt  10860
attctttgaa aggcttagag ctaacaacca tggaattgga caccacttaa aagaacaaga  10920
aacaatcctt agttctgatt tcttcattta cagtaagagg gtgttttaca aaggtcgaat  10980
cttgactcaa gcgttaaaga acgtgagcaa gatgtgctta acagctgata tactggggga  11040
ttgttcacaa gcatcatgct ccaatttagc taccactgta atgcgcctga ctgagaatgg  11100
ggtcgagaaa gatttgtgtt atttcctaaa tgcattcatg acaattagac aattatgtta  11160
tgatctagta tttccccaaa ctaaatctct tagtcaggac attactaatg cttatcttaa  11220
tcatccaata cttatctcaa gattgtgtct attaccatct caattggggg gcttaaactt  11280
tctttcatgt agtcgcctgt ttaatagaaa cataggagat ccactagtgt ctgcaattgc  11340
tgatgtgaaa cgattaatta aagcgggctg tctagatatc tgggtcctgt acaacatcct  11400
tggaaggagg ccaggaaaag gtaagtggag cactctggca gctgatccct atactttaaa  11460
catagattat ttagtccctt caacaacttt tttgaagaaa catgcccaat atacattgat  11520
ggaacggagt gttaatccca tgctccgcgg agtatttagt gaaaatgcag cagaggagga  11580
agaagaactc gcacagtatc tattagatcg cgaagtagtc atgcccaggg ttgcacatgt  11640
tatacttgct cagtctagtt gcggtagaag aaaacagatc caaggttact tggattctac  11700
tagaactatt attaggtatt cactggaggt aaggccactg tcagcaaaga agctgaatac  11760
agtaatagaa tataacttat tgtacctgtc ctacaatttg gagattattg aaaaacccaa  11820
tatagtccaa cctttttga atgcaatcaa tgttgatact tgtagcatcg atatagctag  11880
gtcccttaga aaattatcct gggcaacttt acttaatgga cgtcccatcg agggattaga  11940
aacacctgat cctattgaat tggtacatgg gtgtttaata atcgggtcag atgagtgtga  12000
gcattgcagt agtggtgatg acaaattcac ctggttttc ctccctaagg ggataaggtt  12060
agatgatgat ccggcatcta acccacccat cagagtacct tatatcggat ccaaaacaga  12120
tgaacgaagg gttgcatcaa tggcttatat caaaggggca tcagtatcac ttaaatcagc  12180
actcagatta gcgggggtat atatatgggc tttcggagat acagaggaat catggcagga  12240
tgcctatgag ttagcttcca ctcgtgttaa tctcacacta gagcaattgc aatctctcac  12300
tcctttacca acatctgcca acttagtcca cagattggat gatggcacta ctcaattaaa  12360
atttacccca gcaagctcct atgcattctc tagctttgtt catatatcta acgactgtca  12420
aattcttgag atcgatgatc aggtaacgga ttctaacctg atttaccagc aagtcatgat  12480
tactggcctt gctctaattg agacatggaa taatcctcca atcaacttct ccgtttatga  12540
aaccacatta cacttgcaca caggctcatc ttgctgtata agacctgtcg agtcttgtgt  12600
agtaaatccg cctttacttc ctgtccctct cattaatgtt cctcaaatga ataaatttgt  12660
atatgatcct gaaccactta gtttgttaga aatggaaaaa attgaggata ttgcttatca  12720
aaccagaatt ggtggtttag atcaaatccc gcttctggaa aaaataccct tactagctca  12780
ccttaccgcc aagcagatgg taaatagcat cactgggctt gatgaagcaa catctataat  12840
```

-continued

```
gaatgatgct gtagttcaag cagactatac tagcaattgg attagtgaat gctgctatac  12900
ttacattgac tctgtgtttg tttactccgg ctgggcatta ttattggaac tttcatacca  12960
aatgtattac ctaagaattc aaggcataca aggaatccta gactatgtgt atatgacctt  13020
gaggaggata ccaggaatgg ccataacagg catctcatcc acaattagtc accctcgtat  13080
actcagaaga tgcatcaatt tggatgtcat agccccaatc aattctccac acatagcttc  13140
actggattac acaaaattga gcatagatgc agtaatgtgg ggaaccaagc aggtgttgac  13200
caacatttcg caaggtatcg attatgagat agttgttcct tctgaaagcc aacttacact  13260
cagtgataga gtcctaaatc tagttgctcg aaaattatca ctactggcaa tcatctgggc  13320
caattacaac tatcctccga aggttaaagg tatgtcacct gaagacaaat gtcaggcttt  13380
aactacacat ctactccaaa ctgttgaata tgtcgagtac attcagattg aaaagacaaa  13440
catcaggagg atgattattg agccaaaatt aactgcctac cctagtaatt tgttttacct  13500
ctctcgaaag ctgcttaatg ctattcgaga ctcagaagaa ggacaattcc tgattgcatc  13560
ctattataac agttttggat atctggaacc gatattaatg gaatctaaaa tattcaatct  13620
gagttcatcc gaatcagcat ctcttacaga atttgatttc atcctcaact tggaattgtc  13680
cgacgccagc cttgagaaat actctctccc aagtttgctt atgacggctg agaatatgga  13740
taacccattt cctcaacccc cacttcatca cgttctcaga ccactaggtt tgtcatccac  13800
ctcatggtat aaaacaatca gtgttttaaa ttatattagc catatgaaga tatctgacgg  13860
tgcccatcta tacttggcag agggaagtgg agcctctatg tcacttatag aaactttctt  13920
gcccggggaa acaatatggt acaacagcct gttcaatagt ggtgagaatc cccctcaacg  13980
taatttcgcc cctttgccca cccagtttat tgaaagtgtc ccctatagat tgattcaggc  14040
aggtatagca gcaggaaatg gcatagtgca aagtttctat ccgctctgga acggaaacag  14100
cgatataact gacttaagca cgaaaactag tgttgaatac attatccaca aggtaggagc  14160
tgatacttgt gcattagttc atgtggattt ggaaggtgta cctggctcaa tgaacagcat  14220
gttggagaga gctcaagtac atgcgctgct aattacagtg actgtattaa aaccaggcgg  14280
cttactaatc ttgaaagctt catgggaacc ttttaatcga ttttcctttt tactcacagt  14340
actctggcaa ttcttttcca caattaggat cttgcgatct tcatactccg atccgaataa  14400
tcacgaggtt tacataatag ccacattggc agttgatccc accacatcct cctttacaac  14460
tgctctgaat agggcacgca ccctgaatga acagggcttt tcactcatcc cacctgaatt  14520
agtgagtgag tactggagga agcgtgttga acaaggacag attatacagg actgtataga  14580
taaagttata tcagagtgtg tcagagatca atatctggca gacaacaaca ttatcctcca  14640
agcgggaggt actccgagca caagaaaatg gttggatctt cctgactatt cttcgttcaa  14700
tgaattacaa tctgaaatgg ccagactcat aacaattcat cttaaagagg taatagaaat  14760
cctaaagggc caagcatcag atcatgacac cctattattt acttcataca acgtaggtcc  14820
cctcggaaaa ataaatacaa tactcagatt gattgttgag agaattctta tgtatactgt  14880
gaggaactgg tgtatcttgc ctacccaaac tcgtctcacc ttacgacaat ctatcgagct  14940
tggagagttt agactaagag atgtgataac acccatggag attctaaaac tatcccccaa  15000
caggaaatat ctgaagtctg cattaaatca atcaacattc aatcatctaa tgggagaaac  15060
atctgacata ttgttaaacc gagcttatca gaagagaatt tggaaagcta ttgggtgtgt  15120
aatctattgc tttggtttgc tcaccccaga tgttgaaggt tctgagcgca ttgatgttga  15180
taatgacata cctgattatg atattcacgg ggacataatt taaatcgact aaagactcct  15240
```

-continued

```
ctggcattac acatcaccaa aaagtgccga actaacatcc aaattcttct aaaccgcaca  15300

cgacctcgaa caatcataac cacatcagta ttaaatctag gagatccttt taagaaaaaa  15360

ttgattttac tttctcccct tggt                                        15384


<210> SEQ ID NO 12
<211> LENGTH: 15384
<212> TYPE: DNA
<213> ORGANISM: Mumps virus

<400> SEQUENCE: 12

accaagggga aaaagaagat gggatatcgg tagaacaaat agtgtaagaa acagtaagcc     60

cggaagtggt gttttgcgat ttcgaggccg ggctcgatcc tcaccttcca ttgtcactag    120

ggggcatttt gacactacct ggaaaatgtt gtctgtgctc aaagcattcg agcggttcac    180

gatagaacag gaacttcaag acaggggtga ggagggttca attccgccgg agactttaaa    240

gtcagcagtc aaagtcttcg ttattaacac acccaatccc accacacgct atcagatgct    300

aaacttttgc ctaagaataa tctgcagtca aaatgctagg gcatctcaca gggtaggtgc    360

attgataaca ttattctcac ttccctcagc aggcatgcaa aatcatatta gattagcaga    420

tagatcacct gaagctcaga tagaacgctg cgagattgat ggttttgaac ctggtacata    480

taggctgatt ccaaatgcac gcgccaatct tactgccaat gaaattgctg cctatgcttt    540

gcttgcagat gacctccctc caaccataaa taatggaact ccttacgtac atgcagatgt    600

tgaaggacag ccatgcgatg agattgagca attcctggat cggtgttaca gtgtactaat    660

ccaggcttgg gtaatggtct gtaaatgtat gacagcgtac gaccaacctg ctggatctgc    720

tgatcggcga tttgcgaaat accagcagca aggtcgcctt gaagcaagat acatgctgca    780

gccggaggcc caaaggttga ttcaaactgc catcaggaaa agtcttgttg ttagacagta    840

ccttaccttc gaactccagt tggcgagacg gcaggggttg ctatcaaaca gatactatgc    900

aatggtgggt gacatcggga agtacattga gaattcagga cttactgcct tctttctcac    960

tctcaaatat gcactaggga ccaaatggag tcctctatca ttggctgcat tcaccggtga   1020

actcactaaa ctccgatcct tgatgatgtt atatcgagat ctcggagaac aagccagata   1080

ccttgctctg ttagaggctc cccaaataat ggactttgca cccgggggct acccattaat   1140

attcagttat gctatgggag tcggtacagt cctggatgtc caaatgcgaa attacactta   1200

tgcacgacct ttcctaaacg gttattattt ccagattggg gttgagaccg cacgaaggca   1260

acaaggcact gttgacaaca gagtagcaga tgatctgggc ctgactcctg agcaaagaac   1320

tgaggttact cagcttgttg acaggcttgc aaggggaaga ggtgctggga taccaggtgg   1380

gcctgtgaat ccttttgttc ctccagttca acagcaacaa cctgctgccg tatatgagga   1440

cattcctgca ttagaggaat cagatgacga tggtgatgaa gatagaggcg caggattcca   1500

aaatggagta caagtaccag ctgtaagaca gggaggtcaa actgacttta gagcacagcc   1560

tttacaagat ccaattcaag cacagctttt catgccatta tatcctcaag tcagcaacat   1620

cccaaataat cagaatcatc agatcaatcg catcgggggg ctggaaaacc aagatttatt   1680

acgatacaac gagaatggtg attctcaaca agatgcaagg ggcgaacacg gaaacacttt   1740

cccaaacaat cccaatcaaa acgcacagct gcaagtgggt gactgggatg agtaaatcac   1800

tgatatgatc aaactaaccc caattgcaat aatcctagga caatctagcc atagcgaact   1860

gcccaaattc actacattct attcatattt agtctttaag aaaaaattag gcccggaaag   1920
```

-continued

```
aattaggtcc acgatcacag gcacaatcat tctgatcgtg tttctttccg ggtaagccat   1980
ggatcaattt ataaaacagg atgagactgg tgatttaatt gagacaggaa tgaatgttgc   2040
aaaccatttc ctatccgccc ccattcaggg aaccaactcg ctgagcaagg cttcaatcat   2100
ccctggcgtt gcacctgtac tcattggcaa tccagagcaa aagaacattc agcaccctac   2160
cgcatcacat cagggatcca agtcaaaggg cagaggctca ggggtcaggt ccatcacagt   2220
cccgcccccc gaagcaggca atggagggac tcagattcct gagccccttt ttgcacaaac   2280
aggacagggt ggcatagtca ccacagtcca ccaggatcca accatccaac caacaggttc   2340
ataccgaagt gtggaattgg cgaagatcgg aaaagagaga atgattaatc gatttgttga   2400
gaaacctaga acctcaacgc cggtgacaga atttaagagg ggggccggga gcggctgctc   2460
aaggccagac aatccaagag gagggcatag acgggaatgg agcctcagct gggtccaagg   2520
agaggtccgg gtctttgagt ggtgcaaccc tatatgctca cctatcactg ccgcagcaag   2580
attccactcc tgcaaatgtg ggaattgccc cgcaaagtgc gaccagtgcg aacgagatta   2640
tggacctcct tagggggatg gatgctcgcc tgcaacatct tgagcaaaag gtggacaagg   2700
tgcttgcaca gggcagcatg gtgacccaaa taaagaatga attatcaaca gtaaagacaa   2760
cattagcaac aattgaaggg atgatggcaa cagtaaaaat catggatcct ggaaatccga   2820
caggggtccc agttgatgag cttagaagaa gttttagtga tcatgtgaca attgttagtg   2880
gaccaggaga tgtgtcgttc agctccagtg aagaacccac actgtatttg gatgagctgg   2940
cgaggcccgt ctccaagcct cgtcctgcaa agcagacaaa accccaacca gtaaaggatt   3000
tggcaggacg aaaagtgatg atcaccaaaa tgattactga ttgtgtggct aaccctcaaa   3060
tgaagcaggc gttcgaacaa cgattggcaa aggccagcac cgaggatgct ctgaacgaca   3120
tcaagagaga tatcatacgg aacgccatat gaattcacca gaagcaccag actcaaggaa   3180
aaatccatga actgagagcc acaatgattc cctattaaat aaaaaataag cacgaacaca   3240
agtcgaatcc aaccatagca gagatggcag gatcacagat caaaattcct cttccaaagc   3300
cccccgattc agactctcaa agactaaatg cattccctgt tatcatggct caagaaggca   3360
aaggacgact tcttagacaa atcaggctta ggaaaatatt atcaggagat ccgtctgatc   3420
agcaaattac atttgtgaat acatatggat tcatccatgc cactccagaa acatccgagt   3480
tcatctctga atcatcacaa caaaaggcaa ctcctgcagt gacagcgtgc atgctgtcct   3540
ttggtgccgg accggtgcta gaagatccac aacatatgct gaaggctctt gatcagacag   3600
acattagggt tcggaaaaca gcaagtgata aagagcagat cctattcgag atcaaccgca   3660
tccccaatct attcaggcat catcaaatat ctgcggacta tctgattcag gccagctccg   3720
ataaatatgt caagtcacca gcgaaattga ttgcaggagt aaattacatc tactgtgtca   3780
cattcttatc tgtgacagtt tgttctgcct cactcaagtt tcgagttgca cgcccattgc   3840
ttgctgcacg gtctagacta gtaagagcag ttcagatgga agttttgctt cgggtaactt   3900
gcaaaaaaga ttctcaaatg gcaaagagca tgttaaatga ccctgatgga gaagggtgca   3960
ttgcatcagt gtggttccac ctatgtaatc tgtgcaaagg caggaataaa cttaggagtt   4020
acgatgaaaa ttattttgct tctaagtgcc gtaagatgaa tctgacagtc agcataggag   4080
atatgtgggg accaaccatt ctagtccatg caggcggtca cattccgaca actgcaaaac   4140
ctttttttcaa ctcaagaggc tgggtctgcc acccaatcca ccaatcatca ccatcgttgg   4200
cgaagaccct atggtcatct gggtgtgaaa tcaaggctgc cagtgctatc ctccagggtt   4260
cagactatgc atcacttgca aagactgatg acataatata ttcgaagata aaagtcgata   4320
```

-continued

```
aagacgcggc caactacaaa ggagtatcct ggagtccatt caggaagtct gcctcaatga   4380
gtaacctatg agaatttcct ctatttccac tgatgcctat aagagaatca acaatcaagc   4440
aaatttgacc ggtggtaatt cgattgaaat tatagaaaaa ataagcctag aaggatatcc   4500
tacttctcaa ccttccaact ttgaaaatag aatagatcag taatcatgaa ggcttatcca   4560
gttatttgct tgggctttgc aatcttttca tcctctatat gtgtgaatat caatatcttg   4620
cagcaaattg gatacatcaa gcaacaggtc aggcaactaa gctattactc acaaagttca   4680
agctcctacg tagtggtcaa gcttttaccg aatatccaac ccactgataa cagctgtgaa   4740
tttaagagtg taactcaata caataagacc ttgagtaatt tgcttcttcc aattgcagaa   4800
aacataaaca atattgcatc gccctcacct gggtcaagac gtcataaacg gtttgctggc   4860
attgccattg gcattgctgc gctcggtgtt gcgaccgcgg cacaagtgac tgccgctgtc   4920
tcattagttc aagcacagac aaatgcacgt gcaatagcag cgatgaaaaa ttcaatacag   4980
gcaactaatc gggcagtctt cgaagtgaag gaaggcaccc agcagttagc tatagcggta   5040
caagcaatac aagaccatat caatactatt atgaacaccc aattgaacaa tatgtcttgt   5100
cagatccttg ataaccagct tgcaacctct ctaggattat acctaacaga attaacaaca   5160
gtgttccagc cacaattaat taatccagca ttgtcaccga ttagtatcca agccttgagg   5220
tctttgcttg gaagtatgac acctgcagtg gttcaagcaa cattatctac ttcaatttct   5280
gctgctgaaa tactaagtgc cggtctaatg gagggtcaga tagtttctgt tctgctagat   5340
gagatgcaga tgatagttaa gataaacatt ccaaccattg tcacacaatc aaatgcattg   5400
gtgattgact tctactcaat ttcaagtttc attaataatc aagaatccat aattcaattg   5460
ccagacagga tcttggagat cgggaatgaa caatggcgct atccagctaa gaattgtaag   5520
tcgacaagac atcacatatt ctgccaatac aatgaggcag agaggctgag cctagaaaca   5580
aaactatgcc ttgcaggcaa tattagtgcc tgtgtgttct cacctatagc agggagctat   5640
atgaggcgat ttgtagcgct ggatggaaca attgttgcaa actgtcgaag tctaacgtgt   5700
ctatgcaaga gtccatctta tcctatatac caacctgacc atcatgcagt cacgaccatt   5760
gatctaacgt catgtcaaac attgtccctg gacggactgg atttcagcat tgtctcacta   5820
agcaacatca cttacgctga gaatcttact atttcattgt ctcagacgat caatactcaa   5880
cccattgata tatcaactga gctgagtaag gttaatgcat ccctccaaaa tgccgttaaa   5940
tacataaaag agagtaacca tcaactccaa tccgttagtg taagttctaa aatcggagct   6000
ataattgtag cagccttagt tttgagcatc ctgtcgatta tcatttcgct attgttttgc   6060
tgctgggctt acattgcgac taaagaaatc agaagaatca acttcaaaac aaatcatatc   6120
aacacaatat caagtagtgt cgatgatctc atcaggtact aattttaaat tggtgattca   6180
tcctgcaatt aaaaaaggtt tagaaaaaaa ctaaaataag aatgaatctc ctagggtcgt   6240
aacgtctcgt gaccctgccg ttgcactatg ccggcaatcc aacctccctt atacctaaca   6300
tttctattgc taacccttct ctatctaatc ataactctgt atgtctggac tatattgacc   6360
attaaccata atacggcggt tcggtatgca gcactgtacc agcgatcctt ctctcgctgg   6420
ggttttgatc aatcactcta gaaagatcct cagttagggc aagtcccgat ccgtcacgct   6480
agaacaagct gcatccaaat gaagctgcac taccatgaga cataaagaaa aaagcaagcc   6540
agaacaaact taggatcaca acacaacaca aaatattagc tgctatcaca actgtgttcc   6600
ggccactaag aaaatggagc cctcgaaact attcataatg tcggacaacg ccacctttgc   6660
```

-continued

```
acctggacct gttgttaatg cggctggtaa gaagacattc cgaacctgtt tccgaatatt   6720
ggtcctatct gtacaagcag ttacccttat attggttatt gtcactttag gtgagcttat   6780
taggatgatc aatgatcaag gcttgagcaa tcagttgtct tcaattacag acaagataag   6840
agaatcagct gctatgattg catctgctgt gggagtaatg aatcaagtaa ttcatggagt   6900
aacggtatcc ttacccctac aaattgaggg aaaccaaaat caattattat ccacacttgc   6960
cacaatctgc acaaacagaa accaagtttc aaactgctct acaaacatcc ccttagttaa   7020
tgaccttagg tttataaatg gaatcaataa gttcatcatt gaagattatg caacccatga   7080
tttctccatc ggccatccac tcaacatgcc tagctttatc ccaactgcaa cctcacccaa   7140
tggttgcaca agaattccat ccttttcttt aggtaagaca cattggtgtt acacacataa   7200
tgtaattaat gccaactgca aggatcatac ttcatcgaac caatatgttt ccatggggat   7260
tctcgttcaa accgcgtcag ggtatcccat gttcaaaacc ctaaaaatcc aatatctcag   7320
tgatggcctg aatcggaaaa gctgctcaat tgcaacagtc cctgatggtt gcgcaatgta   7380
ctgttacgtt tcaactcaac ttgaaaccga cgactatgcg gggtccagcc cacctaccca   7440
gaaacttacc ctgttgttct ataatgacac catcaaagaa aggacaatat ctccgtctgg   7500
tcttgaagga aattgggcta ctttggtgcc aggagtgggg agtggaatat atttcgaaaa   7560
taagttgatc tttcctgcat atgggggtgt cttgcccaat agtacactag gagttaaatc   7620
agcaagagaa tttttccggc ccgttaatcc atataatcca tgttcaggac caccacaaga   7680
gttagatcag cgtgctttga gatcatattt cccaagttac ttctctagtc gaagggtaca   7740
gagtgcattt ctggtctgtg cctggaatca gatcctagtt acaaattgcg agctagttgt   7800
cccctcaaac aatcagacac ttatgggtgc agaaggaaga gttttattga tcaataatcg   7860
gctattatat tatcagagga gtactagctg gtggccgtat gaactcctct atgagatatc   7920
attcacattt acaaactctg gtcaatcatc tgtgaatatg tcctggatac ctatatattc   7980
attcacccgt cctggtttgg gcaaatgcag tggtgaaaat atatgcccaa cagtctgtgt   8040
atcaggagtt tatcttgatc cctggccatt aactccatac agccatcaat caggcattaa   8100
cagaaatttc tatttcacag gtgcactgct aaattcaagc acaaccaggg tgaatcctac   8160
cctttatgtc tctgccctta ataatcttaa agtactagcc ccatatggta ctcaaggatt   8220
gtttgcgtca tacaccacaa ccacctgctt tcaagatacc ggtgacgcta gtgtgtattg   8280
tgtctatatt atggaactag catcgaatat tgttggagaa ttccaaattc tacctgtgct   8340
agccagattg accatcactt gagttgtagt gaatgtagta ggaagcttta tgggcgtgtc   8400
tcatttctta tcgattatta agaaaaaaca ggccagaatg gcgggcctaa atgagatact   8460
cctacccgaa gtacatttaa actcccccat cgttagatat aagcttttct actatatatt   8520
gcatggccag ttaccaaatg atttggagcc agatgacttg ggcccattag caaatcataa   8580
ttggaaggca attcgagctg aggaatccca ggttcatgca cgattaaaac agatcagagt   8640
agaactcatt gcaaggattc ctagtctccg gtggacccgc tctcaaagag agattgccat   8700
actcatttgg ccaagaatac ttccaatact gcaagcatat gatcttcggc aaagtatgca   8760
attgcccaca gtgtgggaga aattgactca atccacggtt aatcttataa gtgatggtct   8820
agaacgggtt gtattacaca tcagcaatca attaacaggc aagcctaact tgtttaccag   8880
atctcgagct ggacaagaca caaaagatta ctcaattcca tccactagag agctatctca   8940
aatatggttt aacaatgagt ggagtgggtc tgtgaagacc tggcttatga ttaaatatag   9000
aatgaggcag ctaatcacaa atcaaaagac aggtgagtta acagatttag taaccattgt   9060
```

-continued

```
ggatactagg tctactctat gcattattac cccagaatta gtcgctttat actccaatga   9120
gcacaaagca ttaacgtacc tcacctttga aatggtatta atggtcactg atatgttaga   9180
gggaagactg aatgtttctt ctctgtgcac agctagtcat tatctgtccc ctttaaagaa   9240
gcgaatcgaa gttctcctga cattagttga tgaccttgct ctactcatgg gggataaagt   9300
atacggtatt gtctcttcac ttgagagttt tgtttacgcc caattacagt atggtgatcc   9360
tgttatagac attaaaggta cattctatgg atttatatgt aatgagattc tcgacctact   9420
gactgaaggc aacatcttta ctgaagaaga ggcaaacaag gttcttctgg acttgacgtc   9480
acagtttgac aatctatccc ctgatttaac agctgagctc ctctgcatta tgagactttg   9540
gggccatccc accttaactg ccagccaagc agcatccaag gtccgagagt ccatgtgcgc   9600
tcctaaggtg ttagatttcc aaacaataat gaaaaccctg gctttctttc acgcaatcct   9660
aattaacggt tataggagga gccataatgg aatctggccg cctactactc ttcatggcaa   9720
tgcccccaaa agcctcattg agatgcggca tgataattca gagcttaagt atgagtatgt   9780
cctcaagaat tggaaaagta tatctatgtt aagaatacac aaatgctttg atgcatcacc   9840
tgatgaagat ctcagcatat tcatgaagga taaggcaata agctgtccaa agcaagactg   9900
gatgggagta tttaggagga gcctgattaa acagcgctat cgtgacgtga atcggcctct   9960
accacaacca tttaaccgga gactgctgtt gaatttccta gaggatgacc gattcgatcc  10020
tagtaaagag cttgagtatg tcaccagtgg agaatatctt agggaccctg aattttgtgc  10080
atcttactct ctcaaagaga aagagataaa ggctacaggt cgtatatttg caaaaatgac  10140
aaagagaatg agatcgtgcc aagtaattgc agaatcattg ttagccaatc acgcaggtaa  10200
attaatgaga gagaatggag ttgtcttaga ccagttgaaa ttaacaaaat ctttattaac  10260
tatgaaccaa attggcatta tatcagagca cagccgaaga tccactgccg acaacatgac  10320
cttggcacac tccggttcaa ataagcacag gattaacaat agtcaattca agaagaataa  10380
agacaacaaa catgagatgc ctgatgatgg gtttgagata gcagcctgct tcctaacaac  10440
tgacctcaca aaatactgct taaattggag gtaccaagtc atcatcccct ttgcgcgtac  10500
attgaattca atgtacggta taccccacct gtttgaatgg atacatttaa ggctgatgcg  10560
aagcactctc tatgtcggtg atcccttcaa tcctccatca gatcctaccc aacttgacct  10620
tgataccgca ctcaacgatg atatatttat agtttcccct cgtggcggaa tcgagggttt  10680
atgtcaaaaa ttatggacta tgatttccat ctcaacaatc atattatccg caactgaggc  10740
aaacactaga gtaatgagca tggttcaggg cgataaccaa gcaattgcaa tcaccactag  10800
agtagtgcgc tcgctcagtc attccgagaa gaaagagcaa gcttataaag caagtaaatt  10860
attctttgaa agacttagag ctaacaacca tggaattgga caccacttaa aagaacaaga  10920
aacaatcctt agttctgatt tcttcatata cagtaagagg gtgttttaca aaggtcgaat  10980
cttgactcaa gcgttaaaga acgtgagcaa gatgtgctta acagctgata tactggggga  11040
ttgttcacaa gcatcatgtt ccaatttagc taccactgta atgcgtctta ctgagaatgg  11100
ggtcgagaaa gatttgtgtt atttcctaaa tgcattcatg acaattagac aattatgtta  11160
tgatctagta tttccccaaa ctaaatctct tagtcaggac attactaatg cttatcttaa  11220
tcatccaata cttatctcaa gattgtgtct attaccatct caattggggg gcttaaactt  11280
tctttcatgt agccgcctgt ttaatagaaa cataggagat ccactagtgt ctgcaattgc  11340
tgatgtgaaa cgattaatta aagcgggctg tctagatatc tgggtcctgt acaacatcct  11400
```

-continued

```
tggaaggagg cctggaaagg gcaagtggag cactctggca gctgatccct atactttaaa  11460
catagattat ttagtccctt caacaacttt tttaaagaaa catgcccaat atacactgat  11520
ggaacggagt gttaatccca tgctccgtgg agtatttagc gaaaatgcag ctgaggagga  11580
agaggaactc gcacagtatc tattagatcg cgaagtagtc atgcccaggg ttgcacatgt  11640
tatacttgcc cagtctagtt gcggtagaag aaaacagatc caaggttact tggattctac  11700
tagaactatt atcaggtatt cactggaggt gagaccactg tcagcaaaga agctgaatac  11760
ggtaatagaa tacaacttgt tgtatctgtc ctacaatttg gagattattg aaaaacccaa  11820
tatagtccaa cctttttgga atgcaatcaa tgttgatact tgtagcatcg atatagctag  11880
gtcccttaga aaactatcct gggcaacttt acttaatgga cgtcccatcg agggattaga  11940
aacacctgat cctattgaat tggtacatgg gtgtttaata atcgggtcag atgagtgtga  12000
gcattgcagt agtggtgatg acaaattcac ctggtttttc ctccccaagg ggataaggtt  12060
agatgatgat ccggcatcta acccacccat cagagtacct tatatcggat ctaaaacaga  12120
tgaacgaagg gttgcatcaa tggcttatat caaagggtca tcagtatcac ttaaatcagc  12180
actcaggttg gcgggggtat atatctgggc tttcggagat acagaggaat catggcagga  12240
tgcctatgag ttagcttcca ctcgtgttaa tctcacacta gagcaattgc aatcgcttac  12300
tcctttacca acatctgcca acctagtcca cagattggat gatggcacta ctcaattaaa  12360
atttacccct gcaagctcct atgcattctc tagctttgtt catatatcta acgactgtca  12420
aattcttgag atcgatgatc aggtaacgga ttctaacctg atttaccagc aagttatgat  12480
tactggcctt gctttaattg agacatggaa taatcctcca atcaacttct ccgtttatga  12540
aactacatta cacttgcata caggctcatc ttgctgtata aggcctgtcg agtcttgtgt  12600
agtaaatccg cctttacttc ctgtcccttt cattaatgtt cctcaaatga ataaatttgt  12660
atatgaccct gaaccactta gtttgctaga aatggaaaaa attgaggata ttgcttatca  12720
aaccagaatt ggtggtttag atcaaatccc gcttctggaa aaaataccct tactagctca  12780
ccttaccgcc aaacagatgg tgaatagcat cactgggctt gatgaagcaa catctataat  12840
gaatgatgct gtagttcaag cagactatac tagcaattgg attagtgaat gctgctacac  12900
ttacattgac tctgtgtttg tttactctgg ctgggcattg ttattggaac tttcatacca  12960
aatgtattac ctaagaattc aaggcataca aggaattcta gactatgtgt atatgacctt  13020
gaggaggata ccaggaatgg ccataacagg catctcatcc acaattagtc accctcgtat  13080
actcagaaga tgcatcaatt tggatgtcat agccccaatc aattctccac acatagcttc  13140
actggattac acaaaattga gcatagatgc agtaatgtgg ggaaccaagc aggtgttgac  13200
caacatttct caaggtatcg attatgagat agttgttcct tctgaaagcc aacttacact  13260
cagtgataga gtcctaaatc tagttgctcg aaaactatca ctactggcaa tcatctgggc  13320
caattacaac tatcctccga aggttaaagg tatgtcacct gaggacaaat gtcaggcttt  13380
aactacacat ctactccaga ctgtcgaata tgttgagtac attcagagtg aaaagacaaa  13440
catcaggagg atgattattg aaccaaaatt aactgcctac cctagtaatt tgttttatct  13500
ctctcgaaag ctgcttaatg ctattcgaga ctctgaagaa ggacaattcc tgattgcatc  13560
ctattataac agttttggat atctggaacc gatattaatg gaatctaaag tattcaatct  13620
aagttcatcc gaatcagcat ctcttacaga attcgatttc atcctcaact tggaattgtc  13680
cgacgccaga cttgagaaat actctctccc aagtttgctt atgacggctg agaatatgga  13740
taacccattt cctcaacccc cacttcatca cgttctcaga ccactaggtt tgtcatccac  13800
```

-continued

```
ctcatggtat aaaacaatca gtgttttgaa ttatattagc catatgaaga tatctgacgg  13860
tgcccatcta tacttggcag agggaagtgg agcctctatg tcacttatag agactttctt  13920
gcccggggaa accatatggt acaacagcct gttcaatagt ggtgagaatc cccctcaacg  13980
taatttcgcc cctttgccca cccagtttat tgaaagtgtc ccctatagat tgattcaagc  14040
aggtatagca gcaggaaatg gtatagtgca aagtttctat ccactctgga acggaaacag  14100
cgatataact gacttaagca ctaaaactag tgttgaatac attatccaca aggtaggagc  14160
tgatacttgt gcattagttc atgtggattt ggaaggtgtc cctggctcaa tgaacagcat  14220
gttggagaga gctcaagtac acgcactact aatcacagtc actgtactga aaccaggcgg  14280
cttactaatc ttgaaagctt catgggaacc ctttaatcga ttttcctttt tactcacagt  14340
actctggcaa ttcttttcca caataaggat cttgcgatct tcatactccg acccgaataa  14400
tcacgaggtt tacataatag ccacattggc agttgatccc actacatcct cctttacaac  14460
tgctctgaat agggcacgca ccctgaatga acagggcttt tcactcatcc cacctgaatt  14520
agtaagtgag tactggagga agcgtgttga acaaggacag attatacagg actgtataga  14580
taaagttata tcagagtgtg tcagagatca atatctggca gacaacaaca ttatcctcca  14640
ggcgggaggt actccaagca caagaaaatg gttggatctg cctgactatt cttcgttcaa  14700
tgaactacaa tctgaaatgg ccagactcat aacaattcat cttaaagagg taatagaaat  14760
cctaaagggc caagcatcag atcatgacac cctattattt acttcataca atgtaggtcc  14820
cctcggaaaa ataaatacaa tactcagatt gattgttgag agaattctta tgtatactgt  14880
gaggaactgg tgtatcttgc ctacccaaac tcgtctcacc ttacgacaat ctatcgagct  14940
tggagagttt agactaagag atgtgataac acccatggag attctaaaac tatcccccaa  15000
caggaaatat ctaaagtctg cattaaatca atcgacattc aaccatctaa tgggagaaac  15060
atctgacata ttgttaaacc gagcttatca gaagagaatt tggaaagcca ttgggtgtgt  15120
aatctattgc tttggtttgc tcaccccgga tgttgaagat tctgagcgca ttgatattga  15180
caatgacata cccgattatg atattcacgg ggacataatt taaatcgaat aaagactctt  15240
ctggcattac acatcaccaa aaagtgccaa actagcatcc aaattcttct aaaccgccca  15300
cgacctcgaa caatcataac cacatcagta ttaaatccag aagatccttt taagaaaaaa  15360
ttgattctac tttctcccct tggt                                          15384
```